(12) United States Patent
Matern et al.

(10) Patent No.: US 9,161,966 B2
(45) Date of Patent: Oct. 20, 2015

(54) GDF15 MUTEIN POLYPEPTIDES

(71) Applicant: NGM Biopharmaceuticals, Inc., South San Francisco, CA (US)

(72) Inventors: Hugo Matern, San Mateo, CA (US); Darrin Anthony Lindhout, Mountain View, CA (US); Raj Haldankar, Redwood City, CA (US)

(73) Assignee: NGM Biopharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 14/165,391

(22) Filed: Jan. 27, 2014

(65) Prior Publication Data

US 2014/0213511 A1 Jul. 31, 2014

Related U.S. Application Data

(60) Provisional application No. 61/758,456, filed on Jan. 30, 2013.

(51) Int. Cl.
*A61K 38/00* (2006.01)
*A61K 38/16* (2006.01)
*A61K 38/17* (2006.01)
*A61K 38/18* (2006.01)
*C07K 14/00* (2006.01)
*C07K 14/435* (2006.01)
*C07K 14/46* (2006.01)
*C07K 14/47* (2006.01)
*C07K 14/475* (2006.01)
*C12N 15/11* (2006.01)
*C12N 15/12* (2006.01)
*C12N 15/62* (2006.01)
*C12N 15/63* (2006.01)

(52) U.S. Cl.
CPC ........... *A61K 38/1841* (2013.01); *C07K 14/475* (2013.01); *A61K 38/00* (2013.01)

(58) Field of Classification Search
None
See application file for complete search history.

(56) References Cited

U.S. PATENT DOCUMENTS

| 5,876,969 | A | 3/1999 | Fleer et al. |
| 5,994,102 | A | 11/1999 | Hudson et al. |
| 6,051,424 | A | 4/2000 | Kato et al. |
| 6,107,476 | A * | 8/2000 | Erlander et al. ........... 536/23.51 |
| 6,165,470 | A | 12/2000 | Becquart et al. |
| 6,180,602 | B1 | 1/2001 | Kato et al. |
| 6,420,543 | B1 | 7/2002 | Lee et al. |
| 6,465,181 | B2 | 10/2002 | Biling-Medel et al. |
| 6,500,638 | B2 | 12/2002 | Hudson et al. |
| 6,521,227 | B1 | 2/2003 | Hudson et al. |
| 6,524,802 | B1 | 2/2003 | Lee et al. |
| 6,686,179 | B2 | 2/2004 | Fleer et al. |
| 6,905,688 | B2 | 6/2005 | Rosen et al. |
| 6,972,322 | B2 | 12/2005 | Fleer et al. |
| 6,989,365 | B2 | 1/2006 | Fleer et al. |
| 7,056,701 | B2 | 6/2006 | Fleer et al. |
| 7,081,354 | B2 | 7/2006 | Fleer et al. |
| 7,094,577 | B2 | 8/2006 | Fleer et al. |
| 7,141,661 | B2 | 11/2006 | Eling et al. |
| 7,157,235 | B2 | 1/2007 | Breit et al. |
| 7,244,833 | B2 | 7/2007 | Yu et al. |
| 7,276,593 | B2 | 10/2007 | Vernet et al. |
| 7,282,351 | B2 | 10/2007 | Hudson et al. |
| 7,410,779 | B2 | 8/2008 | Fleer et al. |
| 7,435,410 | B2 | 10/2008 | Fleer et al. |
| 7,442,371 | B2 | 10/2008 | Yu et al. |
| 7,514,221 | B2 | 4/2009 | Breit et al. |
| 7,833,521 | B2 | 11/2010 | Fleer et al. |
| 7,863,239 | B2 | 1/2011 | Timmerman et al. |
| 7,919,084 | B2 | 4/2011 | Breit et al. |
| 7,968,303 | B2 | 6/2011 | Breit et al. |
| 8,084,021 | B2 | 12/2011 | Yu et al. |
| 8,192,735 | B2 | 6/2012 | Breit et al. |
| 8,222,384 | B2 | 7/2012 | Wolfman et al. |
| 8,252,739 | B2 | 8/2012 | Rosen et al. |
| 2001/0011077 | A1 | 8/2001 | Albone et al. |
| 2003/0023073 | A1 | 1/2003 | Hsiao et al. |
| 2003/0053431 | A1 | 3/2003 | Madour et al. |
| 2003/0232347 | A1 | 12/2003 | Anderson et al. |
| 2003/0232385 | A1 | 12/2003 | Breit et al. |
| 2004/0029770 | A1 | 2/2004 | Baek et al. |
| 2004/0053325 | A1 | 3/2004 | Breit et al. |
| 2006/0148709 | A1 | 7/2006 | Unsicker et al. |
| 2006/0253913 | A1 | 11/2006 | Huang et al. |
| 2007/0077598 | A1 | 4/2007 | Breit et al. |
| 2007/0166310 | A1 | 7/2007 | Hudson et al. |
| 2009/0004181 | A1 | 1/2009 | Breit et al. |
| 2009/0042780 | A1 | 2/2009 | Knopf et al. |
| 2009/0291889 | A1 | 11/2009 | Breit et al. |

(Continued)

FOREIGN PATENT DOCUMENTS

| EP | 1179067 | 12/2006 |
| EP | 1279039 | 1/2008 |
| EP | 1914554 | 4/2008 |
| EP | 0833912 | 2/2009 |
| EP | 2383571 | 11/2011 |

(Continued)

OTHER PUBLICATIONS

Wells, 1990, Biochemistry 29:8509-8517.*
Ngo et al., 1994, The Protein Folding Problem and Tertiary Structure Prediction, Birkhauser, Boston, pp. 492-495.*
Tokuriki et al., 2009, Curr. Opin. Struc. Biol. 19:596-604.*
U.S. Appl. No. 14/373,617, filed Mar. 8, 2013, Lindhout.

(Continued)

*Primary Examiner* — Elizabeth C Kemmerer
(74) *Attorney, Agent, or Firm* — Carol L. Francis; Shweta Chandra; Bozicevic, Field & Francis LLP

(57) ABSTRACT

Methods of treating individuals with a glucose metabolism disorder and/or a body weight disorder, and compositions associated therewith, are provided.

25 Claims, 26 Drawing Sheets

(56) References Cited

U.S. PATENT DOCUMENTS

| | | | |
|---|---|---|---|
| 2010/0112692 | A1 | 5/2010 | Rezania et al. |
| 2010/0184217 | A1 | 7/2010 | Cegilski et al. |
| 2010/0221777 | A1 | 9/2010 | Choe et al. |
| 2010/0261284 | A1 | 10/2010 | Spanuth |
| 2010/0266707 | A1 | 10/2010 | Breit et al. |
| 2010/0278843 | A1 | 11/2010 | Breit et al. |
| 2011/0033886 | A1 | 2/2011 | Hess et al. |
| 2011/0039284 | A1 | 2/2011 | Breit et al. |
| 2011/0065204 | A1 | 3/2011 | Wollert et al. |
| 2011/0107821 | A1 | 5/2011 | Hess et al. |
| 2011/0123454 | A1 | 5/2011 | Breit et al. |
| 2011/0257022 | A1 | 10/2011 | Hess et al. |
| 2011/0262444 | A1 | 10/2011 | Kim et al. |
| 2011/0263443 | A1 | 10/2011 | Hess et al. |
| 2011/0300562 | A1 | 12/2011 | Lambrecht et al. |
| 2012/0107420 | A1 | 5/2012 | Breit et al. |
| 2012/0128624 | A1 | 5/2012 | Yu et al. |
| 2012/0309697 | A1 | 12/2012 | Breit et al. |
| 2013/0071935 | A1 | 3/2013 | Bergman et al. |
| 2013/0323835 | A1 | 12/2013 | McDonald et al. |
| 2014/0086915 | A1 | 3/2014 | Breit et al. |
| 2014/0193427 | A1 | 7/2014 | Lerner et al. |

FOREIGN PATENT DOCUMENTS

| | | |
|---|---|---|
| EP | 2439535 | 4/2012 |
| EP | 2441466 | 4/2012 |
| JP | 07-258293 | 10/1995 |
| JP | 1995250688 | 10/1995 |
| WO | WO94/03599 | 2/1994 |
| WO | 96/18730 | 6/1996 |
| WO | WO97/00958 | 1/1997 |
| WO | WO97/36926 | 10/1997 |
| WO | WO98/11224 | 3/1998 |
| WO | WO99/06445 | 2/1999 |
| WO | WO01/81928 | 11/2001 |
| WO | WO02/092620 | 11/2002 |
| WO | 03000448 | 1/2003 |
| WO | WO2005/099746 | 10/2005 |
| WO | WO2005/113585 | 12/2005 |
| WO | WO2009/021293 | 2/2009 |
| WO | WO2009/046495 | 4/2009 |
| WO | 2009141357 | 11/2009 |
| WO | WO2010/048670 | 5/2010 |
| WO | WO2010/099219 | 9/2010 |
| WO | WO2011/050407 | 5/2011 |
| WO | 2011064758 | 6/2011 |
| WO | WO2011/127458 | 10/2011 |
| WO | 2012025355 | 3/2012 |
| WO | WO2012/138919 | 10/2012 |
| WO | WO 2013/113008 | 8/2013 |
| WO | WO2013/113008 | 8/2013 |
| WO | WO2013/148117 | 10/2013 |
| WO | WO2014/000042 | 1/2014 |
| WO | WO2014/100689 | 6/2014 |
| WO | 2015/017710 | 2/2015 |

OTHER PUBLICATIONS

Bauskin, et al., "The Propeptide Mediates Formation of Stromal Stores of PROMIC-1: Role in Determining Prostate Cancer Outcome", Cancer Research, 2005, 65(6), 2330-2336.
Breit et al. "The TGF-beta superfamily cytokine, MIC-1/GDF15: a pleotrophic cytokine with roles in inflammation, cancer and metabolism" Growth Factors, 2011, 29(5):187-95.
Bootcov et al. "MIC-1, a novel macrophage inhibitory cytokine, is a divergent member of the TGF-beta superfamily" Proc. Natl. Acad. Sci. USA, 1997, 94:11514-11519.
Dostalova et al. "Increased serum concentrations of macrophage inhibitory cytokine-1 in patients with obesity and type 2 diabetes mellitus: the influence of very low calorie diet", Eur. J. Endocrinol., 2009, 161:397-404.
Hromas et al. "PLAB, a novel placental bone morphogenetic protein" Biochim. Biophys. Acta, 1997, 1354:40-4.
Johnen, et al., "Tumor-induced anorexia and weight loss are mediated by the TGF-b superfamily cytokine MIC-1", Nature Medicine, 2007, 13 (11): 1333-1340.
Paralkar et al. "Cloning and characterization of a novel member of the transforming growth factor[beta]/bone morphogenetic protein family" J. Biol. Chem, 1998, 273:13760-13767.
Yokoyama-Kobayashi et al. "Human cDNA encoding a novel TGF-beta superfamily protein highly expressed in placenta" J. Biochem, 1997, 122:622-626.
Chen et al. "Substitution of asparagine residues in Aspergillus awamori glucoamylase by site-directed mutagenesis to eliminate N-glycosylation and inactivation by deamidation" Biochem J., 1994, 301: 275-81.
Friedman et al. "Degradation of growth hormone releasing factor analogs in neutral aqueous solution is related to deamidation of asparagine residues" Int. J. Peptide Protein Res., 1991, 37:14-20.
Robinson et al. "Prediction of primary structure deamidation rates of asparaginyl and glutaminyl peptides through steric and catalytic effects" J. Pepide Res., 2004, 63:437-448.
Fairlie et al. (2000) "Expression of a TGF-βsuperfamily protein, macrophage inhibitory cytokine-1, in the yeast Pichia pastoris" Gene 254:67-76.
Bauskin et al (2000) "The Propeptide of Macrophage Inhibitory Cytokine (MIC-1), a TGF-Superfamily Member, Acts as a Quality Control Determinant for Correctly Folded MIC-1" EMBO J 19:2212-2220.
Fairlie et al. (2001) "Epitope Mapping of the Transforming Growth Factor-Superfamily Protein, Macrophage Inhibitory Cytokine-1 (MIC-1): Identification of at Least Five Distinct Epitope Specificities" Biochem 40:65-73.
Clee et al., (2007) "The Genetic Landscape of Type 2 Diabetes in Mice", Endocrine Reviews 28(1): 48-83.
Hamann et al. (1996) "Regulation of energy balance by leptin" Exp Endocrinol Diabetes 104:293-200.
Soler et al., (2012) "New Experimental Models of Diabetic Nephropathy in Mice Models of Type2 Diabetes: Efforts to Replicate Human Nephropathy" Experimental Diabetes Research, vol. 2012, Art. ID 616313.
Macia et al., (2012) "Macrophage Inhibitory Cytokine 1 (MIC-1/GDF15) Decreases Food Intake, Body Weight and Improves Glucose Tolerance in Mice on Normal & Obesogenic Diets", PLoS ONE, 7(4):1-8.
Vila et al., (2011), "The Relationship between Insulin Resistance and the Cardiovascular Biomarker Growth Differentiation Factor-15 in Obese Patients", Clinical Chemistry, 57(2):309-316.
Ehses et al., (2007), "Increased Number of Islet-Associated Macrophages in Type 2 Diabetes", Diabetes, 56:2356-2370.
Lind et al., (2009), "Growth-differentiation factor-15 is an independent marker of cardiovascular dysfunction and disease in the elderly: results from the Prospective Investigation of the Vasculature in Uppsala Seniors (PIVUS) Study", European Heart Journal, 30(19),2346-2353.
Lajer et al., (2010) "Plasma growth differentiation factor-15 independently predicts all-cause and cardiovascular mortality as well as deterioration of kidney function in type 1 diabetic patients with nephropathy", Diabetes Care, 33 (7), 1567-1572.
Bootcov et al., (1997), "MIC-1, a novel macrophage inhibitory cytokine, is a divergent member of the TGF-b superfamily", Proc. Natl. Acad. Sci. USA, 94:11514-11519.

* cited by examiner

Figure 1A

Human GDF15 Precursor Amino Acid Sequence (GenBank Accession No. NP_004855.2; SEQ ID NO:1)

```
  1 MPGQELRTVN GSQMLLVLLV LSWLPHGGAL SLAEASRASF PGPSELHSED SRFRELRKRY
 61 EDLLTRLRAN QSWEDSNTDL VPAPAVRILT PEVRLGSGGH LHLRISRAAL PEGLPEASRL
121 HRALFRLSPT ASRSWDVTRP LRRQLSLARP QAPALHLRLS PPPSQSDQLL AESSSARPQL
181 ELHLRPQAAR GRRRARARNG DHCPLGPGRC CRLHTVRASL EDLGWADWVL SPREVQVTMC
241 IGACPSQFRA ANMHAQIKTS LHRLKPDTVP APCCVPASYN PMVLIQKTDT GVSLQTYDDL
301 LAKDCHCI
```

Human GDF15 Precursor Nucleic Acid Sequence (GenBank Accession No. NM_004864.2; SEQ ID NO:2)

```
   1 AGTCCCAGCT CAGAGCCGCA ACCTGCACAG CCATGCCCGG GCAAGAACTC AGGACGGTGA
  61 ATGGCTCTCA GATGCTCCTG GTGTTGCTGG TGCTCTCGTG GCTGCCGCAT GGGGGCGCCC
 121 TGTCTCTGGC CGAGGCGAGC CGCGCAAGTT TCCCGGGACC CTCAGAGTTG CACTCCGAAG
 181 ACTCCAGATT CCGAGAGTTG CGGAAACGCT ACGAGGACCT GCTAACCAGG CTGCGGGCCA
 241 ACCAGAGCTG GGAAGATTCG AACACCGACC TCGTCCCGGC CCCTGCAGTC CGGATACTCA
 301 CGCCAGAAGT GCGGCTGGGA TCCGGCGGCC ACCTGCACCT GCGTATCTCT CGGGCCGCCC
 361 TTCCCGAGGG GCTCCCCGAG GCCTCCCGCC TTCACCGGGC TCTGTTCCGG CTGTCCCCGA
 421 CGGCGTCAAG GTCGTGGGAC GTGACACGAC CGCTGCGGCG CCAGCTCAGC CTTGCAAGAC
 481 CCCAGGCGCC CGCGCTGCAC CTGCGACTGT CGCCGCCGCC GTCGCAGTCG GACCAACTGC
 541 TGGCAGAATC TTCGTCCGCA CGGCCCCAGC TGGAGTTGCA CTTGCGGCCG CAAGCCGCCA
 601 GGGGGCGCCG CAGAGCGCGT GCGCGCAACG CGCGCAACTG TCCGCTCGGG CCCGGGCGTT
 661 GCTGCCGTCT GCACACGGTC CGCGCGTCGC TGGAAGACCT GGGCTGGGCC GATTGGGTGC
 721 TGTCGCCACG GGAGGTGCAA GTGACCATGT GCATCGGCGC GTGCCCGAGC CAGTTCCGGG
 781 CGGCAAACAT GCACGCGCAG ATCAAGACGA GCCTGCACCG CCTGAAGCCC GACACGGTGC
 841 CAGCGCCCTG CTGCGTGCCC GCCAGCTACA ATCCCATGGT GCTCATTCAA AAGACCGACA
 901 CCGGGGTGTC GCTCCAGACC TATGATGACT TGTTAGCCAA AGACTGCCAC TGCATATGAG
 961 CAGTCCTGGT CCTTCCACTG TGCACCTGCG CGGAGGACGC GACCTCAGTT GTCCTGCCCT
1021 GTGGAATGGG CTGAGTTC CTGAGACACC CCAAACAGCT GTATTTATAT
1081 AAGTCTGTTA TTTATTATTA ATTTATTGGG GTGACCTTCT TGGGGACTCG GGGGCTGGTC
1141 TGATGGAACT GTGTATTTAT TTAAAACTCT GGTGATAAAA ATAAAGCTGT CTGAACTGTT
1201 AAAAAAAAAA AAAAAAAAAA
```

Figure 1B

Mature Human GDF15 Amino Acid Sequence (GenBank Accession No. NP_004855.2; SEQ ID NO:3)

ARNGDHCPLGPGRCCRLHTVRASLEDLGWADWVLSPREVQVTMCIGACPSQFRAANMHAQIKTSLHRLKPDTVPAPCCVPASYNPMVLIQKTDTGVSL
QTYDDLLAKDCHCI

Mature Human GDF15 Nucleic Acid Sequence (GenBank Accession No. NM_004864.2; SEQ ID NO:4)

GCGCGTAACGGGGATCACTGTCCCGCTCGGGCTCCGGGCCCCGGGCGTTGCTGCGTCTGCACACGGTCCGCGCGT
CGCTGGAAGACCTGGGCTGGGCCGATTGGGTGCTGTCGCCACGGAGGTGCAAGTGACCATGTGCATCGG
CGCTGCCCGAGCCAGTTCCGGGCGCAAACATGCACGCGCAGATCAAGACGAGCCTGCACCGCCTGAAG
CCCGACACGGTGCCAGCGCCCTGCTGCGTGCCCGCCAGCTACAATCCCATGGTGCTCATTCAAAAGACCG
ACACCGGGGTGTCGCTCCAGACCTATGATGACTTGTTAGCCAAAGACTGCCACTGCATATAA

Figure 1C

Amino Acid Sequence of Precursor (Endogenous Signal Peptide and Small Prodomain) and Mature Human Serum Albumin (GenBank Accession No. AAA98797.1; SEQ ID NO:5)

MKWVTFISLLFLFSSAYSRGVFRRDAHKSEVAHRFKDLGEENFKALVLIAFAQYLQQCPFEDHVKLVNEVTEFAKTCVADESAENCDKSLHTLFGDKL
CTVATLRETYGEMADCCAKQEPERNECFLQHKDDNPNLPRLVRPEVDVMCTAFHDNEETFLKKYLYEIARRHPYFYAPELLFFAKRYKAAFTECCQAA
DKAACLLPKLDELRDEGKASSAKQRLKCASLQKFGERAFKAWAVARLSQRFPKAEFAEVSKLVTDLTKVHTECCHGDLLECADDRADLAKYICENQDS
ISSKLKECCEKPLLEKSHCIAEVENDEMPADLPSLAADFVESKDVCKNYAEAKDVFLGMFLYEYARRHPDYSVVLLLRLAKTYETTLEKCCAAADPHE
CYAKVFDEFKPLVEEPQNLIKQNCELFEQLGEYKFQNALLVRYTKKVPQVSTPTLVEVSRNLGKVGSKCCKHPEAKRMPCAEDYLSVVLNQLCVLHEK
TPVSDRVTKCCTESLVNRRPCFSALEVDETYVPKEFNAETFTFHADICTLSEKERQIKKQTALVELVKHKPKATKEQLKAVMDDFAAFVEKCCKADDK
ETCFAEEGKKLVAASQAALGL

Figure 1C, continued

DNA Sequence Encoding Precursor (Endogenous Signal Peptide and Small Prodomain) and Mature Human Serum Albumin (GenBank Accession No. NM_000477.5; SEQ ID NO:6)

```
   1 agtatattag tgctaatttc cctccgtttg tcctagcttt tctcttctgt caacccaca
  61 cgcctttggc acaatgaagt gggtaacctt tatttccctt cttttctct ttagctcggc
 121 ttattccagg ggtgtgtttc gtcgagatgc acacaagagt gaggttgctc atcggtttaa
 181 agatttggga gaagaaaatt tcaaagcctt ggtgttgatt gccttgtctc agtatcttca
 241 gcagtgtcca tttgaagatc atgtaaaatt agtgaatgaa gtaactgaat ttgcaaaaac
 301 atgtgttgct gatgagtcag ctgaaaattg tgacaaatca cttcataccc ttttggaga
 361 caaattatgc acagttgcaa ctcttcgtga aacctatggt gaaatgctg actgctgtgc
 421 aaaacaagaa cctgagagaa atgaatgctt cttgcaacac aaagatgaca acccaaacct
 481 cccccgattg gtgagaccag aggttgatgt gatgtgcact gcttttcatg acaatgaaga
 541 gacatttttg aaaaaatact tatatgaaat tgccagaaga agctgctttt catccttact tttatgcccc
 601 ggaactcctt ttctttgcta aaggtataa agctgctttt acagaatgtt gccaagctgc
 661 tgataaagct gcctgcctgt tgccaaagct cgatgaactt cgggatgaag ggaaggcttc
 721 gtctgccaaa cagagactca agtgtgccag tctccaaaaa tttggagaaa gagctttcaa
 781 agcatgggca gtagctcgcc tgagccagag atttcccaaa gctgagtttg cagaagtttc
 841 caagttagtg acagatctta cctttgccaa cacggaatgc tgccatgagt atcgcttga
 901 atgtgctgat gacagggcgg accttgccaa gtatatctgt gaaaatcaag attcgatctc
 961 cagtaaactg aaggaatgct gtgaaaaacc tctgttgaa aatcccact gcattgccga
1021 agtgaaaat gatgagatgc ctgctgactt gcccttcatta gctgctgatt ttgttgaaag
1081 taaggatgtt tgcaaaaact atgctgaggc aaaggatgtc ttcctgggca tgtttttgta
1141 tgaatatgca agaaggcatc ctgattactc tgtcgtgctg ctgctgagac ttgccaagac
1201 atatgaaacc actctagaga agtgctgtgc cgctgcagat cctcatgaat gctatgccaa
1261 agtgttcgat gaatttaaac ctcttgtgga agagcctcag aatttaatca aacaaaattg
1321 tgagcttttt gagcagcttg gagagtacaa attccagaat gcgctattag ttcgttacac
1381 caagaaagta cccaagtgt caactccaac tcttgtagag gtctcaagaa acctaggaaa
1441 agtgggcagc aaatgttgta aacatcctga agcaaaagga atgccctgtg cagaagacta
1501 tctatccgtg gtcctgaacc agttatgtgt gttgcatgag aaaacgccag taagtgacag
1561 agtcaccaaa tgctgcacag aatccttggt gaacaggcga ccatgctttt cagctctgga
1621 agtcgatgaa acatacgttc ccaaagagtt taatgctgaa acattcacct tccatgcaga
1681 tatatgcaca ctttctgaga aggagacaca aatcaagaaa caaactgcac ttgttgagct
1741 cgtgaaacac aagcccaagg caacaaaaga gcaactgaa gctgttatgg atgatttcgc
```

Figure 1C, continued

```
1801  agcttttgta gagaagtgct gcaaggctga cgataaggag acctgctttg ccgaggaggg
1861  taaaaaactt gttgctgcaa gtcaagctgc cttaggctta taacatcaca tttaaaagca
1921  tctcagccta ccatgagaat aagagaaaga aaatgaagat caaaagctta ttcatctgtt
1981  tttcttttc gttggtgtaa agccaacacc ctgtctaaaa aacataaaat tctttaatca
2041  tttgcctct tttctctgtg cttcaattaa taaaaaatgg aaagaatcta atagagtggt
2101  acagcactgt tattttcaa agatgtgttg ctatcctgaa aattctgtag gttctgtgga
2161  agttccagtg ttctctctta ttccacttcg gtagaggatt tctagtttct tgtgggctaa
2221  ttaaataaat cattaatact cttctaaaaa aaaaaaaaa aaaa
```

Amino Acid Sequence of IgK Signal Peptide and Mature Human Serum Albumin (SEQ ID NO:7)

MDMRVPAQLLGLLLLWLRGARCDAHKSEVAHRFKDLGEENFKALVLIAFAQYLQQCPFEDHVKLVNEVTEFAKTCVADESAENCDKSLHTLFGDKLCT
VATLRETYGEMADCCAKQEPERNECFLQHKDDNPNLPRLVRPEVDVMCTAFHDNEETFLKKYLYEIARRHPYFYAPELLFFAKRYKAAFTECCQAADK
AACLLPKLDELRDEGKASSAKQRLKCASLQKFGERAFKAWAVARLSQRFPKAEFAEVSKLVTDLTKVHTECCHGDLLECADDRADLAKYICENQDSIS
SKLKECCEKPLLEKSHCIAEVENDEMPADLPSLAADFVESKDVCKNYAEAKDVFLGMFLYEYARRHPDYSVVLLLRLAKTYETTLEKCCAAADPHECY
AKVFDEFKPLVEEPQNLIKQNCELFEQLGEYKFQNALLVRYTKKVPQVSTPTLVEVSRNLGKVGSKCCKHPEAKRMPCAEDYLSVVLNQLCVLHEKTP
VSDRVTKCCTESLVNRRPCFSALEVDETYVPKEFNAETFTFHADICTLSEKERQIKKQTALVELVKHKPKATKEQLKAVMDDFAAFVEKCCKADDKET
CFAEEGKKLVAASQAALGL

Figure 1C, continued

DNA Sequence Encoding IgK Signal Peptide and Mature Human Serum Albumin (SEQ ID NO:8)

```
ATGGACACATGAGGGTCCCCGCTCAGCTCCTCTGGGGCTCCTCCTGCTACTCTGCTCCTGGCTCCCAGATGTGATGCACACAAGAGTGAGGTTGCTCATCGGTT
TAAAGATTTGGGAGAAGAAATTTCAAAGCCTTGGTGTTGATTGCCTTTGCTCAGTATCTTCAGCAGTGTCCATTTGAAGATCATGTAAAATTAGTGA
ATGAAGTAACTGAATTTGCAAAAACATGTGTTGCTGATGAGTCAGCTGAAAATTGTGACAAGTCACTTCATACCCTTTTGGAGACAAATTATGCACA
GTTGCAACTCTTCGTGAAACCTATGGTGAAACTGGCTGACTGCTGTGCAAAAACAAGAACCTGCCTTTTCATGACAATGAAGAGACAATTTGACAA
CCCAAACCTCCCCCGATTGGTGAGACCAGAGGTTGATGTGCACTGCTTTGATGTGCAGAACTCCTTTCTTTGCTAAAAGGTATAAAGCTCAAGCTGCCAAGCAA
TTGCCAGAAGACATCCTTACTTTTATGCCCGGAGACATCTCGGGATGAACTTCGGGATGAAGGGAAGGCTTCGTCTGCCAAACAGAGACTCAAGTGTGCCAGTCTCCAAAAATTGG
GCTGCCTGCTGTTGCAAAGCTTTCAAAGCATGGCCATGGCAGTCTCCGCCCTGAACTGCTTGAATGTGCTTGATGACAGGGCCATTGCCGAAGTTCCAAGTTAGTGACAGATCTTACCA
AGAAAGAGCTTCCACACGGAATGCTGCATGCAGGAATCCCTCGTTGCAAAGCTGTGAAAGTAAGGAATGCTGTGAAAGTAACCTCGTTGCAAACTTATGCTGAGGATGTTCCTGGGCATGTTTTGTATGAATGCAAGAAGGC
AGTGCTGTGATTTGTTGAAAGTAAGGAATGCTGCATGCAGGAATCCCTCGTTGCAAAGCTGTGAAAGTAACCTCGTTGCAAACTTATGCTGAGGATGTTCCTGGGCATGTTTTGTATGAATGCAAGAAGGC
ATCCTGATTACTCTCGTCGTGATGAATTTAAACCTCTTGTGGAGACTTGCCAAGACATGAAGACCTCAGAATTTAATCAAACAACTCTTCAACTCGTCGTCTTTGAGCAGCTTGAGCAGCTTCATGAGAGTACAAATT
GCCAAAGTGTTCGATGAGCTATTAGTTCGTTACACCAAGAAAGATGCCCGTGCAGAAGAATGCCCCTGTGCAGAAGAATGCCCCTGTGCAGACTATCTATCCGTGGTCTGAACCAGTTATGTGTTGCATGAGAAAACGCCA
CCAGAATGCGCTATTAGTTCGTTACACCAAGAAAGATGCCCGTGCAGAAGAATGCCCCTGTGCAGACTATCTATCCGTGGTCTGAACCAGTTATGTGTTGCATGAGAAAACGCCA
AATGTTGTAAACATCCTGAAGCAAAATGCTGCACAGAATCCTTGGTGAACACCACTTTCTGAAGTCGATGAAACATACGTTCCCAAAGA
GTAAGTGACAGAGTCACCAAATTCACCTTCCATGCAGATATGCAACTGAAAGCTGTTATGATGATTTCGCAGCTTTGTAGAGAAGCGCTGCAAGGTAGGAGACC
GTTTAATGCTGAAACATTGCTAAACATTCACCTTCCATGCAGATATGCAACTGAAAGCTGTTATGATGATTTCGCAGCTTTGTAGAGAAGCGCTGCAAGGTAGGAGACC
AACAAGCCCAAGGCAACAAAAGAGCAACTGAAAACTTGTTGCTGCAAGTCAAGTCTGCCTTAGGCTTA
TGCTTTGCCGAGGAGGGTAAAAAACTTGTTGCTGCAAGTCAAGTCTGCCTTAGGCTTA
```

Figure 1D

Mature Human Serum Albumin Amino Acid Sequence (Subsequence of Amino Acid Sequence of Figure 1C Lacking the IgK Signal Peptide) (SEQ ID NO:9)

```
DAHKSEVAHRFKDLGEENFKALVLIAFAQYLQQCPFEDHVKLVNEVTEFAKTCVADESAENCDKSLHTLFGDKLCTVATLRETYGEMADCCAKQEPER
NECFLQHKDDNPNLPRLVRPEVDVMCTAFHDNEETFLKKYLYEIARRHPYFYAPELLFFAKRYKAAFTECCQAADKAACLLPKLDELRDEGKASSAKQ
RLKCASLQKFGERAFKAWAVARLSQRFPKAEFAEVSKLVTDLTKVHTECCHGDLLECADDRADLAKYICENQDSISSKLKECCEKPLLEKSHCIAEVE
NDEMPADLPSLAADFVESKDVCKNYAEAKDVFLGMFLYEYARRHPDYSVVLLLRLAKTYETTLEKCCAAADPHECYAKVFDEFKPLVEEPQNLIKQNC
ELFEQLGEYKFQNALLVRYTKKVPQVSTPTLVEVSRNLGKVGSKCCKHPEAKRMPCAEDYLSVVLNQLCVLHEKTPVSDRVTKCCTESLVNRRPCFSA
LEVDETYVPKEFNAETFTFHADICTLSEKERQIKKQTALVELVKHKPKATKEQLKAVMDDFAAFVEKCCKADDKETCFAEEGKKLVAASQAALGL
```

Mature Human Serum Albumin DNA Sequence (Subsequence of DNA Sequence of Figure 1C Lacking the IgK Signal Peptide) (SEQ ID NO:10)

```
GATGCACACAAGAGTGAGGTTGCTCATCGGTTTGCTCTTCAAAGCCTTGGTGTTGATTGCCTTTGCTCAGTATCTTCAGCA
GTGTCCATTTGAAGATCATTGTAAAATTAGTAACTGAAGTAACTGAATTTGCAAAACATGTGTTGCTGATGAGTCAGCTGAAAATTGTGACAAATCAC
TTCATACCCTTTTTGGAGACAACAATTATGCACAGTTGCAACTCTTCGTGAAATGGCTGACTGCTGTGCAAAACAAGAACCTGAGAGA
AATGAATGCTTCTTGCAACACAAAGATGACAACCCAAACCTATGGTGAGACCAGAGGTTGATGTGCACTGCTTTTCATGACAATGA
AGAGACATTTTTGAAAAATACTTATATGAAATTGCCAGAAGACATCCTTTGTGCCCCGATTGGTGAGAACTCCTTTCTTTGCTAAAAGGTATAAAGCTG
CTTTTACAGAATGTTGCCAAGCTGCTCAAAAAAGTCGAGATAGCTGTGCCAAAGCTTCAAAGCGAGGGAAGTCGCTGTCCTGCCAAACAG
AGACTCAAGTGTGCCAGTTAGTGACAGATCTTCAAAAATTTGGAGAAAGAGCTTCAAAGACATGGGACAGTAGCTCGCCTGCTGAATGTCTGATGACAGGGCGGACCTTGCCA
AGAAGTTTCAAGTGCATATCTGTGAAAATCAGATTCGATCTCCAGTAACTGAAGAATGCTGCCATGGAGAATCCCACTGCATTGCCGAAGTGGAA
AATGATGAGATGCCTGCTGATGAATATGCAAGAAGGCATCCTGATTACCTCTGTGTCTGCTGAGACTTGCCAAGACATATGAAACCACTCTAGAGAAGT
GGGCATGTTTTTGTTGTATGAATGAAATGCTGCAGATCCTCATGAATGTTGCAAAGTGTTCGATGAATTTAAACCTCTTGTGGAAGAGCCTCAGAATTTAATCAAACAAATTGT
GCTGTGCCGCTGCAGATCCTCATGAATGCTATGCCAAGGTGTTCGATGAATTTAAACCTCTTGTGGAAGAGCCTCAGAATTTAATCAAACAAATTGT
GAGCTTTTTGAGCAGCTGGAGAATACAAATTCCAGAATGCGCTATTAGTTCGTTACACCAAGAAAGTACCCCAAGTGTCAACTCTGTCAACTCTTGTAGA
GGTCTCAAGAACCTAGGAAGAAAGTGGGCAGCAAATGTTGTAAACATCCTGAAGCAAAAGAATGCCCTGTGCAGAAGACTATCTATCCGTGGTCCTGA
ACCAGTTATGTGTTGCATGAGAAAACGCCAGTAAGTGACAGAGTCACCAAGTCCTTGGTGAACAGGCGACCATGCTTTTCAGCT
CTGGAAGTCGATGAAACATACGTTCCCAAAGAGTTTAATGCTGAAACATTCACCTTCCATGCAGATATATGCACACTTTCTGAGAAGGAGAGACAAAT
CAAGAAACAAACTGCACTTGTTGAGCTCGTGAAACACAAGCCCAACAAAGAGCAACTGAAAGCTGTTATGGATGATTTCGCAGCTTTTGTAG
AGAAGTGCTGCAAGGCTGACGATAAGGAGACCTGCTTTGCCGAGGAGGGTAAAAAACTTGTTGCTGCCAAGTCAAGCTCAAGCTTA
```

Figure 1E

Fusion Molecule Comprising HSA Amino Acid Sequence Having an IgK Signal Sequence Fused to the N-Terminus of Mature Human GDF15 Amino Acid Sequence Through a Protease-sensitive Cleavable Linker (SEQ ID NO:11)

MDMRVPAQLLGLLLLWLRGARCDAHKSEVAHRFKDLGEENFKALVLIAFAQYLQQCPFEDHVKLVNEVTEFAKTCVADESAENCDKSLHTLFGDKLCT
VATLRETYGEMADCCAKQEPERNECFLQHKDDNPNLPRLVRPEVDVMCTAFHDNEETFLKKYLYEIARRHPYFYAPELLFFAKRYKAAFTECCQAADK
AACLLPKLDELRDEGKASSAKQRLKCASLQKFGERAFKAWAVARLSQRFPKAEFAEVSKLVTDLTKVHTECCHGDLLECADDRADLAKYICENQDSIS
SKLKECCEKPLLEKSHCIAEVENDEMPADLPSLAADFVESKDVCKNYAEAKDVFLGMFLYEYARRHPDYSVVLLLRLAKTYETTLEKCCAAADPHECY
AKVFDEFKPLVEEPQNLIKQNCELFEQLGEYKFQNALLVRYTKKVPQVSTPTLVEVSRNLGKVGSKCCKHPEAKRMPCAEDYLSVVLNQLCVLHEKTP
VSDRVTKCCTESLVNRRPCFSALEVDETYVPKEFNAETFTFHADICTLSEKERQIKKQTALVELVKHKPKATKEQLKAVMDDFAAFVEKCCKADDKET
CFAEEGKKLVAASQAALGLGGGSGGGGSIEGRARNGDHCPLGPGRCCRLHTVRASLEDLGWADWVLSPREVQVTMCIGACPSQFRAANMHAQIKTSL
HRLKPDTVPAPCCVPASYNPMVLIQKTDTGVSLQTYDDLLAKDCHCI

Figure 1E, continued

Nucleic Acid Encoding A Fusion Molecule Comprising HSA Amino Acid Sequence Having an IgK Signal Sequence Fused to the N-Terminus of Mature Human GDF15 Amino Acid Sequence Through a Protease-sensitive Cleavable Linker (SEQ ID NO:12)

```
ATGGACATGAGAGGTCCCCGCTCAGCTCCTCTGGGCTCCTGCTACTCTGGCTCCTGCTGCTCCGAGGTGCCAGAGTGTGATGCACAAGAGTGAGGTTGCTCATCGGTT
TAAAGATTTGGGAGAAGAAATTTCAAAGCCTTGGTGTTGAAAGCCTTTGATTGCCTTTGCCTTCAGTATCTTCAGCAGTGTCCATTTGAAGATCATGTAAAATTAGTGA
ATGAAGTAACTGAATTTGCAAAAACATGTGTTGCTGATGAGTCAGCTGAAAATTGTGACAAATCACTTCATACCCTTTTTGGAGACAAATTATGCACA
GTTGCAACTCTTCGTGAAACCTATGGTGAAACTGCTGACTGCTGTGTGCAAAAACAAGAAACCTGAGAGAATGAATGCTTCTTGCAACACAAAGATGACAA
CCCAAACCTGCCCCCGATTGGTGAGACCAGAGGTTGATGTGAATCCCTTTCTTGCTAAAAGGTATAAAGCTGTTTTACAGAATGTTGCCAAGCTGCTGATAAA
TTGCCAGAAGACATCCTTACTTTTATGCCCAAAGCTGAAGCTTCGGGATGAACTTCGGGATGAACTTCGGGATGAAGGCTTCCCAAAGCTGTGCTCCTCTCCAAAATTTTGG
GCTGCCTGCTGTTGCCAAAGCTTTCAAAGCATGGCCATGCTGCCATGGAGATCGCTGCTTGAAATGTGCTGATGACAGGGCCGACAGTTTGCCAAGTTAGTGACAGATCTTACCA
AGAAAGAGCTTTCAACGGAATGCTGCCATGGAGATCGCTGCTTGAAATGTGCTGATGACAGGGCCGACAGTTTGCCAAGTATATCTGTGAAAATCAAGATTCGATCTCC
AGTAAACTGAAGGAATGCTGTGAAAGTAAGGATGTTTGCAAAAACTATGCTGAGGCAAGGATGTCTTCCTGGGCATGTTTTTGTATGAATATGCAAGAAGGC
ATCCTGATTACTCTGTCGTCGTCGATGAATTAAACCTCTTGGAAGAGACCTCCAAGACATATGAAACCACTCTAGAGAAGTGCTGTGCCGCTGCAGATCCTCATGAATGCTAT
GCCAAAGTGTTCGATGAATTTAAACCTCTTGTTACACCAAGAAAGTACCCCCAAGTGTCAACTCTCTTGTAGAGTCTCAAGAAACCTAGGAAAAGTGGGCAGCA
AATGTTGTAAACATCCTGAAGCAAAATGCTGCACAGAATCCTTGGTGACACAGGCGACCATGCTTTCTGAGAAGGAGACAAATCAAGAAACAAACTGCACTTGTTGAGCTCGTGA
GTAAGTGACAGAGTCACCAACATTGAACCTTCACCTTCATGCAACTGCAACTGAAACTGTTTATGGATGATTTCGCAGCTGTTTGTAGAGGCGGTAGCGGCGGTCGCTGCTGCTGCTGCTGCTGCTGACGAGACC
GTTTAATGCTGAAAACATTCACCTTCACTCTCATGCAACTGCAACTGAAAGCTGTTTATGGATGATTTCGCAGCTGTTTGTAGAGGCGGTAGCGGCGGTCGCTGCTGCTGCTGCTGCTGACGAGACC
AACACAAGCCCAAGGCCAACAAAAGAGCAACTGAAAACTTGTTGCTGCAAGTCAAGCTGCCTTAGGTGGAGCGGTAGCGGTAGCGGCGGTCGCTGGAGAACCTGGGCTGGGCCGATTGGG
TGCTTTGCCGAGGAGGTAAAAAACTTGTTGCTGCAAGTCAAGCTGCCTTAGGTGGAGCGGTAGCGGCGGTCGCTGGAGAACCTGGGCTGGGCCGATTGGG
GGCGGGTAACGGGGATCACTGTCCGGGAGTGCAAGTGACCATGTCCATCGGCCGTGCCCAGCCAGTTCCGGGCGGCAAACATGCACCGCCAGATCAAGACGAGCCTG
TGCTGTCGCCAACGGAGTGCCACACGGCCCGCGCTGCCCGCCAGCTACAATCCCATGGTGCTCATTCAAAAGACCGACACCGGGGTGTCGCT
CACCGCCTGAAGCCCTGATGATGACTTGTTAGCCAAAGACTGCCACTGCATATAA
```

Figure 1F

Fusion Molecule Comprising Mature HSA Amino Acid Sequence Fused to the N-Terminus of Mature Human GDF15 Amino Acid Sequence Through a Protease-sensitive Cleavable Linker (SEQ ID NO:13)

DAHKSEVAHRFKDLGEENFKALVLIAFAQYLQQCPFEDHVKLVNEVTEFAKTCVADESAENCDKSLHTLFGDKLCTVATLRETYGEMADCCAKQEPER
NECFLQHKDDNPNLPRLVRPEVDVMCTAFHDNEETFLKKYLYEIARRHPYFYAPELLFFAKRYKAAFTECCQAADKAACLLPKLDELRDEGKASSAKQ
RLKCASLQKFGERAFKAWAVARLSQRFPKAEFAEVSKLVTDLTKVHTECCHGDLLECADDRADLAKYICENQDSISSKLKECCEKPLLEKSHCIAEVE
NDEMPADLPSLAADFVESKDVCKNYAEAKDVFLGMFLYEYARRHPDYSVVLLLRLAKTYETTLEKCCAAADPHECYAKVFDEFKPLVEEPQNLIKQNC
ELFEQLGEYKFQNALLVRYTKKVPQVSTPTLVEVSRNLGKVGSKCCKHPEAKRMPCAEDYLSVVLNQLCVLHEKTPVSDRVTKCCTESLVNRRPCFSA
LEVDETYVPKEFNAETFTFHADICTLSEKERQIKKQTALVELVKHKPKATKEQLKAVMDDFAAFVEKCCKADDKETCFAEEGKKLVAASQAALGLGGG
GSGGGGSIEGRARNGDHCPLGPGRCCRLHTVRASLEDLGWADWVLSPREVQVTMCIGACPSQFRAANMHAQIKTSLHRLKPDTVPAPCCVPASYNPMV
LIQKTDTGVSLQTYDDLLAKDCHCI

Figure 1F, continued

Nucleic Acid Encoding A Fusion Molecule Comprising Mature HSA Amino Acid Sequence Fused to the N-Terminus of Mature Human GDF15 Amino Acid Sequence Through a Protease-sensitive Cleavable Linker (SEQ ID NO:14)

```
GATGCACACAAGAGTGAGGTTGCTCATCGGTTGCTCTTAAAGATTTGGGAGAAGAAAATTTCAAAGCCTTGGTGTTGATTGCCTTTGCTCAGTATCTTCAGCA
GTGTCCATTGAAGATCATGTAAAATTAGTGAATGAAGTAACTGAATTTGCAAAAACATGTGTTGCTGATGAGTCAGCTGAAAATTGTGACAAATCAC
TTCATACCCTTTTTGGAGACAAATTATGCACAGTTGCAACTCTTCGTGAAACCTATGGTGAAATGGCTGACTGCTGTGCAAAACAAGAACCTGAGAGA
AATGAATGCTTCTTGCAACAAAAGATGACAACCCAAACCCTCCCCCGATTGGTGAGACCAGAGGTTGATGTGATGTGCACTGCTTTTCATGACAATGA
AGAGACATTTTTGAAAAATGTGCCAAGCTGCTGATAAAGCTGCTGATGATAAAGCTGCTGATAACCTCGGATGAACTTCGGATGAACTTCGGATGAAGGAAGCTTCGTCTGCCAAACAG
CTTTTACAGAATGTGCCAGTCTCCAAAAATTTGGAGAAAGAGCTTTCAAAGCATGGCAGTAGCTCGCCTGAGCCAGAGATTTCCCAAAGCTGAGTTTGC
AGACTCAAGTGTGCCAGTCTCCAAAAATTTGGAGAAAGAGCTTTCAAAGCATGGCAGTAGCTCGCCTGAGCCAGAGATTTCCCAAAGCTGAGTTTGC
AGAAGTTTCCAAGTTAGTGACAGATCTTACCAAAGTCCACAGATTCGATCTGCCTTGCCATGGAGATCTGCTTGATGACAGGGCGGACCTTGCCA
AGTATATCTGTGAAAATCAAGATTCGATCTGCCTTCATTAGCTGCTGATTTGTTGAAAAGTAAGGATGTTTGCAAAAACTATGCTGAGGCAAAGGATGTCTTCCT
AATGATGAGATGCCTGCTGATGAATATGCAAGAAGGCATCCTGATTACTCGTGCTGATGAATTTAAACCTCTTGTGCTGGAAGACTTGCCAAGACATATGAAACCACTCTAGAGAAGT
GGGCATGTTTTTGTATGAATATGCAAGAAGGCATCCTGATTACTCGTGCTGATGAATTTAAACCTCTTGTGGAAGAGCCTCAGATTTCAATCAAACAAATTGT
GCTGTGCCGCTGCAGATCCTCATGAATGCTATGCCAAAGTGTTCGATGAGTACAAATTCCAGATTGCGCTATTAGTTCGTTACACCAAGAAAGTACCCCAAGTGTCAACTCCAACTCTTGTAGA
GAGCTTTTTGAGCAGCTTGGAGAGTACAAATTCCAGATTGCGCTATTAGTTCGTTACACCAAGAAAGTACCCCAAGTGTCAACTCCAACTCTTGTAGA
GGTCTCAAGAAACCTAGGAGAAAGTGGGCAGCAAATGTGTAAACATCCTGAAGCAAAATGTTGTAAACATCCTGAAGCAAAATGCTCACAGAATCCTTGTGAACAGGCGACCATGCTTTTCAGCT
ACCAGTTATGTGTTGCATGAGAAACGCCAGTAAGTGACAGAGTCACCAAACATTCTGAAACATTCCATGCAACAATGAAAGCTGTTATGCAAGTCGTTATGATGATGATGATTCGAGCTTTTGTAG
CTGGAAGTCGATGAAACATACGTTCCAAAGAGTTTAATGCTGAAACACACAAGCCAAGCAACAAAGAGCAACTGAAGCTGTTATGCAAGTCGTTATGATGATGATGATTCGAGCTTTTGTAG
CAAGAAACAAACTGCACTTGTTGAGCTCGTGAAACACAAGCCAAGCAACAAAGAGCAACTGAAGCTGTTATGCAAGTCGTTATGATGATGATGATTCGAGCTTTTGTAG
AGAAGTGCTGCAAGGCTGACGATAAGGAGACCTGCTTTGCCGAGGAGGGTAAAAAACTTGTTGCTGCAAGTCAAGCTGCCTTAGGCTTAGGTGGAGGC
GGTAGCGGTGGAGGTGGAAGACCTGGGCTGGGCGATTGGGTGCTGTCGCCACCGCCGATTCGCCTCCGCGTAACGGTGATCACGGGGATGCTGTCGCCACCGCCGATTCGCCTCCGCGTAACGTCGTCCGCGC
GTCGCTGGAGGTGGAAGACCTGGGCTGGGCGATTGGGTGCTGTCGCCACCGCCGATTCGCCTCCGCGTAACGGTGATCACGGGGATGCTGTCGCCACCGCCGATTCGCCTCCGCGTAACGTCGTCCGCGC
CAAACATGCACCGCCAGATCAAGACGAGCCTGCACCGCCTGAAGCCCGACACGGTGCCGACGGTGCATCGCGCCGACCGACTCGGCCACCGACTCGGCCCAGTCCATCCCATGGTG
CTCATTCAAAAGACCGACACCGGGGTGTCGCTCCAGACCTATGATGACTTGTTAGCCAAGACTGCCACTGCATATAA
```

Figure 1G

Fusion Molecule Comprising HSA Amino Acid Sequence Having an IgK Signal Sequence Fused to the N-Terminus of Mature Human GDF15 Amino Acid Sequence Through a Non-cleavable Linker (SEQ ID NO:15)

MDMRVPAQLLGLLLLWLRGARCDAHKSEVAHRFKDLGEENFKALVLIAFAQYLQQCPFEDHVKLVNEVTEFAKTCVADESAENCDKSLHTLFGDKLCT
VATLRETYGEMADCCAKQEPERNECFLQHKDDNPNLPRLVRPEVDVMCTAFHDNEETFLKKYLYEIARRHPYFYAPELLFFAKRYKAAFTECCQAADK
AACLLPKLDELRDEGKASSAKQRLKCASLQKFGERAFKAWAVARLSQRFPKAEFAEVSKLVTDLTKVHTECCHGDLLECADDRADLAKYICENQDSIS
SKLKECCEKPLLEKSHCIAEVENDEMPADLPSLAADFVESKDVCKNYAEAKDVFLGMFLYEYARRHPDYSVVLLLRLAKTYETTLEKCCAAADPHECY
AKVFDEFKPLVEEPQNLIKQNCELFEQLGEYKFQNALLVRYTKKVPQVSTPTLVEVSRNLGKVGSKCCKHPEAKRMPCAEDYLSVVLNQLCVLHEKTP
VSDRVTKCCTESLVNRRPCFSALEVDETYVPKEFNAETFTFHADICTLSEKERQIKKQTALVELVKHKPKATKEQLKAVMDDFAAFVEKCCKADDKET
CFAEEGKKLVAASQAALGLGGGGSGGGGSGGGGSARNGDHCPLGPGRCCRLHTVRASLEDLGWADWVLSPREVQVTMCIGACPSQFRAANMHAQIKTS
LHRLKPDTVPAPCCVPASYNPMVLIQKTDTGVSLQTYDDLLAKDCHCI

Figure 1G, continued

Nucleic Acid Encoding A Fusion Molecule Comprising HSA Amino Acid Sequence Having an IfK Signal Sequence Fused to the N-Terminus of Mature Human GDF15 Amino Acid Sequence Through a Non-cleavable Linker (SEQ ID NO:16)

```
ATGGACATGAGGGTCCCCGCTCAGCTCCTGGGGCTCCTGCTACTCTGCTTCCTGAGCTGCCAGATGTGATGCACACAAGAGTGAGGTTGCTCATCGTT
TAAAGATTTGGGAGGAAGAAATTTCAAAGCCTTGGTGTTGATGAGTAGTGCCAGTATCTTCAGCAGTGTCCATTTGAAGATCATGTAAAATTAGTGA
ATGAAGTAACTGAATTTGCAAAAACATGTGTTGCTGATGAGTCAGCTGAAAATTGTGACAAATCACTTCATACCCTTTTTGGAGACAAATTATGCACA
GTTGCAACTCTTCGTGAACTTATGGTGAAATGCTGACTGCTGTGCAAAACAAGAACCTGAGAGAAATGAATGCTTCTTGCAACACAAAGATGACAA
CCCAAACCTCCCCGATTGGTGAGACCAGAGGTTGATGTGATGCACTGCTTTTCATGACAATGAAGAGACATTTTTGAAAAAATACTTATATGAAA
TTGCCAGAAGACATCCTTACTTTTATGCCCGGAACTCTCTTTCTTTGCTAAAAGTATAAAGCTGCTTTTACAGAATGTTGCCAAGCTGCTGATAAA
GCTGCCTGCCTGTTGCCAAAGCTCGATGAACTCGGGATGAACTTCGGGATGAAGGGAAGGCTTCGTCTGCCAAACAGAGACTCAAGTGTGCCAGTCTCCAAAATTTGG
AGAAAGAGCTTTCAAAGCATGGGCAGTAGCTCGCCTGAGCTGCTTGATGAGCTGGAATGTGCTGATGACAGGGCGGACCTTGCCAAGAGTTGCCAAGAGTTCCAAGTTAGTGACAGATCTTACCA
AAGTCCACACGGAATGCTGCCATGGAGATCTGCTTGTTGCAAAAATCCCACTGCATTGCCGAAGTGGAAAATGATGAGATGCCTGCTGCTGATTCAAGATTCAAGATTCGATCTCC
AGTAAACTGAAGGAATGCTGTGAAAGTAAGGATGTTTGCAAAGATTGATTCTGCTGCTGAGACTTGCCCAAGAGCCTGAGGCAAGGATGCTCTTCCTGGAGCAAGGATGCTGTGCCGCTGCAGATCCTCATGAATGCTAT
ATCCTGATTACTCTGTCGTGCTGCTGATGAATTAACCTCTTGTGGAAGAGCCTCAGAATTGAAGACCTCAGAAGTGTGAGCTTTTTGAGCAGCTTGGAGAGTACAAATT
GCCAAAGTGTTCGATGAATTAAACCTCTTGTGGAAGAAATAGCCCGTGACAAAAGAATGGCCCTGTGCAGCAAAAGAATGCCCTGTGCAGAAAGAATCTGTGTCCTGAAACCAGTTATGTGTTGCATGAGAAAACGCCA
GTAAGTGACAGATGTCACCAACAATTCAGCTTCCATGCACAGCTGTGAAGCGCAAACAGGAACATCCTTGGTGACAGGAATCGGGCACGACCATCCTTGCTGCTGCTGTTTTCAGGCTCTGGAAGTGCAGTGCGAGATGAAACATACGTTCCCCAAGA
GTTTAATGCTGAAACATTCACCTTCCATGCACAACTGAAAGCTGTGCCATTTCAGGCAATATCGAGGCAATACTTCTGTGAGACTGGGATTCTATGGATCTGGATGGATTTCGCAGCTTCGCAAGCTGCTGCAAGCTGACGATAAGGAGACC
AACACAAGCCCCAAGGCAACAAAGAGCCAACTTGTTGCTGTTAGCTCAAGCATAATCGAGCTAGCTGGTTTTGCAAGCTGCGTTAGCGTTAGGCTTAGGTGCCGTCTGCCACACACACGGTTCCCGCCGCGTGGAGGTGGTGGAGGTGG
TGCTTTGCCGGAGGGGTAACGGGATCACTGTCCGGTCCGCGGCGTGCGCGGGAACATGCACAGGACTGCAACTGATACCGGTGCCGCGGCGCTGCCGAAGACCTGGGCCTGGAAGGTTTCATGACGGTGCCTGATTCCCAAAACATGCACAAGACCGCAACTAGGCACGCAACTGATCCGGTTGCAATACGAGCTGCAGCAT
GAGTGCCGCAATGGGGATCACTGTCCGGTCCGGGGCGTTGCCTGCCCACACGGTCCGCCGCGTGCGAGACCTGGGCCTGGAAGACCTGGGCCTGGATT
GGGTGCTGTGCCACACGGGCCACACGGTGCAAGTGACCATGTGCATCGGCGGCCATGTCCGGGCCGGCAAACATGCACCGCCAGATCAAGACGAGC
CTGCACCGCTGAAGCCTGAAGCCTGCAAGCGTGCCGAGACGCGCTGCCGAGCCCTGCTCCGCGTGCCCCCCAGCTACAATCCCATGTGCTCATTCAAAGACCGACACCGGGTGTC
GCTCCAGACCTATGATGACTTGTTAGCCAAAGACTGCCACTGCATATAA
```

Figure 1H

Fusion Molecule Containing Mature HSA Amino Acid Sequence Fused to the N-Terminus of Mature Human GDF15 Amino Acid Sequence Through a Non-cleavable Linker (SEQ ID NO:17)

DAHKSEVAHRFKDLGEENFKALVLIAFAQYLQQCPFEDHVKLVNEVTEFAKTCVADESAENCDKSLHTLFGDKLCTVATLRETYGEMADCCAKQEPER
NECFLQHKDDNPNLPRLVRPEVDVMCTAFHDNEETFLKKYLYEIARRHPYFYAPELLFFAKRYKAAFTECCQAADKAACLLPKLDELRDEGKASSAKQ
RLKCASLQKFGERAFKAWAVARLSQRFPKAEFAEVSKLVTDLTKVHTECCHGDLLECADDRADLAKYICENQDSISSKLKECCEKPLLEKSHCIAEVE
NDEMPADLPSLAADFVESKDVCKNYAEAKDVFLGMFLYEYARRHPDYSVVLLLRLAKTYETTLEKCCAAADPHECYAKVFDEFKPLVEEPQNLIKQNC
ELFEQLGEYKFQNALLVRYTKKVPQVSTPTLVEVSRNLGKVGSKCCKHPEAKRMPCAEDYLSVVLNQLCVLHEKTPVSDRVTKCCTESLVNRRPCFSA
LEVDETYVPKEFNAETFTFHADICTLSEKERQIKKQTALVELVKHKPKATKEQLKAVMDDFAAFVEKCCKADDKETCFAEEGKKLVAASQAALGLGGG
GSGGGGSGGGGSARNGDHCPLGPGRCCRLHTVRASLEDLGWADWVLSPREVQVTMCIGACPSQFRAANMHAQIKTSLHRLKPDTVPAPCCVPASYNPM
VLIQKTDTGVSLQ TYDDLLAKDCHCI

Figure 1H, continued

Nucleic Acid Encoding Fusion Molecule Containing Mature HSA Amino Acid Sequence Fused to the N-Terminus of Mature Human GDF15 Amino Acid Sequence Through a Non-cleavable Linker (SEQ ID NO:18)

GATGCACACAAGAGTGAGGTTGCTCATCGGTTTAAAGATTTGGGAGAAGAAAATTTCAAAGCCTTGGTTGTTGATTGCCTTTGCTCAGTATCTTCAGCA
GTGTCCATTTGAAGATCATGTAAAATTAGTGAATGAAGTAACTGAATTTGCAAAAACATGTGTTGCTGATGAGTCAGCTGAAAATTGTGACAAATCAC
TTCATACCCTTTTTGGAGACAAATTATGCACAGTTGCAACTCTTCGTGAAACCTATGGTGAAATGGCTGACTGCTGTGCAAAACAAGAACCTGAGAGA
AATGAATGCTTCTTGCAACACACAAAGATGACAACCCAAACCTCCCCCGATTGGTGAGACCAGAGTTGATGTGATGTGCACTGCTTTCATGACAATGA
AGAGACATTTTTGAAAAAATACTTATGAAAATGTGCCAGATGTTGCCAAGCTGCTGATAAAGCTGTCGATGAACTTCGGGATGAAGGAAGGCTTCGTCTGCCAAACAG
CTTTTACAGAATGTTGCCAAGCTGCCAGTCTCCAAAAAATTGGAGAAGAGCTTCAAAGCATGGCAGTAGCTCGCCTGAGCCAGAGATTTCCAAAGCTGAGTTTGC
AGAAGTTCCAAGTTAGTGACAGATCTTACCAAAGTCCACACGAATGCTGCCATGGAGATCTGCTTGAATGTGCTGATGACAGGGCGACCTTGCCA
AGTATATCTGTGAAAATCAAGATTCGATCTCCAGTAAACTGCTGCCTTCATTAGCTGCTGATTTGTTGAAAGTAAGGATGTTTCAAAAAACTATGCTGAGGCAAGGATGTCTTCCT
AATGATGAGATGCCTGCTGAATGTTTTGTATGAATATGCAAGAAGGCATCCTGACTTGCCAAGACATATGAAACCACTCTAGAGAAGT
GGGCATGTTTTTGCCGCTGCAGATCCTCATGAGAGTCTATGCCAAAGTGTTCGATGAATTTAAACCTCTTGTGGAAGAGCTACCCCAAGTGTCAACTCCAACTCTTGTAGA
GCTGTGCCGCTGCAGATCCTCATGAGAGTCTATGCCAAAGTGTTCGATGAATTTAAACCTCTTGTGGAAGAGCTACCCCAAGTGTCAACTCCAACTCTTGTAGA
GAGCTTTTTGAGCAGCTTGGAGAGTACAAATTCCAGAATGCTGTTAAACATCCTGAAGCAAAAGAATGCCCTGTGCAGAAGACTATCTATCCGTGGTCCTGA
GGTCTCAAGAAACTAGGAGAAAGTGGGCAGCAAATGTGTAAACATCCTGAAGCAGAATCCTGGTGAACAGGCGACCATGCTTTTCAGCT
ACCAGTTATGTGTTGCATGAAACATACGTTGTGAGCTGTGAAACATTCACCTTCCATGCAGAAACTGCTGACCAGATATATGCACACTTCTGAGAAGGAGAGACAAAT
CTGGAAGTGCGATGAAACATGCTGAAAACATGCTGAAAACATTCACCTTCCATGCAGAAACTGCTGACCAGATATATGCACACTTCTGAGAAGGAGAGACAAAT
CAAGAAACAAACTGCACTTGTTGAGCTCGTGAAACACAAGCCCAAGGCAACACAAAGAGCAACTGAAAGCTGTTATGATGATTTCGCAGCTTTTGTAG
AGAAGTGCTGCAAGGCTGACGATAAGGAGACCTGCTTTGCCGAGGAGGGTAAAAAACTTGTTGCTGCAAGTCAAGCTGCCTTAGGCTTAGGTGGAGGC
GGTAGCGGTGGAGGTGGGAGTGGTGGAGGTGGCCGATTGGGTGCGTCGCCACCGGGATCACTGTCCCGTGCCACCGGTCCG
CGCGTCGCTGGAAGACCTGGGCGCAGATCAAGACGAGCCTGCGACCGCGAAGCCCGACACGGTGCCAAGTGACACCGTCATGTGCGCCCAGCCAGTTCCGGG
CGGCAAACATGCGCGCAGATCAAGACCCGGGCTGTCGACCGCTGTCGACCGCTGAAGCCCTGCCAGCCCTATGACTTGTTAGCCAAAGCTACAATCCCATG
GTGCTCATTCAAAGACCGACACCGGGGTGTCGCTCCAGACCTATGATGACTTGTTAGCCAAAGCTGCCACTGCATATAA

Figure 2A – Effect of a Single Acute Dose of a Fusion Molecule Comprising Mature HSA Fused to Mature Human GDF15 on Body Weight
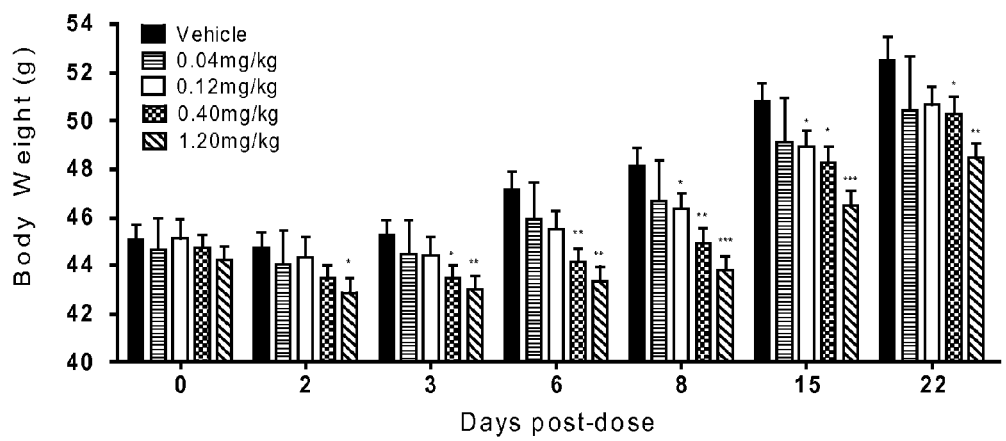
Figure 2B – Effect of a Single Acute Dose of a Fusion Molecule Comprising Mature HSA Fused to Mature Human GDF15 on Food Intake
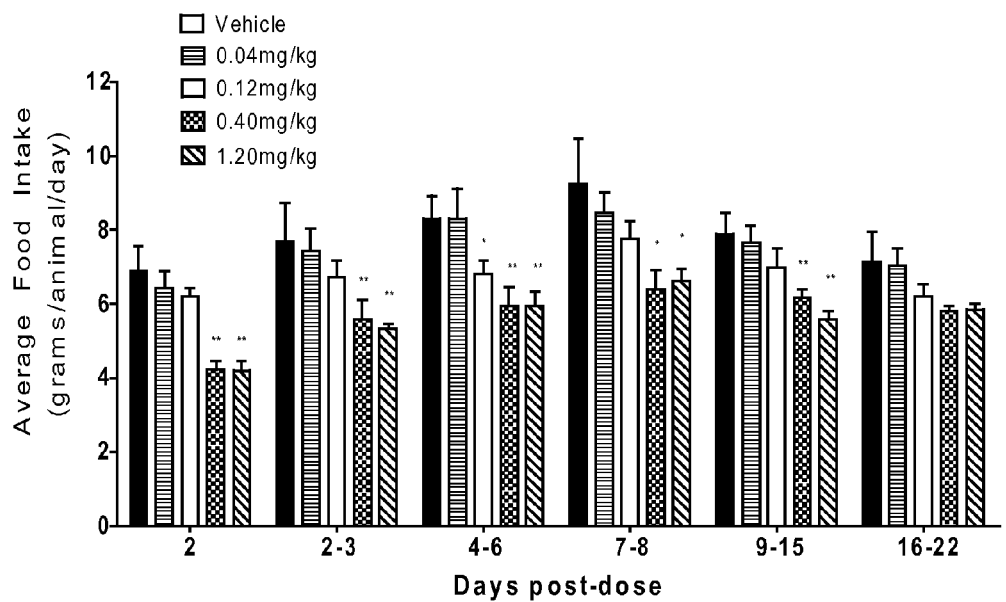

Figure 2C – Effect of a Single Acute Dose of a Fusion Molecule Comprising Mature HSA Fused to Mature Human GDF15 on Blood Glucose
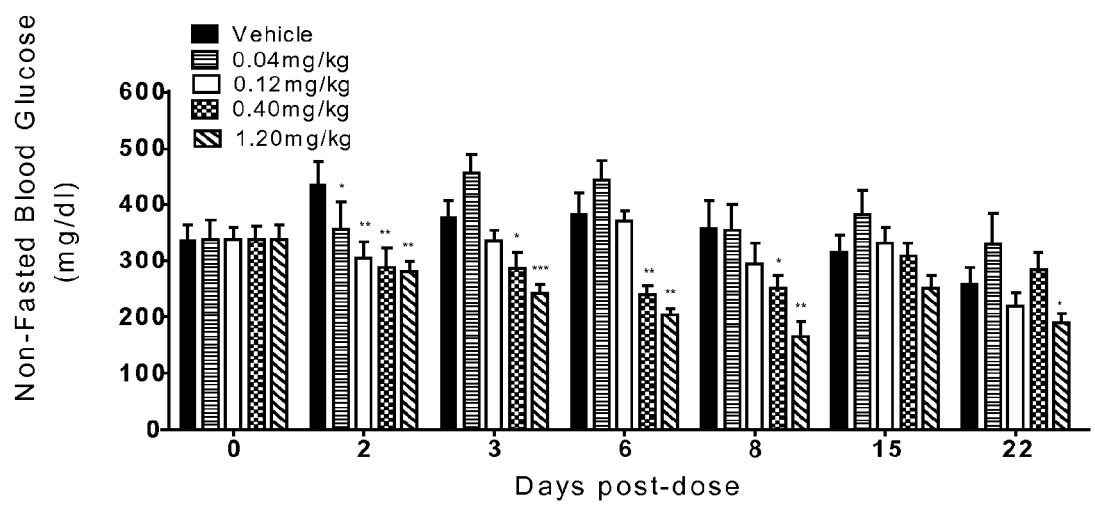

Figure 3 – GDF15 Muteins Generated by Alanine Mutagenesis

```
w29 -(SEQ ID NO:19):
ARNG DHCPLGPGRC CRLHTVRASL EDLGAADWVL SPREVQVTMC IGACPSQFRA
ANMHAQIKTS LHRLKPDTVP APCCVPASYN PMVLIQKTDT GVSLQTYDDL LAKDCHCI w32 -(SEQ ID NO:20):
ARNG DHCPLGPGRC CRLHTVRASL EDLGWADAVL SPREVQVTMC IGACPSQFRA
ANMHAQIKTS LHRLKPDTVP APCCVPASYN PMVLIQKTDT GVSLQTYDDL LAKDCHCI w52 -(SEQ ID NO:21):
ARNG DHCPLGPGRC CRLHTVRASL EDLGWADWVL SPREVQVTMC IGACPSQARA
ANMHAQIKTS LHRLKPDTVP APCCVPASYN PMVLIQKTDT GVSLQTYDDL LAKDCHCI w65 -(SEQ ID NO:22):
ARNG DHCPLGPGRC CRLHTVRASL EDLGWADWVL SPREVQVTMC IGACPSQFRA
ANMHAQIKTS AHRLKPDTVP APCCVPASYN PMVLIQKTDT GVSLQTYDDL LAKDCHCI w68 -(SEQ ID NO:23):
ARNG DHCPLGPGRC CRLHTVRASL EDLGWADWVL SPREVQVTMC IGACPSQFRA
ANMHAQIKTS LHRAKPDTVP APCCVPASYN PMVLIQKTDT GVSLQTYDDL LAKDCHCI w89 -(SEQ ID NO:24):
ARNG DHCPLGPGRC CRLHTVRASL EDLGWADWVL SPREVQVTMC IGACPSQFRA
ANMHAQIKTS LHRLKPDTVP APCCVPASYN PMVLAQKTDT GVSLQTYDDL LAKDCHCI
```

Figure 4 – Identification of GDF15 Mutein Residues for Assessment of Physical Properties

| Mutein | Residue | Mutein | Dimer |
|---|---|---|---|
| w29 | TRP | ALA | YES |
| w32 | TRP | ALA | YES |
| w52 | PHE | ALA | YES |
| w65 | LEU | ALA | NO |
| w68 | LEU | ALA | YES |
| w89 | ILE | ALA | YES |

Figure 5 – GDF15 Muteins for Evaluation of Physical Properties Relative to GDF15

```
w113 - (SEQ ID NO:25):
ARNG DHCPLGPGRC CRLHTVRASL AALGWAAWVL SPREVQVTMC IGACPSQFRA
ANMHAQIKTS LHRLKPDTVP APCCVPASYN PMVLIQKTDT GVSLQTYDDL
LAKDCHCI w114 - (SEQ ID NO:26):
ARNG DHCPLGPGRC CRLHTVRASL AALGWAAWVL SPRAVQVTMC IGACPSQFRA
ANMHAQIKTS LHRLKPDTVP APCCVPASYN PMVLIQKTDT GVSLQTYDDL LAKDCHCI w115 - (SEQ ID NO:27):
ARNG DHCPLGPGRC CRLHTVRASL EDLGWADWVL SPREVQVTMC IGACPSQFRA
ANMHAQIKTS LHRLKPDTVP APCCVPASYN PMVLIQKTDT GVSLQTYAAL LAKACHCI w116 - (SEQ ID NO:28):
ARNG DHCPLGPGRC CRLHTVRASL EDLGWADWVL SPREVQVTMC IGACPSQFRA
ANMHAQIKTS LHRLKPDTVP APCCVPASYN PMVLIQKTAT GVSLQTYAAL LAKACHCI w117 - (SEQ ID NO:29):
ARNG DHCPLGPGRC CRLHTVRASL EDLGWADWVL SPREVQVTMC IGACPSQFRA
ANMHAQIKTS LHRLKPDTVP APCCVPASYN PMVLIQKTAT GVSLQTYDDL LAKDCHCI
```

Figure 6 – Engineered N-Glycan Muteins for Evaluation of Improved Physical Properties Relative to GDF15 w118 - (SEQ ID NO:30):
ARNG THCPLGPGRC CRLHTVRASL EDLGWADWVL SPREVQVTMC IGACPSQFRA
ANMHAQIKTS LHRLKPDTVP APCCVPASYN PMVLIQKTDT GVSLQTYDDL LAKDCHCI w119 - (SEQ ID NO:31):
ARNG DHCPLGPGRC CRNHTVRASL EDLGWADWVL SPREVQVTMC IGACPSQFRA
ANMHAQIKTS LHRLKPDTVP APCCVPASYN PMVLIQKTDT GVSLQTYDDL LAKDCHCI w120 - (SEQ ID NO:32):
ARNG DHCPLGPGRC CRLHTVNASL EDLGWADWVL SPREVQVTMC IGACPSQFRA
ANMHAQIKTS LHRLKPDTVP APCCVPASYN PMVLIQKTDT GVSLQTYDDL LAKDCHCI w121 - (SEQ ID NO:33):
ARNG DHCPLGPGRC CRLHTVRASL EDLGWADWNL SPREVQVTMC IGACPSQFRA
ANMHAQIKTS LHRLKPDTVP APCCVPASYN PMVLIQKTDT GVSLQTYDDL LAKDCHCI w122 - (SEQ ID NO:34):
ARNG DHCPLGPGRC CRLHTVRASL EDLGWADWVL SPREVNVTMC IGACPSQFRA
ANMHAQIKTS LHRLKPDTVP APCCVPASYN PMVLIQKTDT GVSLQTYDDL LAKDCHCI w123 - (SEQ ID NO:35):
ARNG DHCPLGPGRC CRLHTVRASL EDLGWADWVL SPREVQVTMC IGACPSQFRA
ANMTAQIKTS LHRLKPDTVP APCCVPASYN PMVLIQKTDT GVSLQTYDDL LAKDCHCI w124 - (SEQ ID NO:36):
ARNG DHCPLGPGRC CRLHTVRASL EDLGWADWVL SPREVQVTMC IGACPSQFRA
ANMHAQNKTS LHRLKPDTVP APCCVPASYN PMVLIQKTDT GVSLQTYDDL LAKDCHCI w125 - (SEQ ID NO:37):
ARNG DHCPLGPGRC CRLHTVRASL EDLGWADWVL SPREVQVTMC IGACPSQFRA
ANMHAQINTS LHRLKPDTVP APCCVPASYN PMVLIQKTDT GVSLQTYDDL LAKDCHCI w126 - (SEQ ID NO:38):
ARNG DHCPLGPGRC CRLHTVRASL EDLGWADWVL SPREVQVTMC IGACPSQFRA
ANMHAQIKTS LHRLKNDTVP APCCVPASYN PMVLIQKTDT GVSLQTYDDL LAKDCHCI w127 - (SEQ ID NO:39):
ARNG DHCPLGPGRC CRLHTVRASL EDLGWADWVL SPREVQVTMC IGACPSQFRA
ANMHAQIKTS LHRLKPDTVP APCCVNASYN PMVLIQKTDT GVSLQTYDDL LAKDCHCI w128 - (SEQ ID NO:40):
ARNG DHCPLGPGRC CRLHTVRASL EDLGWADWVL SPREVQVTMC IGACPSQFRA
ANMHAQIKTS LHRLKPDTVP APCCVPASYN PMVLINKTDT GVSLQTYDDL LAKDCHCI w129 - (SEQ ID NO:41):
ARNG DHCPLGPGRC CRLHTVRASL EDLGWADWVL SPREVQVTMC IGACPSQFRA
ANMHAQIKTS LHRLKPDTVP APCCVPASYN PMVLIQKNDT GVSLQTYDDL LAKDCHCI

Figure 6 cont.

w130 - (SEQ ID NO:42):
ARNG DHCPLGPGRC CRLHTVRASL EDLGWADWVL SPREVQVTMC IGACPSQFRA
ANMHAQIKTS LHRLKPDTVP APCCVPASYN PMVLIQKTDT NVSLQTYDDL LAKDCHCI w131 - (SEQ ID NO:43):
ARNG DHCPLGPGRC CRLHTVRASL EDLGWADWVL SPREVQVTMC IGACPSQFRA
ANMHAQIKTS LHRLKPDTVP APCCVPASYN PMVLIQKTDT GVSNQTYDDL LAKDCHCI w132 - (SEQ ID NO:44):
ARNG THCPLGPGRC CRLHTVRASL EDLGWADWVL SPREVQVTMC IGACPSQFRA
ANMHAQIKTS LHRLKPDTVP APCCVPASYN PMVLINKTDT GVSLQTYDDL LAKDCHCI w133 - (SEQ ID NO:45):
ARNG THCPLGPGRC CRLHTVRASL EDLGWADWVL SPREVQVTMC IGACPSQFRA
ANMHAQIKTS LHRLKPDTVP APCCVPASYN PMVLIQKTDT NVSLQTYDDL LAKDCHCI w134 - (SEQ ID NO:46):
ARNG DHCPLGPGRC CRLHTVRASL EDLGWADWVL SPREVNVTMC IGACPSQFRA
ANMHAQIKTS LHRLKPDTVP APCCVPASYN PMVLINKTDT GVSLQTYDDL LAKDCHCI w135 - (SEQ ID NO:47):
ARNG DHCPLGPGRC CRLHTVRASL EDLGWADWVL SPREVNVTMC IGACPSQFRA
ANMHAQIKTS LHRLKPDTVP APCCVPASYN PMVLIQKTDT NVSLQTYDDL LAKDCHCI w136 - (SEQ ID NO:48):
ARNG DHCPLGPGRC CRLHTVRASL EDLGWADWVL SPREVQVTMC IGACPSQFRA
ANMHAQIKTS LHRLKNDTVP APCCVPASYN PMVLINKTDT GVSLQTYDDL LAKDCHCI w137 - (SEQ ID NO:49):
ARNG DHCPLGPGRC CRLHTVRASL EDLGWADWVL SPREVQVTMC IGACPSQFRA
ANMHAQIKTS LHRLKNDTVP APCCVPASYN PMVLIQKTDT NVSLQTYDDL LAKDCHCI w138 - (SEQ ID NO:50):
ARNG DHCPLGPGRC CRLHTVRASL EDLGWADWVL SPREVQVTMC IGACPSQFRA
ANMHAQIKTS LHRLKPDTVP APCCVPASYN PMVLINKTDT NVSLQTYDDL LAKDCHCI w139 - (SEQ ID NO:51):
ARNG DHCPLGPGRC CRLHTVRASL EDLGWADWVL SPREVQVTMC IGACPSQFRA
ANMHAQIKTS LHRLKPDTVP APCCVPASYN PMVLINKTDT GVSNQTYDDL LAKDCHCI w140 - (SEQ ID NO:52):
ARNG DHCPLGPGRC CRLHTVRASL EDLGWADWVL SPREVQVTMC IGACPSQFRA
ANMHAQIKTS LHRLKPDTVP APCCVPASYN PMVLIQKTDT NVSNQTYDDL LAKDCHCI

Figure 7 – Human GDF15 Mutein Dimer Formation and N-Glycan Site Occupancy

| Mutein | Dimer | N-Glyc |
|---|---|---|
| w118 | YES | YES |
| w119 | YES | YES |
| w120 | YES | YES |
| w121 | YES | NO |
| w122 | YES | YES |
| w123 | NO | - |
| w124 | YES | NO |
| w125 | NO | - |
| w126 | YES | YES |
| w127 | NO | - |
| w128 | YES | YES |
| w129 | NO | - |
| w130 | YES | YES |
| w131 | YES | YES |
| w132 | YES | YES |
| w133 | YES | YES |
| w134 | YES | YES |
| w135 | YES | YES |
| w136 | YES | YES |
| w137 | YES | YES |
| w138 | YES | YES |
| w139 | YES | YES |
| w140 | YES | YES |

Figure 8 – Maximum Solubility of Human GDF15 Muteins

| Mutein | Max solubility in PBS |
|---|---|
| hGDF15 | + |
| w29 | + |
| w32 | + |
| w52 | ++ |
| w68 | + |
| w89 | ++ |
| w113 | + |
| w115 | + |
| w116 | ++ |
| w118 | +++ |
| w120 | ++++ |
| w122 | ++ |

| Mutein | Max solubility in PBS |
|---|---|
| w126 | +++ |
| w128 | ++++ |
| w130 | ++++ |
| w131 | ++++ |
| w132 | ++++ |
| w133 | ++++ |
| w134 | ++++ |
| w135 | +++++ |
| w136 | ++++ |
| w137 | ++++ |
| w138 | +++++ |
| w139 | +++++ |
| w140 | +++++ |

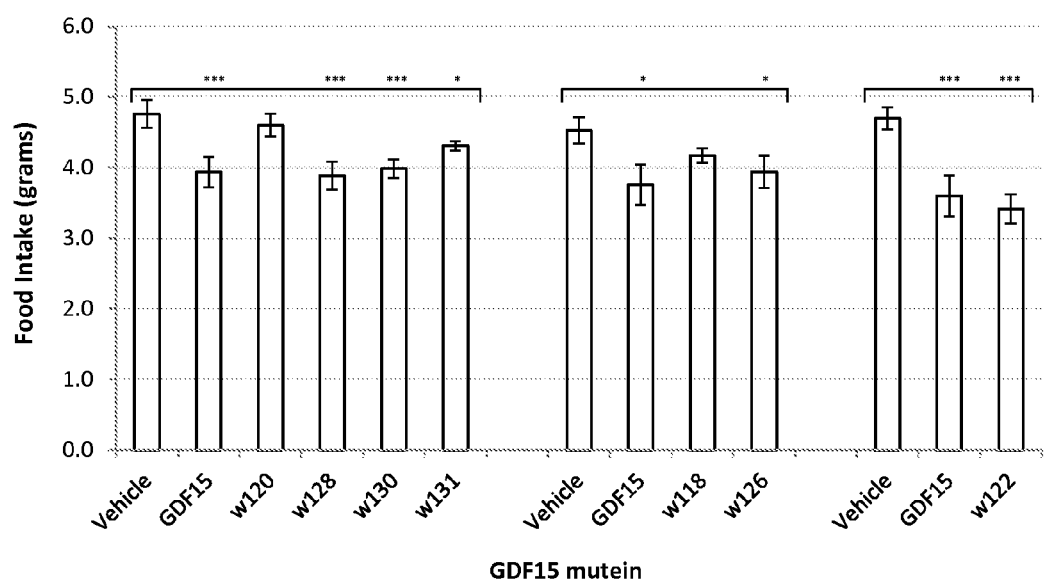
Figure 9 – Acute in vivo Efficacy of Human GDF15 N-Glycan Muteins on Food Intake Figure 10 – Analytical Gel Filtration of N-Glycan Muteins and Mature Human GDF15

| Mutein | Elution time (min) |
|---|---|
| hGDF15 | 10.837 |
| w118 | 10.029 |
| w120 | 9.201 |
| w122 | 9.123 |
| w126 | 10.011 |
| w128 | 9.854 |
| w130 | 9.198 |
| w131 | 9.153 |
| w132 | 9.342 |
| w133 | 8.810 |
| w134 | 8.967 |
| w135 | 8.667 |
| w136 | 9.787 |
| w138 | 9.221 |
| w139 | 9.281 |

SEQUENCE LISTING

```
<160> NUMBER OF SEQ ID NOS: 89

<210> SEQ ID NO 1
<211> LENGTH: 308
<212> TYPE: PRT
<213> ORGANISM: Homo sapiens

<400> SEQUENCE: 1

Met Pro Gly Gln Glu Leu Arg Thr Val Asn Gly Ser Gln Met Leu Leu
1               5                   10                  15

Val Leu Leu Val Leu Ser Trp Leu Pro His Gly Gly Ala Leu Ser Leu
                20                  25                  30

Ala Glu Ala Ser Arg Ala Ser Phe Pro Gly Pro Ser Glu Leu His Ser
            35                  40                  45

Glu Asp Ser Arg Phe Arg Glu Leu Arg Lys Arg Tyr Glu Asp Leu Leu
        50                  55                  60

Thr Arg Leu Arg Ala Asn Gln Ser Trp Glu Asp Ser Asn Thr Asp Leu
65                  70                  75                  80

Val Pro Ala Pro Ala Val Arg Ile Leu Thr Pro Glu Val Arg Leu Gly
                85                  90                  95

Ser Gly Gly His Leu His Leu Arg Ile Ser Arg Ala Ala Leu Pro Glu
                100                 105                 110

Gly Leu Pro Glu Ala Ser Arg Leu His Arg Ala Leu Phe Arg Leu Ser
            115                 120                 125

Pro Thr Ala Ser Arg Ser Trp Asp Val Thr Arg Pro Leu Arg Arg Gln
        130                 135                 140

Leu Ser Leu Ala Arg Pro Gln Ala Pro Ala Leu His Leu Arg Leu Ser
145                 150                 155                 160

Pro Pro Pro Ser Gln Ser Asp Gln Leu Leu Ala Glu Ser Ser Ser Ala
                165                 170                 175

Arg Pro Gln Leu Glu Leu His Leu Arg Pro Gln Ala Ala Arg Gly Arg
            180                 185                 190

Arg Arg Ala Arg Ala Arg Asn Gly Asp His Cys Pro Leu Gly Pro Gly
        195                 200                 205

Arg Cys Cys Arg Leu His Thr Val Arg Ala Ser Leu Glu Asp Leu Gly
        210                 215                 220

Trp Ala Asp Trp Val Leu Ser Pro Arg Glu Val Gln Val Thr Met Cys
225                 230                 235                 240
```

```
Ile Gly Ala Cys Pro Ser Gln Phe Arg Ala Ala Asn Met His Ala Gln
                245                 250                 255

Ile Lys Thr Ser Leu His Arg Leu Lys Pro Asp Thr Val Pro Ala Pro
            260                 265                 270

Cys Cys Val Pro Ala Ser Tyr Asn Pro Met Val Leu Ile Gln Lys Thr
        275                 280                 285

Asp Thr Gly Val Ser Leu Gln Thr Tyr Asp Asp Leu Leu Ala Lys Asp
    290                 295                 300

Cys His Cys Ile
305

<210> SEQ ID NO 2
<211> LENGTH: 1220
<212> TYPE: PRT
<213> ORGANISM: Homo sapiens

<400> SEQUENCE: 2

Ala Gly Thr Cys Cys Ala Gly Cys Thr Cys Ala Gly Ala Gly Cys
1               5                   10                  15

Cys Gly Cys Ala Ala Cys Cys Thr Gly Cys Ala Cys Ala Gly Cys Cys
                20                  25                  30

Ala Thr Gly Cys Cys Gly Gly Cys Ala Ala Gly Ala Ala Cys
            35                  40                  45

Thr Cys Ala Gly Gly Ala Cys Gly Gly Thr Gly Ala Ala Thr Gly Gly
    50                  55                  60

Cys Thr Cys Thr Cys Ala Gly Ala Thr Gly Cys Thr Cys Cys Thr Gly
65                  70                  75                  80

Gly Thr Gly Thr Thr Gly Cys Thr Gly Gly Thr Gly Cys Thr Cys Thr
                85                  90                  95

Cys Gly Thr Gly Gly Cys Thr Gly Cys Cys Gly Cys Ala Thr Gly Gly
            100                 105                 110

Gly Gly Gly Cys Gly Cys Cys Thr Gly Thr Cys Thr Cys Thr
        115                 120                 125

Gly Cys Cys Gly Ala Gly Gly Cys Gly Ala Gly Cys Cys Gly Cys Gly
    130                 135                 140

Cys Ala Ala Gly Thr Thr Thr Cys Cys Gly Gly Ala Cys Cys
145                 150                 155                 160

Cys Thr Cys Ala Gly Ala Gly Thr Thr Gly Cys Ala Cys Thr Cys Cys
                165                 170                 175

Gly Ala Ala Gly Ala Cys Thr Cys Cys Ala Gly Ala Thr Thr Cys Cys
            180                 185                 190

Gly Ala Gly Ala Gly Thr Thr Gly Cys Gly Gly Ala Ala Cys Gly
        195                 200                 205

Cys Thr Ala Cys Gly Ala Gly Gly Ala Cys Cys Gly Cys Thr Ala
    210                 215                 220

Ala Cys Cys Ala Gly Gly Cys Thr Gly Cys Gly Gly Cys Cys Ala
225                 230                 235                 240

Ala Cys Cys Ala Gly Ala Gly Cys Thr Gly Gly Ala Ala Gly Ala
                245                 250                 255

Thr Thr Cys Gly Ala Ala Cys Ala Cys Cys Gly Ala Cys Thr Cys
            260                 265                 270

Gly Thr Cys Cys Gly Gly Cys Cys Cys Thr Gly Cys Ala Gly
        275                 280                 285

Thr Cys Cys Gly Gly Ala Thr Ala Cys Thr Cys Ala Cys Gly Cys Cys
    290                 295                 300
```

```
Ala Gly Ala Ala Gly Thr Gly Cys Gly Gly Cys Thr Gly Gly Ala
305                 310                 315                 320
Thr Cys Cys Gly Gly Cys Gly Cys Cys Ala Cys Cys Thr Gly Cys
                325                 330                 335
Ala Cys Cys Thr Gly Cys Gly Thr Ala Thr Cys Thr Cys Thr Cys Gly
            340                 345                 350
Gly Gly Cys Cys Gly Cys Cys Thr Thr Cys Cys Gly Ala Gly
        355                 360                 365
Gly Gly Gly Cys Thr Cys Cys Cys Gly Ala Gly Gly Cys Cys Thr
        370                 375                 380
Cys Cys Cys Gly Cys Cys Thr Thr Cys Ala Cys Cys Gly Gly Gly Cys
385                 390                 395                 400
Thr Cys Thr Gly Thr Thr Cys Cys Gly Gly Cys Thr Gly Thr Cys Cys
                405                 410                 415
Cys Cys Cys Gly Ala Cys Gly Gly Cys Gly Thr Cys Ala Ala Gly Gly Thr
                420                 425                 430
Cys Gly Thr Gly Gly Gly Ala Cys Gly Thr Gly Ala Cys Ala Cys Gly
            435                 440                 445
Ala Cys Cys Gly Cys Thr Gly Cys Gly Gly Cys Gly Thr Cys Ala Gly
450                 455                 460
Cys Thr Cys Ala Gly Cys Cys Thr Thr Gly Cys Ala Ala Gly Ala Cys
465                 470                 475                 480
Cys Cys Cys Ala Gly Gly Cys Gly Cys Cys Gly Cys Gly Cys Thr
                485                 490                 495
Gly Cys Ala Cys Cys Thr Gly Cys Gly Ala Cys Thr Gly Thr Cys Gly
            500                 505                 510
Cys Cys Gly Cys Cys Gly Cys Cys Gly Thr Cys Gly Cys Ala Gly Thr
                515                 520                 525
Cys Gly Gly Ala Cys Cys Ala Ala Cys Thr Gly Cys Thr Gly Gly Cys
            530                 535                 540
Ala Gly Ala Ala Thr Cys Thr Thr Cys Gly Thr Cys Cys Gly Cys Ala
545                 550                 555                 560
Cys Gly Gly Cys Cys Cys Ala Gly Cys Thr Gly Gly Ala Gly Thr
                565                 570                 575
Thr Gly Cys Ala Cys Thr Thr Gly Cys Gly Gly Cys Cys Gly Cys Ala
            580                 585                 590
Ala Gly Cys Cys Gly Cys Cys Ala Gly Gly Gly Gly Cys Gly Cys Cys
        595                 600                 605
Cys Gly Cys Ala Gly Ala Gly Cys Gly Cys Gly Thr Gly Cys Gly Cys
        610                 615                 620
Gly Cys Ala Ala Cys Gly Gly Gly Ala Cys Cys Ala Cys Thr Gly
625                 630                 635                 640
Thr Cys Cys Gly Cys Thr Cys Gly Gly Cys Cys Cys Gly Gly Gly
                645                 650                 655
Cys Gly Thr Thr Gly Cys Thr Gly Cys Cys Gly Thr Cys Thr Gly Cys
            660                 665                 670
Ala Cys Ala Cys Gly Gly Thr Cys Cys Gly Cys Gly Thr Cys
            675                 680                 685
Gly Cys Thr Gly Gly Ala Ala Gly Ala Cys Thr Gly Gly Gly Cys
            690                 695                 700
Thr Gly Gly Gly Cys Cys Gly Ala Thr Thr Gly Gly Gly Thr Gly Cys
705                 710                 715                 720
```

-continued

```
Thr Gly Thr Cys Gly Cys Cys Ala Cys Gly Gly Ala Gly Gly Thr
            725                 730                 735
Gly Cys Ala Ala Gly Thr Gly Ala Cys Cys Ala Thr Gly Thr Cys
            740                 745                 750
Ala Thr Cys Gly Gly Cys Gly Cys Gly Thr Gly Cys Cys Gly Ala
            755                 760                 765
Gly Cys Cys Ala Gly Thr Thr Cys Cys Gly Gly Gly Cys Gly Gly Cys
            770                 775                 780
Ala Ala Ala Cys Ala Thr Gly Cys Ala Cys Cys Gly Cys Ala Gly
785                 790                 795                 800
Ala Thr Cys Ala Ala Gly Ala Cys Gly Ala Gly Cys Cys Thr Gly Cys
            805                 810                 815
Ala Cys Cys Gly Cys Cys Thr Gly Ala Ala Gly Cys Cys Gly Ala
            820                 825                 830
Cys Ala Cys Gly Gly Thr Gly Cys Cys Ala Gly Cys Gly Cys Cys Cys
            835                 840                 845
Thr Gly Cys Thr Gly Cys Gly Thr Gly Cys Cys Cys Gly Cys Cys Ala
            850                 855                 860
Gly Cys Thr Ala Cys Ala Ala Thr Cys Cys Ala Thr Gly Gly Thr
865                 870                 875                 880
Gly Cys Thr Cys Ala Thr Thr Cys Ala Ala Ala Gly Ala Cys Cys
            885                 890                 895
Gly Ala Cys Ala Cys Cys Gly Gly Gly Thr Gly Cys Gly Cys
            900                 905                 910
Thr Cys Cys Ala Gly Ala Cys Cys Ala Thr Gly Ala Thr Gly Ala
            915                 920                 925
Cys Thr Thr Gly Thr Thr Ala Gly Cys Cys Ala Ala Ala Gly Ala Cys
            930                 935                 940
Thr Gly Cys Cys Ala Cys Thr Gly Cys Ala Thr Ala Thr Gly Ala Gly
945                 950                 955                 960
Cys Ala Gly Thr Cys Cys Thr Gly Gly Thr Cys Cys Thr Thr Cys Cys
            965                 970                 975
Ala Cys Thr Gly Thr Gly Cys Ala Cys Cys Thr Gly Cys Gly Cys Gly
            980                 985                 990
Gly Ala Gly Gly Ala Cys Gly Cys Gly Ala Cys Cys Thr Cys Ala Gly
            995                 1000                1005
Thr Thr Gly Thr Cys Cys Thr Gly Cys Cys Cys Thr Gly Thr Gly
            1010                1015                1020
Gly Ala Ala Thr Gly Gly Gly Cys Thr Cys Ala Ala Gly Gly Thr
            1025                1030                1035
Thr Cys Cys Thr Gly Ala Gly Ala Cys Ala Cys Cys Cys Gly Ala
            1040                1045                1050
Thr Thr Cys Cys Thr Gly Cys Cys Cys Ala Ala Ala Cys Ala Gly
            1055                1060                1065
Cys Thr Gly Thr Ala Thr Thr Ala Thr Ala Thr Ala Ala Gly
            1070                1075                1080
Thr Cys Thr Gly Thr Thr Ala Thr Thr Thr Ala Thr Thr Ala Thr
            1085                1090                1095
Thr Ala Ala Thr Thr Ala Thr Thr Gly Gly Gly Thr Gly
            1100                1105                1110
Ala Cys Cys Thr Thr Cys Thr Thr Gly Gly Gly Gly Ala Cys Thr
            1115                1120                1125
```

```
Cys Gly Gly Gly Gly Gly Cys Thr Gly Gly Thr Cys Thr Gly Ala
    1130                1135                1140

Thr Gly Gly Ala Ala Cys Gly Thr Gly Thr Ala Thr Thr Thr
    1145                1150                1155

Ala Thr Thr Thr Ala Ala Ala Cys Thr Cys Thr Gly Gly Thr
    1160                1165                1170

Gly Ala Thr Ala Ala Ala Ala Thr Ala Ala Ala Gly Cys Thr
    1175                1180                1185

Gly Thr Cys Thr Gly Ala Ala Cys Thr Gly Thr Ala Ala Ala
    1190                1195                1200

Ala Ala Ala Ala Ala Ala Ala Ala Ala Ala Ala Ala Ala Ala
    1205                1210                1215

Ala Ala
    1220

<210> SEQ ID NO 3
<211> LENGTH: 112
<212> TYPE: PRT
<213> ORGANISM: Homo sapiens

<400> SEQUENCE: 3

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 4
<211> LENGTH: 339
<212> TYPE: DNA
<213> ORGANISM: Homo sapiens

<400> SEQUENCE: 4
gcgcgtaacg gggatcactg tccgctcggg cccgggcgtt gctgccgtct gcacacggtc    60
cgcgcgtcgc tggaagacct gggctgggcc gattgggtgc tgtcgccacg ggaggtgcaa   120
gtgaccatgt gcatcggcgc gtgcccgagc cagttccggg cggcaaacat gcacgcgcag   180
atcaagacga gcctgcaccg cctgaagccc gacacggtgc cagcgccctg ctgcgtgccc   240
gccagctaca atcccatggt gctcattcaa aagaccgaca ccggggtgtc gctccagacc   300
tatgatgact tgttagccaa agactgccac tgcatataa                          339

<210> SEQ ID NO 5
<211> LENGTH: 609
<212> TYPE: PRT
<213> ORGANISM: Homo sapiens
```

```
<400> SEQUENCE: 5

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
            85                  90                  95

Lys Leu Cys Thr Val Ala Thr Leu Arg Glu Thr Tyr Gly Glu Met Ala
        100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
            165                 170                 175

Glu Leu Leu Phe Phe Ala Lys Arg Tyr Lys Ala Ala Phe Thr Glu Cys
        180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
            245                 250                 255

Lys Leu Val Thr Asp Leu Thr Lys Val His Thr Glu Cys Cys His Gly
        260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
            325                 330                 335

Lys Asp Val Cys Lys Asn Tyr Ala Glu Ala Lys Asp Val Phe Leu Gly
        340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
            405                 410                 415
```

```
Glu Leu Phe Glu Gln Leu Gly Glu Tyr Lys Phe Gln Asn Ala Leu Leu
                420                 425                 430

Val Arg Tyr Thr Lys Lys Val Pro Gln Val Ser Thr Pro Thr Leu Val
            435                 440                 445

Glu Val Ser Arg Asn Leu Gly Lys Val Gly Ser Lys Cys Cys Lys His
        450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu

<210> SEQ ID NO 6
<211> LENGTH: 2264
<212> TYPE: DNA
<213> ORGANISM: Homo sapiens

<400> SEQUENCE: 6
agtatattag tgctaatttc cctccgtttg tcctagcttt tctcttctgt caaccccaca      60
cgcctttggc acaatgaagt gggtaacctt tatttccctt cttttctct ttagctcggc     120 ttattccagg ggtgtgtttc gtcgagatgc acacaagagt gaggttgctc atcggtttaa     180
agatttggga gaagaaaatt tcaaagcctt ggtgttgatt gcctttgctc agtatcttca     240
gcagtgtcca tttgaagatc atgtaaaatt agtgaatgaa gtaactgaat tgcaaaaac     300 atgtgttgct gatgagtcag ctgaaaattg tgacaaatca cttcataccc ttttttggaga    360 caaattatgc acagttgcaa ctcttcgtga acctatggt gaaatggctg actgctgtgc     420
aaaacaagaa cctgagagaa atgaatgctt cttgcaacac aaagatgaca acccaaacct     480
cccccgattg gtgagaccag aggttgatgt gatgtgcact gcttttcatg acaatgaaga     540 gacattttg aaaaaatact tatatgaaat tgccagaaga catccttact tttatgcccc      600
ggaactcctt ttctttgcta aaaggtataa agctgctttt acagaatgtt gccaagctgc     660
tgataaagct gcctgcctgt tgccaaagct cgatgaactt cgggatgaag ggaaggcttc     720
gtctgccaaa cagagactca gtgtgccag tctccaaaaa tttggagaaa gagcttcaa      780 agcatgggca gtagctcgcc tgagccagag atttcccaaa gctgagtttg cagaagtttc     840
caagttagtg acagatctta ccaaagtcca cacggaatgc tgccatggag atctgcttga     900
atgtgctgat gacagggcgg accttgccaa gtatatctgt gaaaatcaag attcgatctc     960
cagtaaactg aaggaatgct gtgaaaaacc tctgttggaa aaatcccact gcattgccga   1020
```

```
agtggaaaat gatgagatgc ctgctgactt gccttcatta gctgctgatt ttgttgaaag   1080
taaggatgtt tgcaaaaact atgctgaggc aaaggatgtc ttcctgggca tgttttttgta  1140 tgaatatgca agaaggcatc ctgattactc tgtcgtgctg ctgctgagac ttgccaagac   1200
atatgaaacc actctagaga agtgctgtgc cgctgcagat cctcatgaat gctatgccaa   1260
agtgttcgat gaatttaaac ctcttgtgga agagcctcag aatttaatca acaaaattg    1320 tgagcttttt gagcagcttg gagagtacaa attccagaat gcgctattag ttcgttacac   1380
caagaaagta ccccaagtgt caactccaac tcttgtagag gtctcaagaa acctaggaaa   1440
agtgggcagc aaatgttgta acatcctga agcaaaaaga atgccctgtg cagaagacta   1500
tctatccgtg gtcctgaacc agttatgtgt gttgcatgag aaaacgccag taagtgacag   1560
agtcaccaaa tgctgcacag aatccttggt gaacaggcga ccatgctttt cagctctgga   1620
agtcgatgaa acatacgttc ccaaagagtt taatgctgaa acattcacct tccatgcaga   1680
tatatgcaca ctttctgaga aggagagaca aatcaagaaa caaactgcac ttgttgagct   1740
cgtgaaacac aagcccaagg caacaaaaga gcaactgaaa gctgttatgg atgatttcgc   1800
agcttttgta gagaagtgct gcaaggctga cgataaggag acctgctttg ccgaggaggg   1860
taaaaaactt gttgctgcaa gtcaagctgc cttaggctta aacatcaca tttaaaagca    1920 tctcagccta ccatgagaat aagagaaaga aaatgaagat caaaagctta ttcatctgtt   1980 tttcttttc gttggtgtaa agccaacacc ctgtctaaaa aacataaatt tctttaatca    2040
ttttgcctct tttctctgtg cttcaattaa taaaaaatgg aaagaatcta atagagtggt   2100
acagcactgt tattttcaa agatgtgttg ctatcctgaa aattctgtag ttctgtgga    2160 agttccagtg ttctctctta ttccacttcg gtagaggatt tctagtttct tgtgggctaa   2220
ttaaataaat cattaatact cttctaaaaa aaaaaaaaa aaaa                     2264
```

<210> SEQ ID NO 7
<211> LENGTH: 607
<212> TYPE: PRT
<213> ORGANISM: Homo sapiens

<400> SEQUENCE: 7

```
Met Asp Met Arg Val Pro Ala Gln Leu Leu Gly Leu Leu Leu Leu Trp
1               5                   10                  15

Leu Arg Gly Ala Arg Cys Asp Ala His Lys Ser Glu Val Ala His Arg
            20                  25                  30

Phe Lys Asp Leu Gly Glu Glu Asn Phe Lys Ala Leu Val Leu Ile Ala
        35                  40                  45

Phe Ala Gln Tyr Leu Gln Gln Cys Pro Phe Glu Asp His Val Lys Leu
    50                  55                  60

Val Asn Glu Val Thr Glu Phe Ala Lys Thr Cys Val Ala Asp Glu Ser
65                  70                  75                  80

Ala Glu Asn Cys Asp Lys Ser Leu His Thr Leu Phe Gly Asp Lys Leu
                85                  90                  95

Cys Thr Val Ala Thr Leu Arg Glu Thr Tyr Gly Glu Met Ala Asp Cys
            100                 105                 110

Cys Ala Lys Gln Glu Pro Glu Arg Asn Glu Cys Phe Leu Gln His Lys
        115                 120                 125

Asp Asp Asn Pro Asn Leu Pro Arg Leu Val Arg Pro Glu Val Asp Val
    130                 135                 140

Met Cys Thr Ala Phe His Asp Asn Glu Glu Thr Phe Leu Lys Lys Tyr
145                 150                 155                 160
```

-continued

```
Leu Tyr Glu Ile Ala Arg Arg His Pro Tyr Phe Tyr Ala Pro Glu Leu
            165                 170                 175

Leu Phe Phe Ala Lys Arg Tyr Lys Ala Ala Phe Thr Glu Cys Cys Gln
        180                 185                 190

Ala Ala Asp Lys Ala Ala Cys Leu Leu Pro Lys Leu Asp Glu Leu Arg
    195                 200                 205

Asp Glu Gly Lys Ala Ser Ser Ala Lys Gln Arg Leu Lys Cys Ala Ser
210                 215                 220

Leu Gln Lys Phe Gly Glu Arg Ala Phe Lys Ala Trp Ala Val Ala Arg
225                 230                 235                 240

Leu Ser Gln Arg Phe Pro Lys Ala Glu Phe Ala Glu Val Ser Lys Leu
                245                 250                 255

Val Thr Asp Leu Thr Lys Val His Thr Glu Cys Cys His Gly Asp Leu
            260                 265                 270

Leu Glu Cys Ala Asp Asp Arg Ala Asp Leu Ala Lys Tyr Ile Cys Glu
        275                 280                 285

Asn Gln Asp Ser Ile Ser Ser Lys Leu Lys Glu Cys Cys Glu Lys Pro
    290                 295                 300

Leu Leu Glu Lys Ser His Cys Ile Ala Glu Val Glu Asn Asp Glu Met
305                 310                 315                 320

Pro Ala Asp Leu Pro Ser Leu Ala Ala Asp Phe Val Glu Ser Lys Asp
                325                 330                 335

Val Cys Lys Asn Tyr Ala Glu Ala Lys Asp Val Phe Leu Gly Met Phe
            340                 345                 350

Leu Tyr Glu Tyr Ala Arg Arg His Pro Asp Tyr Ser Val Val Leu Leu
        355                 360                 365

Leu Arg Leu Ala Lys Thr Tyr Glu Thr Thr Leu Glu Lys Cys Cys Ala
    370                 375                 380

Ala Ala Asp Pro His Glu Cys Tyr Ala Lys Val Phe Asp Glu Phe Lys
385                 390                 395                 400

Pro Leu Val Glu Glu Pro Gln Asn Leu Ile Lys Gln Asn Cys Glu Leu
                405                 410                 415

Phe Glu Gln Leu Gly Glu Tyr Lys Phe Gln Asn Ala Leu Leu Val Arg
            420                 425                 430

Tyr Thr Lys Lys Val Pro Gln Val Ser Thr Pro Thr Leu Val Glu Val
        435                 440                 445

Ser Arg Asn Leu Gly Lys Val Gly Ser Lys Cys Cys Lys His Pro Glu
    450                 455                 460

Ala Lys Arg Met Pro Cys Ala Glu Asp Tyr Leu Ser Val Val Leu Asn
465                 470                 475                 480

Gln Leu Cys Val Leu His Glu Lys Thr Pro Val Ser Asp Arg Val Thr
                485                 490                 495

Lys Cys Cys Thr Glu Ser Leu Val Asn Arg Arg Pro Cys Phe Ser Ala
            500                 505                 510

Leu Glu Val Asp Glu Thr Tyr Val Pro Lys Glu Phe Asn Ala Glu Thr
        515                 520                 525

Phe Thr Phe His Ala Asp Ile Cys Thr Leu Ser Glu Lys Glu Arg Gln
    530                 535                 540

Ile Lys Lys Gln Thr Ala Leu Val Glu Leu Val Lys His Lys Pro Lys
545                 550                 555                 560

Ala Thr Lys Glu Gln Leu Lys Ala Val Met Asp Asp Phe Ala Ala Phe
                565                 570                 575
```

```
Val Glu Lys Cys Cys Lys Ala Asp Asp Lys Glu Thr Cys Phe Ala Glu
        580                 585                 590

Glu Gly Lys Lys Leu Val Ala Ala Ser Gln Ala Ala Leu Gly Leu
        595                 600                 605

<210> SEQ ID NO 8
<211> LENGTH: 1821
<212> TYPE: DNA
<213> ORGANISM: Homo sapiens

<400> SEQUENCE: 8
```

| | | | | |
|---|---|---|---|---|
| atggacatga | gggtccccgc | tcagctcctg | gggctcctgc | tactctggct | ccgaggtgcc | 60 |
| agatgtgatg | cacacaagag | tgaggttgct | catcggttta | agatttgggg | agaagaaaat | 120 |
| ttcaaagcct | tggtgttgat | tgcctttgct | cagtatcttc | agcagtgtcc | atttgaagat | 180 |
| catgtaaaat | tagtgaatga | agtaactgaa | tttgcaaaaa | catgtgttgc | tgatgagtca | 240 |
| gctgaaaatt | gtgacaaatc | acttcatacc | cttttttggag | acaaattatg | cacagttgca | 300 |
| actcttcgtg | aaacctatgg | tgaaatggct | gactgctgtg | caaaacaaga | acctgagaga | 360 |
| aatgaatgct | tcttgcaaca | caaagatgac | aacccaaacc | tcccccgatt | ggtgagacca | 420 |
| gaggttgatg | tgatgtgcac | tgctttttcat | gacaatgaag | agacatttttt | gaaaaaatac | 480 |
| ttatatgaaa | ttgccagaag | acatccttac | ttttatgccc | cggaactcct | tttctttgct | 540 |
| aaaaggtata | agctgctttt | tacagaatgt | tgccaagctg | ctgataaagc | tgcctgcctg | 600 |
| ttgccaaagc | tcgatgaact | tcgggatgaa | gggaaggctt | cgtctgccaa | acagagactc | 660 |
| aagtgtgcca | gtctccaaaa | atttggagaa | agagctttca | aagcatgggc | agtagctcgc | 720 |
| ctgagccaga | gatttcccaa | agctgagttt | gcagaagttt | ccaagttagt | gacagatctt | 780 |
| accaaagtcc | acacggaatg | ctgccatgga | gatctgcttg | aatgtgctga | tgacagggcg | 840 |
| gaccttgcca | gtatatctg | tgaaaatcaa | gattcgatct | ccagtaaact | gaaggaatgc | 900 |
| tgtgaaaaac | ctctgttgga | aaaatcccac | tgcattgccg | aagtggaaaa | tgatgagatg | 960 |
| cctgctgact | tgcccttcatt | agctgctgat | tttgttgaaa | gtaaggatgt | ttgcaaaaac | 1020 |
| tatgctgagg | caaaggatgt | cttcctgggc | atgtttttgt | atgaatatgc | aagaaggcat | 1080 |
| cctgattact | ctgtcgtgct | gctgctgaga | cttgccaaga | catatgaaac | cactctagag | 1140 |
| aagtgctgtg | ccgctgcaga | tcctcatgaa | tgctatgcca | aagtgttcga | tgaatttaaa | 1200 |
| cctcttgtgg | aagagcctca | gaatttaatc | aaacaaaatt | gtgagctttt | tgagcagctt | 1260 |
| ggagagtaca | aattccagaa | tgcgctatta | gttcgttaca | ccaagaaagt | accccaagtg | 1320 |
| tcaactccaa | ctcttgtaga | ggtctcaaga | aacctaggaa | aagtgggcag | caaatgttgt | 1380 |
| aaacatcctg | aagcaaaaag | aatgccctgt | gcagaagact | atctatccgt | ggtcctgaac | 1440 |
| cagttatgtg | tgttgcatga | aaaacgccaa | gtaagtgaca | gagtcaccaa | atgctgcaca | 1500 |
| gaatccttgg | tgaacaggcg | accatgcttt | tcagctctgg | aagtcgatga | aacatacgtt | 1560 |
| cccaaagagt | ttaatgctga | acattcacc | ttccatgcag | atatatgcac | actttctgag | 1620 |
| aaggagagac | aaatcaagaa | acaaactgca | cttgttgagc | tcgtgaaaca | caagcccaag | 1680 |
| gcaacaaaag | agcaactgaa | agctgttatg | gatgatttcg | cagcttttgt | agagaagtgc | 1740 |
| tgcaaggctg | acgataagga | gacctgcttt | gccgaggagg | gtaaaaaact | tgttgctgca | 1800 |
| agtcaagctg | ccttaggctt | a | | | | 1821 |

```
<210> SEQ ID NO 9
<211> LENGTH: 585
<212> TYPE: PRT
<213> ORGANISM: Homo sapiens

<400> SEQUENCE: 9

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380
```

```
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
            405                 410                 415
Gln Val Ser Thr Pro Thr Leu Val Glu Val Ser Arg Asn Leu Gly Lys
        420                 425                 430
Val Gly Ser Lys Cys Cys Lys His Pro Glu Ala Lys Arg Met Pro Cys
    435                 440                 445
Ala Glu Asp Tyr Leu Ser Val Val Leu Asn Gln Leu Cys Val Leu His
450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
            500                 505                 510
Ile Cys Thr Leu Ser Glu Lys Glu Arg Gln Ile Lys Lys Gln Thr Ala
        515                 520                 525
Leu Val Glu Leu Val Lys His Lys Pro Lys Ala Thr Lys Glu Gln Leu
    530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu
            580                 585

<210> SEQ ID NO 10
<211> LENGTH: 1755
<212> TYPE: DNA
<213> ORGANISM: Homo sapiens

<400> SEQUENCE: 10
gatgcacaca agagtgaggt tgctcatcgg tttaaagatt tgggagaaga aaatttcaaa      60
gccttggtgt tgattgcctt tgctcagtat cttcagcagt gtccatttga agatcatgta     120
aaattagtga atgaagtaac tgaatttgca aaaacatgtg ttgctgatga gtcagctgaa     180
aattgtgaca atcacttcac tacccttttt ggagacaaat tatgcacagt tgcaactctt     240
cgtgaaacct atggtgaaat ggctgactgc tgtgcaaaac aagaacctga gagaaatgaa     300
tgcttcttgc aacacaaaga tgacaaccca acctccccc gattggtgag accagaggtt     360
gatgtgatgt gcactgcttt tcatgacaat gaagagacat ttttgaaaaa atacttatat     420
gaaattgcca agacatcc ttacttttat gccccggaac tccttttctt tgctaaaagg     480
tataaagctg cttttacaga atgttgccaa gctgctgata agctgcctg cctgttgcca     540 aagctcgatg aacttcggga tgaagggaag gcttcgtctg ccaaacagag actcaagtgt     600
gccagtctcc aaaaatttgg agaaagagct ttcaaagcat gggcagtagc tcgcctgagc     660
cagagatttc ccaaagctga gtttgcagaa gtttccaagt tagtgacaga tcttaccaaa     720
gtccacacgg aatgctgcca tggagatctg cttaatgtg ctgatgacag gcggaccttt     780
gccaagtata tctgtgaaaa tcaagattcg atctccagta aactgaagga atgctgtgaa     840
aaacctctgt tggaaaaatc ccactgcatt gccgaagtgg aaaatgatga gatgcctgct     900
gacttgcctt cattagctgc tgattttgtt gaaagtaagg atgtttgcaa aaactatgct     960
```

-continued

```
gaggcaaagg atgtcttcct gggcatgttt ttgtatgaat atgcaagaag gcatcctgat    1020
tactctgtcg tgctgctgct gagacttgcc aagacatatg aaaccactct agagaagtgc    1080
tgtgccgctg cagatcctca tgaatgctat gccaaagtgt tcgatgaatt taaacctctt    1140
gtggaagagc tcagaatttt aatcaaacaa aattgtgagc ttttgagca gcttggagag     1200 tacaaattcc agaatgcgct attagttcgt tacaccaaga aagtacccca agtgtcaact    1260
ccaactcttg tagaggtctc aagaaaccta ggaaaagtgg gcagcaaatg ttgtaaacat    1320
cctgaagcaa aagaatgcc ctgtgcagaa gactatctat ccgtggtcct gaaccagtta    1380
tgtgtgttgc atgagaaaac gccagtaagt gacagagtca ccaaatgctg cacagaatcc    1440
ttggtgaaca ggcgaccatg cttttcagct ctggaagtcg atgaaacata cgttcccaaa    1500
gagtttaatg ctgaaacatt caccttccat gcagatatat gcacactttc tgagaaggag    1560
agacaaatca gaaacaaac tgcacttgtt gagctcgtga acacaagcc caaggcaaca     1620 aaagagcaac tgaaagctgt tatggatgat ttcgcagctt ttgtagagaa gtgctgcaag    1680
gctgacgata aggagacctg ctttgccgag gagggtaaaa aacttgttgc tgcaagtcaa    1740
gctgccttag gctta                                                    1755

<210> SEQ ID NO 11
<211> LENGTH: 733
<212> TYPE: PRT
<213> ORGANISM: Artificial Sequence
<220> FEATURE:
<223> OTHER INFORMATION: synthetic polypeptide

<400> SEQUENCE: 11

Met Asp Met Arg Val Pro Ala Gln Leu Leu Gly Leu Leu Leu Leu Trp
1               5                   10                  15

Leu Arg Gly Ala Arg Cys Asp Ala His Lys Ser Glu Val Ala His Arg
            20                  25                  30

Phe Lys Asp Leu Gly Glu Glu Asn Phe Lys Ala Leu Val Leu Ile Ala
        35                  40                  45

Phe Ala Gln Tyr Leu Gln Gln Cys Pro Phe Glu Asp His Val Lys Leu
    50                  55                  60

Val Asn Glu Val Thr Glu Phe Ala Lys Thr Cys Val Ala Asp Glu Ser
65                  70                  75                  80

Ala Glu Asn Cys Asp Lys Ser Leu His Thr Leu Phe Gly Asp Lys Leu
                85                  90                  95

Cys Thr Val Ala Thr Leu Arg Glu Thr Tyr Gly Glu Met Ala Asp Cys
            100                 105                 110

Cys Ala Lys Gln Glu Pro Glu Arg Asn Glu Cys Phe Leu Gln His Lys
        115                 120                 125

Asp Asp Asn Pro Asn Leu Pro Arg Leu Val Arg Pro Glu Val Asp Val
    130                 135                 140

Met Cys Thr Ala Phe His Asp Asn Glu Glu Thr Phe Leu Lys Lys Tyr
145                 150                 155                 160

Leu Tyr Glu Ile Ala Arg Arg His Pro Tyr Phe Tyr Ala Pro Glu Leu
                165                 170                 175

Leu Phe Phe Ala Lys Arg Tyr Lys Ala Ala Phe Thr Glu Cys Cys Gln
            180                 185                 190

Ala Ala Asp Lys Ala Ala Cys Leu Leu Pro Lys Leu Asp Glu Leu Arg
        195                 200                 205

Asp Glu Gly Lys Ala Ser Ser Ala Lys Gln Arg Leu Lys Cys Ala Ser
    210                 215                 220
```

Leu Gln Lys Phe Gly Glu Arg Ala Phe Lys Ala Trp Ala Val Ala Arg
225                 230                 235                 240

Leu Ser Gln Arg Phe Pro Lys Ala Glu Phe Ala Glu Val Ser Lys Leu
            245                 250                 255

Val Thr Asp Leu Thr Lys Val His Thr Glu Cys Cys His Gly Asp Leu
            260                 265                 270

Leu Glu Cys Ala Asp Asp Arg Ala Asp Leu Ala Lys Tyr Ile Cys Glu
        275                 280                 285

Asn Gln Asp Ser Ile Ser Ser Lys Leu Lys Glu Cys Cys Glu Lys Pro
    290                 295                 300

Leu Leu Glu Lys Ser His Cys Ile Ala Glu Val Glu Asn Asp Glu Met
305                 310                 315                 320

Pro Ala Asp Leu Pro Ser Leu Ala Ala Asp Phe Val Glu Ser Lys Asp
            325                 330                 335

Val Cys Lys Asn Tyr Ala Glu Ala Lys Asp Val Phe Leu Gly Met Phe
            340                 345                 350

Leu Tyr Glu Tyr Ala Arg Arg His Pro Asp Tyr Ser Val Val Leu Leu
        355                 360                 365

Leu Arg Leu Ala Lys Thr Tyr Glu Thr Thr Leu Glu Lys Cys Cys Ala
    370                 375                 380

Ala Ala Asp Pro His Glu Cys Tyr Ala Lys Val Phe Asp Glu Phe Lys
385                 390                 395                 400

Pro Leu Val Glu Glu Pro Gln Asn Leu Ile Lys Gln Asn Cys Glu Leu
            405                 410                 415

Phe Glu Gln Leu Gly Glu Tyr Lys Phe Gln Asn Ala Leu Leu Val Arg
            420                 425                 430

Tyr Thr Lys Lys Val Pro Gln Val Ser Thr Pro Thr Leu Val Glu Val
        435                 440                 445

Ser Arg Asn Leu Gly Lys Val Gly Ser Lys Cys Cys Lys His Pro Glu
    450                 455                 460

Ala Lys Arg Met Pro Cys Ala Glu Asp Tyr Leu Ser Val Val Leu Asn
465                 470                 475                 480

Gln Leu Cys Val Leu His Glu Lys Thr Pro Val Ser Asp Arg Val Thr
            485                 490                 495

Lys Cys Cys Thr Glu Ser Leu Val Asn Arg Arg Pro Cys Phe Ser Ala
            500                 505                 510

Leu Glu Val Asp Glu Thr Tyr Val Pro Lys Glu Phe Asn Ala Glu Thr
        515                 520                 525

Phe Thr Phe His Ala Asp Ile Cys Thr Leu Ser Glu Lys Glu Arg Gln
    530                 535                 540

Ile Lys Lys Gln Thr Ala Leu Val Glu Leu Val Lys His Lys Pro Lys
545                 550                 555                 560

Ala Thr Lys Glu Gln Leu Lys Ala Val Met Asp Asp Phe Ala Ala Phe
            565                 570                 575

Val Glu Lys Cys Cys Lys Ala Asp Asp Lys Glu Thr Cys Phe Ala Glu
            580                 585                 590

Glu Gly Lys Lys Leu Val Ala Ala Ser Gln Ala Ala Leu Gly Leu Gly
        595                 600                 605

Gly Gly Gly Ser Gly Gly Gly Ser Ile Glu Gly Arg Ala Arg Asn
    610                 615                 620

Gly Asp His Cys Pro Leu Gly Pro Gly Arg Cys Cys Arg Leu His Thr
625                 630                 635                 640

| | | | | | | | | | | |
|---|---|---|---|---|---|---|---|---|---|---|
|Val|Arg|Ala|Ser|Leu|Glu|Asp|Leu|Gly|Trp|Ala|Asp|Trp|Val|Leu|Ser|
| | | | |645| | | |650| | | |655| |

Pro Arg Glu Val Gln Val Thr Met Cys Ile Gly Ala Cys Pro Ser Gln
           660                 665                 670

Phe Arg Ala Ala Asn Met His Ala Gln Ile Lys Thr Ser Leu His Arg
       675                 680                 685

Leu Lys Pro Asp Thr Val Pro Ala Pro Cys Cys Val Pro Ala Ser Tyr
   690                 695                 700

Asn Pro Met Val Leu Ile Gln Lys Thr Asp Thr Gly Val Ser Leu Gln
705                 710                 715                 720

Thr Tyr Asp Asp Leu Leu Ala Lys Asp Cys His Cys Ile
               725                 730

<210> SEQ ID NO 12
<211> LENGTH: 2202
<212> TYPE: DNA
<213> ORGANISM: Artificial Sequence
<220> FEATURE:
<223> OTHER INFORMATION: synthetic polynucleotide

<400> SEQUENCE: 12
atggacatga gggtccccgc tcagctcctg gggctcctgc tactctggct ccgaggtgcc      60
agatgtgatg cacacaagag tgaggttgct catcggttta agatttggg agaagaaaat     120 ttcaaagcct tggtgttgat tgcctttgct cagtatcttc agcagtgtcc atttgaagat    180
catgtaaaat tagtgaatga agtaactgaa tttgcaaaaa catgtgttgc tgatgagtca     240
gctgaaaatt gtgacaaatc acttcatacc cttttggag acaaattatg cacagttgca     300
actcttcgtg aaacctatgg tgaaatggct gactgctgtg caaaacaaga acctgagaga    360
aatgaatgct tcttgcaaca caagatgac aacccaaacc tcccccgatt ggtgagacca    420
gaggttgatg tgatgtgcac tgcttttcat gacaatgaag acatttttt gaaaaaatac     480 ttatatgaaa ttgccagaag acatccttac ttttatgccc cggaactcct tttctttgct    540
aaaaggtata agctgctttt tacagaatgt tgccaagctg ctgataaagc tgcctgcctg    600
ttgccaaagc tcgatgaact tcgggatgaa gggaaggctc gtctgccaa acagagactc    660 aagtgtgcca gtctccaaaa atttggagaa agagctttca agcatgggc agtagctcgc    720 ctgagccaga gatttcccaa agctgagttt gcagaagttt ccaagttagt gacagatctt    780
accaaagtcc acacggaatg ctgccatgga gatctgcttg aatgtgctga tgacagggcg    840
gaccttgcca gtatatctg tgaaaatcaa gattcgatct ccagtaaact gaaggaatgc    900
tgtgaaaaac ctctgttgga aaaatcccac tgcattgccg aagtggaaaa tgatgagatg    960
cctgctgact gccttcatt agctgctgat tttgttgaaa gtaaggatgt ttgcaaaaac   1020
tatgctgagg caaaggatgt cttcctgggc atgttttgt atgaatatgc aagaaggcat   1080
cctgattact ctgtcgtgct gctgctgaga cttgccaaga catatgaaac cactctagag   1140
aagtgctgtg ccgctgcaga tcctcatgaa tgctatgcca agtgttcga tgaatttaaa   1200 cctcttgtgg aagagcctca gaatttaatc aaacaaaatt gtgagctttt tgagcagctt   1260
ggagagtaca aattccagaa tgcgctatta gttcgttaca ccaagaaagt accccaagtg   1320
tcaactccaa ctcttgtaga ggtctcaaga aacctaggaa aagtgggcag caaatgttgt   1380
aaacatcctg aagcaaaaag aatgccctgt gcagaagact atctatccgt ggtcctgaac   1440
cagttatgtg tgttgcatga aaaacgcca gtaagtgaca gagtcaccaa atgctgcaca   1500
gaatccttgg tgaacaggcg accatgcttt tcagctctgg aagtcgatga acatacgtt   1560

```
cccaaagagt ttaatgctga acattcacc ttccatgcag atatatgcac actttctgag    1620
aaggagagac aaatcaagaa acaaactgca cttgttgagc tcgtgaaaca caagcccaag    1680
gcaacaaaag agcaactgaa agctgttatg gatgatttcg cagcttttgt agagaagtgc    1740
tgcaaggctg acgataagga gacctgcttt gccgaggagg gtaaaaaact tgttgctgca    1800
agtcaagctg ccttaggctt aggtggaggc ggtagcggtg gaggtgggag tattgaaggg    1860
agggcgcgta acggggatca ctgtccgctc gggcccgggc gttgctgccg tctgcacacg    1920
gtccgcgcgt cgctggaaga cctgggctgg gccgattggg tgctgtcgcc acgggaggtg    1980
caagtgacca tgtgcatcgg cgcgtgcccg agccagttcc gggcggcaaa catgcacgcg    2040
cagatcaaga cgagcctgca ccgcctgaag cccgacacgg tgccagcgcc ctgctgcgtg    2100
cccgccagct acaatcccat ggtgctcatt caaaagaccg acaccggggt gtcgctccag    2160
acctatgatg acttgttagc caaagactgc cactgcatat aa                      2202
```

<210> SEQ ID NO 13
<211> LENGTH: 711
<212> TYPE: PRT
<213> ORGANISM: Artificial sequence
<220> FEATURE:
<223> OTHER INFORMATION: synthetic polypeptide

<400> SEQUENCE: 13

```
Asp Ala His Lys Ser Glu Val Ala His Arg Phe Lys Asp Leu Gly Glu
  1               5                  10                  15

Glu Asn Phe Lys Ala Leu Val Leu Ile Ala Phe Ala Gln Tyr Leu Gln
             20                  25                  30

Gln Cys Pro Phe Glu Asp His Val Lys Leu Val Asn Glu Val Thr Glu
         35                  40                  45

Phe Ala Lys Thr Cys Val Ala Asp Glu Ser Ala Glu Asn Cys Asp Lys
     50                  55                  60

Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255
```

-continued

```
Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
275                 280                 285

Cys Ile Ala Glu Val Glu Asn Asp Glu Met Pro Ala Asp Leu Pro Ser
        290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Gly Gly Ser Gly Gly
            580                 585                 590

Gly Gly Ser Ile Glu Gly Arg Ala Arg Asn Gly Asp His Cys Pro Leu
        595                 600                 605

Gly Pro Gly Arg Cys Cys Arg Leu His Thr Val Arg Ala Ser Leu Glu
    610                 615                 620

Asp Leu Gly Trp Ala Asp Trp Val Leu Ser Pro Arg Glu Val Gln Val
625                 630                 635                 640

Thr Met Cys Ile Gly Ala Cys Pro Ser Gln Phe Arg Ala Ala Asn Met
                645                 650                 655

His Ala Gln Ile Lys Thr Ser Leu His Arg Leu Lys Pro Asp Thr Val
            660                 665                 670
```

```
Pro Ala Pro Cys Cys Val Pro Ala Ser Tyr Asn Pro Met Val Leu Ile
        675                 680                 685

Gln Lys Thr Asp Thr Gly Val Ser Leu Gln Thr Tyr Asp Asp Leu Leu
    690                 695                 700

Ala Lys Asp Cys His Cys Ile
705                 710

<210> SEQ ID NO 14
<211> LENGTH: 2136
<212> TYPE: DNA
<213> ORGANISM: Artificial sequence
<220> FEATURE:
<223> OTHER INFORMATION: synthetic polynucleotide

<400> SEQUENCE: 14
gatgcacaca agagtgaggt tgctcatcgg tttaaagatt tgggagaaga aaatttcaaa      60
gccttggtgt tgattgcctt tgctcagtat cttcagcagt gtccatttga agatcatgta    120
aaattagtga atgaagtaac tgaatttgca aaacatgtg ttgctgatga gtcagctgaa    180
aattgtgaca atcacttca tacccttttt ggagacaaat tatgcacagt tgcaactctt    240
cgtgaaacct atggtgaaat ggctgactgc tgtgcaaaac aagaacctga gaaaatgaa    300 tgcttcttgc aacacaaaga tgacaaccca acctccccc gattggtgag accagaggtt    360
gatgtgatgt gcactgcttt tcatgacaat aagagacat ttttgaaaaa atacttatat    420
gaaattgcca aagacatcc ttactttat gccccggaac tccttttctt tgctaaaagg    480
tataaagctg cttttacaga atgttgccaa gctgctgata agctgcctg cctgttgcca    540 aagctcgatg aacttcggga tgaagggaag gcttcgtctg ccaaacagag actcaagtgt    600
gccagtctcc aaaaatttgg agaaagagct ttcaaagcat gggcagtagc tcgcctgagc    660
cagagatttc ccaaagctga gtttgcagaa gtttccaagt tagtgacaga tcttaccaaa    720
gtccacacgg aatgctgcca tggagatctg cttgaatgtg ctgatgacag gcggaccttt    780
gccaagtata tctgtgaaaa tcaagattcg atctccagta aactgaagga tgctgtgaa    840 aaacctctgt tggaaaaatc ccactgcatt gccgaagtgg aaaatgatga gatgcctgct    900
gacttgcctt cattagctgc tgatttttgtt gaaagtaagg atgtttgcaa aaactatgct    960
gaggcaaagg atgtcttcct gggcatgttt ttgtatgaat atgcaagaag gcatcctgat   1020
tactctgtcg tgctgctgct gagacttgcc aagacatatg aaaccactct agagaagtgc   1080
tgtgccgctg cagatcctca tgaatgctat gccaaagtgt tcgatgaatt taaacctctt   1140
gtggaagagc ctcagaattt aatcaaacaa aattgtgagc tttttgagca gcttggagag   1200
tacaaattcc agaatgcgct attagttcgt tacaccaaga agtaccccca agtgtcaact   1260
ccaactcttg tagaggtctc aagaaaccta ggaaaagtgg gcagcaaatg ttgtaaacat   1320
cctgaagcaa aaagaatgcc ctgtgcagaa gactatctat ccgtggtcct gaaccagtta   1380
tgtgtgttgc atgagaaaac gccagtaagt gacagagtca ccaaatgctg cacagaatcc   1440
ttggtgaaca ggcgaccatg cttttcagct ctggaagtcg atgaaacata cgttcccaaa   1500
gagtttaatg ctgaaacatt caccttccat gcagatatat gcacactttc tgagaaggag   1560
agacaaatca gaaacaaac tgcacttgtt gagctcgtga acacaagcc caaggcaaca   1620 aaagagcaac tgaaagctgt tatggatgat ttcgcagctt ttgtagagaa gtgctgcaag   1680
gctgacgata aggagacctg ctttgccgag agggtaaaa aacttgttgc tgcaagtcaa   1740
gctgccttag gcttaggtgg aggcggtagc ggtggaggtg ggagtattga agggagggcg   1800
```

```
cgtaacgggg atcactgtcc gctcgggccc gggcgttgct gccgtctgca cacggtccgc    1860
gcgtcgctgg aagacctggg ctgggccgat tgggtgctgt cgccacggga ggtgcaagtg    1920
accatgtgca tcggcgcgtg cccgagccag ttccggcgg caaacatgca cgcgcagatc    1980
aagacgagcc tgcaccgcct gaagcccgac acggtgccag cgccctgctg cgtgcccgcc    2040
agctacaatc ccatggtgct cattcaaaag accgacaccg gggtgtcgct ccagacctat    2100
gatgacttgt tagccaaaga ctgccactgc atataa                              2136
```

<210> SEQ ID NO 15
<211> LENGTH: 734
<212> TYPE: PRT
<213> ORGANISM: Artificial sequence
<220> FEATURE:
<223> OTHER INFORMATION: synthetic polypeptide

<400> SEQUENCE: 15

```
Met Asp Met Arg Val Pro Ala Gln Leu Leu Gly Leu Leu Leu Leu Trp
1               5                   10                  15

Leu Arg Gly Ala Arg Cys Asp Ala His Lys Ser Glu Val Ala His Arg
            20                  25                  30

Phe Lys Asp Leu Gly Glu Glu Asn Phe Lys Ala Leu Val Leu Ile Ala
        35                  40                  45

Phe Ala Gln Tyr Leu Gln Gln Cys Pro Phe Glu Asp His Val Lys Leu
    50                  55                  60

Val Asn Glu Val Thr Glu Phe Ala Lys Thr Cys Val Ala Asp Glu Ser
65                  70                  75                  80

Ala Glu Asn Cys Asp Lys Ser Leu His Thr Leu Phe Gly Asp Lys Leu
                85                  90                  95

Cys Thr Val Ala Thr Leu Arg Glu Thr Tyr Gly Glu Met Ala Asp Cys
            100                 105                 110

Cys Ala Lys Gln Glu Pro Glu Arg Asn Glu Cys Phe Leu Gln His Lys
        115                 120                 125

Asp Asp Asn Pro Asn Leu Pro Arg Leu Val Arg Pro Glu Val Asp Val
    130                 135                 140

Met Cys Thr Ala Phe His Asp Asn Glu Glu Thr Phe Leu Lys Lys Tyr
145                 150                 155                 160

Leu Tyr Glu Ile Ala Arg Arg His Pro Tyr Phe Tyr Ala Pro Glu Leu
                165                 170                 175

Leu Phe Phe Ala Lys Arg Tyr Lys Ala Ala Phe Thr Glu Cys Cys Gln
            180                 185                 190

Ala Ala Asp Lys Ala Ala Cys Leu Leu Pro Lys Leu Asp Glu Leu Arg
        195                 200                 205

Asp Glu Gly Lys Ala Ser Ser Ala Lys Gln Arg Leu Lys Cys Ala Ser
    210                 215                 220

Leu Gln Lys Phe Gly Glu Arg Ala Phe Lys Ala Trp Ala Val Ala Arg
225                 230                 235                 240

Leu Ser Gln Arg Phe Pro Lys Ala Glu Phe Ala Glu Val Ser Lys Leu
                245                 250                 255

Val Thr Asp Leu Thr Lys Val His Thr Glu Cys Cys His Gly Asp Leu
            260                 265                 270

Leu Glu Cys Ala Asp Asp Arg Ala Asp Leu Ala Lys Tyr Ile Cys Glu
        275                 280                 285

Asn Gln Asp Ser Ile Ser Ser Lys Leu Lys Glu Cys Cys Glu Lys Pro
    290                 295                 300
```

-continued

```
Leu Leu Glu Lys Ser His Cys Ile Ala Glu Val Glu Asn Asp Glu Met
305                 310                 315                 320

Pro Ala Asp Leu Pro Ser Leu Ala Ala Asp Phe Val Glu Ser Lys Asp
            325                 330                 335

Val Cys Lys Asn Tyr Ala Glu Ala Lys Asp Val Phe Leu Gly Met Phe
            340                 345                 350

Leu Tyr Glu Tyr Ala Arg Arg His Pro Asp Tyr Ser Val Val Leu Leu
            355                 360                 365

Leu Arg Leu Ala Lys Thr Tyr Glu Thr Thr Leu Glu Lys Cys Cys Ala
            370                 375                 380

Ala Ala Asp Pro His Glu Cys Tyr Ala Lys Val Phe Asp Glu Phe Lys
385                 390                 395                 400

Pro Leu Val Glu Glu Pro Gln Asn Leu Ile Lys Gln Asn Cys Glu Leu
            405                 410                 415

Phe Glu Gln Leu Gly Glu Tyr Lys Phe Gln Asn Ala Leu Leu Val Arg
            420                 425                 430

Tyr Thr Lys Lys Val Pro Gln Val Ser Thr Pro Thr Leu Val Glu Val
            435                 440                 445

Ser Arg Asn Leu Gly Lys Val Gly Ser Lys Cys Cys Lys His Pro Glu
450                 455                 460

Ala Lys Arg Met Pro Cys Ala Glu Asp Tyr Leu Ser Val Val Leu Asn
465                 470                 475                 480

Gln Leu Cys Val Leu His Glu Lys Thr Pro Val Ser Asp Arg Val Thr
            485                 490                 495

Lys Cys Cys Thr Glu Ser Leu Val Asn Arg Arg Pro Cys Phe Ser Ala
            500                 505                 510

Leu Glu Val Asp Glu Thr Tyr Val Pro Lys Glu Phe Asn Ala Glu Thr
            515                 520                 525

Phe Thr Phe His Ala Asp Ile Cys Thr Leu Ser Glu Lys Glu Arg Gln
            530                 535                 540

Ile Lys Lys Gln Thr Ala Leu Val Glu Leu Val Lys His Lys Pro Lys
545                 550                 555                 560

Ala Thr Lys Glu Gln Leu Lys Ala Val Met Asp Asp Phe Ala Ala Phe
            565                 570                 575

Val Glu Lys Cys Cys Lys Ala Asp Asp Lys Glu Thr Cys Phe Ala Glu
            580                 585                 590

Glu Gly Lys Lys Leu Val Ala Ala Ser Gln Ala Ala Leu Gly Leu Gly
            595                 600                 605

Gly Gly Gly Ser Gly Gly Gly Ser Gly Gly Gly Ser Ala Arg
            610                 615                 620

Asn Gly Asp His Cys Pro Leu Gly Pro Gly Arg Cys Cys Arg Leu His
625                 630                 635                 640

Thr Val Arg Ala Ser Leu Glu Asp Leu Gly Trp Ala Asp Trp Val Leu
            645                 650                 655

Ser Pro Arg Glu Val Gln Val Thr Met Cys Ile Gly Ala Cys Pro Ser
            660                 665                 670

Gln Phe Arg Ala Ala Asn Met His Ala Gln Ile Lys Thr Ser Leu His
            675                 680                 685

Arg Leu Lys Pro Asp Thr Val Pro Ala Pro Cys Cys Val Pro Ala Ser
            690                 695                 700
```

Tyr Asn Pro Met Val Leu Ile Gln Lys Thr Asp Thr Gly Val Ser Leu
705                 710                 715                 720

Gln Thr Tyr Asp Asp Leu Leu Ala Lys Asp Cys His Cys Ile
                725                 730

<210> SEQ ID NO 16
<211> LENGTH: 2205
<212> TYPE: DNA
<213> ORGANISM: Artificial sequence
<220> FEATURE:
<223> OTHER INFORMATION: synthetic polynucleotide

<400> SEQUENCE: 16

```
atggacatga gggtccccgc tcagctcctg gggctcctgc tactctggct ccgaggtgcc      60
agatgtgatg cacacaagag tgaggttgct catcggttta agatttggg agaagaaaat     120
ttcaaagcct tggtgttgat tgcctttgct cagtatcttc agcagtgtcc atttgaagat    180
catgtaaaat tagtgaatga agtaactgaa tttgcaaaaa catgtgttgc tgatgagtca    240
gctgaaaatt gtgacaaatc acttcatacc ctttttggag acaaattatg cacagttgca    300
actcttcgtg aaacctatgg tgaaatggct gactgctgtg caaaacaaga acctgagaga    360
aatgaatgct tcttgcaaca caaagatgac aacccaaacc tcccccgatt ggtgagacca    420
gaggttgatg tgatgtgcac tgcttttcat gacaatgaag agacattttt gaaaaaatac    480
ttatatgaaa ttgccagaag acatccttac ttttatgccc cggaactcct tttctttgct    540
aaaaggtata agctgctttt tacagaatgt tgccaagctg ctgataaagc tgcctgcctg    600
ttgccaaagc tcgatgaact tcgggatgaa gggaaggctt cgtctgccaa acagagactc    660
aagtgtgcca gtctccaaaa atttggagaa agagcttca aagcatgggc agtagctcgc    720
ctgagccaga gatttcccaa agctgagttt gcagaagttt ccaagttagt gacagatctt    780
accaaagtcc acacggaatg ctgccatgga gatctgcttg aatgtgctga tgacagggcg    840
gaccttgcca gtatatctg tgaaaatcaa gattcgatct ccagtaaact gaaggaatgc    900
tgtgaaaaac ctctgttgga aaaatcccac tgcattgccg aagtggaaaa tgatgagatg    960
cctgctgact tgccttcatt agctgctgat tttgttgaaa gtaaggatgt ttgcaaaaac   1020
tatgctgagg caaaggatgt cttcctgggc atgtttttgt atgaatatgc aagaaggcat   1080
cctgattact ctgtcgtgct gctgctgaga cttgccaaga catatgaaac cactctagag   1140
aagtgctgtg ccgctgcaga tcctcatgaa tgctatgcca aagtgttcga tgaatttaaa   1200
cctcttgtgg aagagcctca gaatttaatc aaacaaaatt gtgagctttt tgagcagctt   1260
ggagagtaca aattccagaa tgcgctatta gttcgttaca ccaagaaagt accccaagtg   1320
tcaactccaa ctcttgtaga ggtctcaaga aacctaggaa aagtgggcag caaatgttgt   1380
aaacatcctg aagcaaaaag aatgccctgt gcagaagact atctatccgt ggtcctgaac   1440
cagttatgtg tgttgcatga aaaacgcca gtaagtgaca gagtcaccaa atgctgcaca   1500
gaatccttgg tgaacaggcg accatgcttt tcagctctgg aagtcgatga acatacgtt   1560
cccaaagagt ttaatgctga acattcacc ttccatgcag atatatgcac actttctgag   1620
aaggagagac aaatcaagaa acaaactgca cttgttgagc tcgtgaaaca caagcccaag   1680
gcaacaaaag agcaactgaa agctgttatg gatgatttcg cagcttttgt agagaagtgc   1740
tgcaaggctg acgataagga gacctgcttt gccgaggagg gtaaaaaact tgttgctgca   1800
agtcaagctg ccttaggctt aggtggaggc ggtagcggtg gaggtgggag tggtggaggt   1860
gggagtgcgc gtaacgggga tcactgtccg ctcgggcccg ggcgttgctg ccgtctgcac   1920
```

| | | |
|---|---|---|
| acggtccgcg cgtcgctgga agacctgggc tgggccgatt gggtgctgtc gccacgggag | 1980 |
| gtgcaagtga ccatgtgcat cggcgcgtgc ccgagccagt tccgggcggc aaacatgcac | 2040 |
| gcgcagatca agacgagcct gcaccgcctg aagcccgaca cggtgccagc gccctgctgc | 2100 |
| gtgcccgcca gctacaatcc catggtgctc attcaaaaga ccgacaccgg ggtgtcgctc | 2160 |
| cagacctatg atgacttgtt agccaaagac tgccactgca tataa | 2205 |

```
<210> SEQ ID NO 17
<211> LENGTH: 712
<212> TYPE: PRT
<213> ORGANISM: Artificial sequence
<220> FEATURE:
<223> OTHER INFORMATION: synthetic polypeptide

<400> SEQUENCE: 17
```

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

```
Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Gly Gly Ser Gly Gly Gly
            580                 585                 590

Gly Gly Ser Gly Gly Gly Ser Ala Arg Asn Gly Asp His Cys Pro
        595                 600                 605

Leu Gly Pro Gly Arg Cys Cys Arg Leu His Thr Val Arg Ala Ser Leu
610                 615                 620

Glu Asp Leu Gly Trp Ala Asp Trp Val Leu Ser Pro Arg Glu Val Gln
625                 630                 635                 640

Val Thr Met Cys Ile Gly Ala Cys Pro Ser Gln Phe Arg Ala Ala Asn
                645                 650                 655

Met His Ala Gln Ile Lys Thr Ser Leu His Arg Leu Lys Pro Asp Thr
            660                 665                 670

Val Pro Ala Pro Cys Cys Val Pro Ala Ser Tyr Asn Pro Met Val Leu
        675                 680                 685

Ile Gln Lys Thr Asp Thr Gly Val Ser Leu Gln Thr Tyr Asp Asp Leu
690                 695                 700

Leu Ala Lys Asp Cys His Cys Ile
705                 710
```

<210> SEQ ID NO 18
<211> LENGTH: 2139
<212> TYPE: DNA
<213> ORGANISM: Artificial sequence
<220> FEATURE:
<223> OTHER INFORMATION: synthetic polynucleotide

<400> SEQUENCE: 18

```
gatgcacaca agagtgaggt tgctcatcgg tttaaagatt tgggagaaga aaatttcaaa      60
gccttggtgt tgattgcctt tgctcagtat cttcagcagt gtccatttga agatcatgta     120
aaattagtga atgaagtaac tgaatttgca aaaacatgtg ttgctgatga gtcagctgaa     180
aattgtgaca aatcacttca tacccttttt ggagacaaat tatgcacagt tgcaactctt     240
cgtgaaacct atggtgaaat ggctgactgc tgtgcaaaac aagaacctga gagaaatgaa     300
tgcttcttgc aacacaaaga tgacaaccca aacctccccc gattggtgag accagaggtt     360
gatgtgatgt gcactgcttt tcatgacaat gaagagacat ttttgaaaaa atacttatat     420
gaaattgcca aagacatcc ttacttttat gccccggaac tcctttttctt tgctaaaagg      480
tataaagctg cttttacaga atgttgccaa gctgctgata agctgcctg cctgttgcca      540
aagctcgatg aacttcggga tgaagggaag gcttcgtctg ccaaacagag actcaagtgt     600
gccagtctcc aaaaatttgg agaaagagct ttcaaagcat gggcagtagc tcgcctgagc     660
cagagatttc ccaaagctga gtttgcagaa gtttccaagt tagtgacaga tcttaccaaa     720
gtccacacgg aatgctgcca tggagatctg cttgaatgtg ctgatgacag ggcggacctt     780
gccaagtata tctgtgaaaa tcaagattcg atctccagta aactgaagga atgctgtgaa     840
aaacctctgt tggaaaaatc ccactgcatt gccgaagtgg aaaatgatga gatgcctgct     900
gacttgcctt cattagctgc tgattttgtt gaaagtaagg atgtttgcaa aaactatgct     960
gaggcaaagg atgtcttcct gggcatgttt ttgtatgaat atgcaagaag gcatcctgat    1020
tactctgtcg tgctgctgct gagacttgcc aagacatatg aaaccactct agagaagtgc    1080
tgtgccgctg cagatcctca tgaatgctat gccaaagtgt tcgatgaatt taaacctctt    1140
gtggaagagc ctcagaattt aatcaaacaa aattgtgagc ttttgagca gcttggagag    1200
tacaaattcc agaatgcgct attagttcgt tacaccaaga aagtacccca agtgtcaact    1260
ccaactcttg tagaggtctc aagaaaccta ggaaaagtgg gcagcaaatg ttgtaaacat    1320
cctgaagcaa aaagaatgcc ctgtgcagaa gactatctat ccgtggtcct gaaccagtta    1380
tgtgtgttgc atgagaaaac gccagtaagt gacagagtca ccaaatgctg cacagaatcc    1440
ttggtgaaca gccgaccatg cttttcagct ctggaagtcg atgaaacata cgttcccaaa    1500
gagtttaatg ctgaaacatt caccttccat gcagatatat gcacactttc tgagaaggag    1560
agacaaatca gaaacaaac tgcacttgtt gagctcgtga acacaagcc caaggcaaca    1620
aaagagcaac tgaaagctgt tatggatgat ttcgcagctt ttgtagagaa gtgctgcaag    1680
gctgacgata aggagacctg ctttgccgag gagggtaaaa aacttgttgc tgcaagtcaa    1740
gctgccttag gctaggtgg aggcggtagc ggtggaggtg ggagtggtgg aggtgggagt    1800
gcgcgtaacg gggatcactg tccgctcggg cccgggcgtt gctgccgtct gcacacggtc    1860
cgcgcgtcgc tggaagacct gggctgggcc gattgggtgc tgtcgccacg ggaggtgcaa    1920
gtgaccatgt gcatcggcgc gtgcccgagc cagttccggg cggcaaacat gcacgcgcag    1980
atcaagacga gcctgcaccg cctgaagccc gacacggtgc cagcgccctg ctgcgtgccc    2040
```

```
gccagctaca atcccatggt gctcattcaa aagaccgaca ccggggtgtc gctccagacc    2100
tatgatgact tgttagccaa agactgccac tgcatataa                          2139
```

<210> SEQ ID NO 19
<211> LENGTH: 112
<212> TYPE: PRT
<213> ORGANISM: Artificial sequence
<220> FEATURE:
<223> OTHER INFORMATION: synthetic polypeptide

<400> SEQUENCE: 19

```
Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Ala Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 20
<211> LENGTH: 112
<212> TYPE: PRT
<213> ORGANISM: Artificial sequence
<220> FEATURE:
<223> OTHER INFORMATION: synthetic polypeptide

<400> SEQUENCE: 20

```
Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Ala
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 21
<211> LENGTH: 112
<212> TYPE: PRT
<213> ORGANISM: Artificial sequence
<220> FEATURE:
<223> OTHER INFORMATION: synthetic polypeptide

```
<400> SEQUENCE: 21

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Ala Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 22
<211> LENGTH: 112
<212> TYPE: PRT
<213> ORGANISM: Artificial sequence
<220> FEATURE:
<223> OTHER INFORMATION: synthetic polypeptide

<400> SEQUENCE: 22

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Ala His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 23
<211> LENGTH: 112
<212> TYPE: PRT
<213> ORGANISM: Artificial sequence
<220> FEATURE:
<223> OTHER INFORMATION: synthetic polypeptide

<400> SEQUENCE: 23

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Ala Lys Pro Asp Thr Val Pro Ala Pro Cys Cys Val Pro
65                  70                  75                  80
```

Ala Ser Tyr Asn Pro Met Val Leu Ile Gln Lys Thr Asp Thr Gly Val
            85                  90                  95

Ser Leu Gln Thr Tyr Asp Asp Leu Leu Ala Lys Asp Cys His Cys Ile
            100                 105                 110

<210> SEQ ID NO 24
<211> LENGTH: 112
<212> TYPE: PRT
<213> ORGANISM: Artificial sequence
<220> FEATURE:
<223> OTHER INFORMATION: synthetic polypeptide

<400> SEQUENCE: 24

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ala Gln Lys Thr Asp Thr Gly Val
            85                  90                  95

Ser Leu Gln Thr Tyr Asp Asp Leu Leu Ala Lys Asp Cys His Cys Ile
            100                 105                 110

<210> SEQ ID NO 25
<211> LENGTH: 112
<212> TYPE: PRT
<213> ORGANISM: Artificial sequence
<220> FEATURE:
<223> OTHER INFORMATION: synthetic polypeptide

<400> SEQUENCE: 25

Ala Arg Asn Gly Asp His Cys Pro Leu Gly Pro Gly Arg Cys Cys Arg
1               5                   10                  15

Leu His Thr Val Arg Ala Ser Leu Ala Ala Leu Gly Trp Ala Ala Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
            85                  90                  95

Ser Leu Gln Thr Tyr Asp Asp Leu Leu Ala Lys Asp Cys His Cys Ile
            100                 105                 110

<210> SEQ ID NO 26
<211> LENGTH: 112
<212> TYPE: PRT
<213> ORGANISM: Artificial sequence
<220> FEATURE:
<223> OTHER INFORMATION: synthetic polypeptide

<400> SEQUENCE: 26

Ala Arg Asn Gly Asp His Cys Pro Leu Gly Pro Gly Arg Cys Cys Arg
1               5                   10                  15

Leu His Thr Val Arg Ala Ser Leu Ala Ala Leu Gly Trp Ala Ala Trp
            20                  25                  30

Val Leu Ser Pro Arg Ala Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 27
<211> LENGTH: 112
<212> TYPE: PRT
<213> ORGANISM: Artificial sequence
<220> FEATURE:
<223> OTHER INFORMATION: synthetic polypeptide

<400> SEQUENCE: 27

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Ala Ala Leu Leu Ala Lys Ala Cys His Cys Ile
            100                 105                 110

<210> SEQ ID NO 28
<211> LENGTH: 112
<212> TYPE: PRT
<213> ORGANISM: Artificial sequence
<220> FEATURE:
<223> OTHER INFORMATION: synthetic polypeptide

<400> SEQUENCE: 28

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Ala Thr Gly Val
                85                  90                  95

Ser Leu Gln Thr Tyr Ala Ala Leu Leu Ala Lys Ala Cys His Cys Ile
            100                 105                 110

<210> SEQ ID NO 29
<211> LENGTH: 112
<212> TYPE: PRT
<213> ORGANISM: Artificial sequence
<220> FEATURE:
<223> OTHER INFORMATION: synthetic polypeptide

<400> SEQUENCE: 29

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Ala Thr Gly Val
                85                  90                  95

Ser Leu Gln Thr Tyr Asp Asp Leu Leu Ala Lys Asp Cys His Cys Ile
            100                 105                 110

<210> SEQ ID NO 30
<211> LENGTH: 112
<212> TYPE: PRT
<213> ORGANISM: Artificial sequence
<220> FEATURE:
<223> OTHER INFORMATION: synthetic polypeptide

<400> SEQUENCE: 30

Ala Arg Asn Gly Thr His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 31
<211> LENGTH: 112
<212> TYPE: PRT
<213> ORGANISM: Artificial sequence
<220> FEATURE:
<223> OTHER INFORMATION: synthetic polypeptide

```
<400> SEQUENCE: 31

Ala Arg Asn Gly Asp His Cys Pro Leu Gly Pro Gly Arg Cys Cys Arg
1               5                   10                  15

Asn His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 32
<211> LENGTH: 112
<212> TYPE: PRT
<213> ORGANISM: Artificial sequence
<220> FEATURE:
<223> OTHER INFORMATION: synthetic polypeptide

<400> SEQUENCE: 32

Ala Arg Asn Gly Asp His Cys Pro Leu Gly Pro Gly Arg Cys Cys Arg
1               5                   10                  15

Leu His Thr Val Asn Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 33
<211> LENGTH: 112
<212> TYPE: PRT
<213> ORGANISM: Artificial sequence
<220> FEATURE:
<223> OTHER INFORMATION: synthetic polypeptide

<400> SEQUENCE: 33

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Asn Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80
```

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 34
<211> LENGTH: 112
<212> TYPE: PRT
<213> ORGANISM: Artificial sequence
<220> FEATURE:
<223> OTHER INFORMATION: synthetic polypeptide

<400> SEQUENCE: 34

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Asn Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 35
<211> LENGTH: 112
<212> TYPE: PRT
<213> ORGANISM: Artificial sequence
<220> FEATURE:
<223> OTHER INFORMATION: synthetic polypeptide

<400> SEQUENCE: 35

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met Thr Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 36
<211> LENGTH: 112
<212> TYPE: PRT
<213> ORGANISM: Artificial sequence
<220> FEATURE:
<223> OTHER INFORMATION: synthetic polypeptide

<400> SEQUENCE: 36

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Asn Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 37
<211> LENGTH: 112
<212> TYPE: PRT
<213> ORGANISM: Artificial sequence
<220> FEATURE:
<223> OTHER INFORMATION: synthetic polypeptide

<400> SEQUENCE: 37

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Asn Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 38
<211> LENGTH: 112
<212> TYPE: PRT
<213> ORGANISM: Artificial sequence
<220> FEATURE:
<223> OTHER INFORMATION: synthetic polypeptide

<400> SEQUENCE: 38

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Asn Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 39
<211> LENGTH: 112
<212> TYPE: PRT
<213> ORGANISM: Artificial sequence
<220> FEATURE:
<223> OTHER INFORMATION: synthetic polypeptide

<400> SEQUENCE: 39

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Asn
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 40
<211> LENGTH: 112
<212> TYPE: PRT
<213> ORGANISM: Artificial sequence
<220> FEATURE:
<223> OTHER INFORMATION: synthetic polypeptide

<400> SEQUENCE: 40

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Asn Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 41
<211> LENGTH: 112
<212> TYPE: PRT
<213> ORGANISM: Artificial sequence
<220> FEATURE:
<223> OTHER INFORMATION: synthetic polypeptide -continued

```
<400> SEQUENCE: 41

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Asn Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 42
<211> LENGTH: 112
<212> TYPE: PRT
<213> ORGANISM: Artificial sequence
<220> FEATURE:
<223> OTHER INFORMATION: synthetic polypeptide

<400> SEQUENCE: 42

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Asn Val
                85                  90                  95

Ser Leu Gln Thr Tyr Asp Asp Leu Leu Ala Lys Asp Cys His Cys Ile
            100                 105                 110

<210> SEQ ID NO 43
<211> LENGTH: 112
<212> TYPE: PRT
<213> ORGANISM: Artificial sequence
<220> FEATURE:
<223> OTHER INFORMATION: synthetic polypeptide

<400> SEQUENCE: 43

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80
```

Ala Ser Tyr Asn Pro Met Val Leu Ile Gln Lys Thr Asp Thr Gly Val
            85                  90                  95

Ser Asn Gln Thr Tyr Asp Asp Leu Leu Ala Lys Asp Cys His Cys Ile
            100                 105                 110

<210> SEQ ID NO 44
<211> LENGTH: 112
<212> TYPE: PRT
<213> ORGANISM: Artificial sequence
<220> FEATURE:
<223> OTHER INFORMATION: synthetic polypeptide

<400> SEQUENCE: 44

Ala Arg Asn Gly Thr His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Asn Lys Thr Asp Thr Gly Val
            85                  90                  95

Ser Leu Gln Thr Tyr Asp Asp Leu Leu Ala Lys Asp Cys His Cys Ile
            100                 105                 110

<210> SEQ ID NO 45
<211> LENGTH: 112
<212> TYPE: PRT
<213> ORGANISM: Artificial sequence
<220> FEATURE:
<223> OTHER INFORMATION: synthetic polypeptide

<400> SEQUENCE: 45

Ala Arg Asn Gly Thr His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Asn Val
            85                  90                  95

Ser Leu Gln Thr Tyr Asp Asp Leu Leu Ala Lys Asp Cys His Cys Ile
            100                 105                 110

<210> SEQ ID NO 46
<211> LENGTH: 112
<212> TYPE: PRT
<213> ORGANISM: Artificial sequence
<220> FEATURE:
<223> OTHER INFORMATION: synthetic polypeptide

<400> SEQUENCE: 46

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Asn Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Asn Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 47
<211> LENGTH: 112
<212> TYPE: PRT
<213> ORGANISM: Artificial sequence
<220> FEATURE:
<223> OTHER INFORMATION: synthetic polypeptide

<400> SEQUENCE: 47

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Asn Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Asn Val
                85                  90                  95

Ser Leu Gln Thr Tyr Asp Asp Leu Leu Ala Lys Asp Cys His Cys Ile
            100                 105                 110

<210> SEQ ID NO 48
<211> LENGTH: 112
<212> TYPE: PRT
<213> ORGANISM: Artificial sequence
<220> FEATURE:
<223> OTHER INFORMATION: synthetic polypeptide

<400> SEQUENCE: 48

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Asn Asp Thr Val Pro Ala Pro Cys Cys Val Pro
65                  70                  75                  80

```
Ala Ser Tyr Asn Pro Met Val Leu Ile Asn Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 49
<211> LENGTH: 112
<212> TYPE: PRT
<213> ORGANISM: Artificial sequence
<220> FEATURE:
<223> OTHER INFORMATION: synthetic polypeptide

<400> SEQUENCE: 49

```
Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
    50                  55                  60

Leu His Arg Leu Lys Asn Asp Thr Val Pro Ala Pro Cys Cys Val Pro
65                  70                  75                  80

Ala Ser Tyr Asn Pro Met Val Leu Ile Gln Lys Thr Asp Thr Asn Val
                85                  90                  95

Ser Leu Gln Thr Tyr Asp Asp Leu Leu Ala Lys Asp Cys His Cys Ile
            100                 105                 110
```

<210> SEQ ID NO 50
<211> LENGTH: 112
<212> TYPE: PRT
<213> ORGANISM: Artificial sequence
<220> FEATURE:
<223> OTHER INFORMATION: synthetic polypeptide

<400> SEQUENCE: 50

```
Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Asn Lys Thr Asp Thr Asn Val
                85                  90                  95

Ser Leu Gln Thr Tyr Asp Asp Leu Leu Ala Lys Asp Cys His Cys Ile
            100                 105                 110
```

<210> SEQ ID NO 51
<211> LENGTH: 112
<212> TYPE: PRT
<213> ORGANISM: Artificial sequence
<220> FEATURE:
<223> OTHER INFORMATION: synthetic polypeptide

<400> SEQUENCE: 51

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Asn Lys Thr Asp Thr Gly Val
                85                  90                  95

Ser Asn Gln Thr Tyr Asp Asp Leu Leu Ala Lys Asp Cys His Cys Ile
            100                 105                 110

<210> SEQ ID NO 52
<211> LENGTH: 112
<212> TYPE: PRT
<213> ORGANISM: Artificial sequence
<220> FEATURE:
<223> OTHER INFORMATION: synthetic polypeptide

<400> SEQUENCE: 52

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Asn Val
                85                  90                  95

Ser Asn Gln Thr Tyr Asp Asp Leu Leu Ala Lys Asp Cys His Cys Ile
            100                 105                 110

<210> SEQ ID NO 53
<211> LENGTH: 18
<212> TYPE: PRT
<213> ORGANISM: Artificial sequence
<220> FEATURE:
<223> OTHER INFORMATION: synthetic polypeptide

<400> SEQUENCE: 53

Met Lys Trp Val Thr Phe Ile Ser Leu Leu Phe Leu Phe Ser Ser Ala
1               5                   10                  15

Tyr Ser

<210> SEQ ID NO 54
<211> LENGTH: 6
<212> TYPE: PRT
<213> ORGANISM: Artificial sequence
<220> FEATURE:
<223> OTHER INFORMATION: synthetic polypeptide

<400> SEQUENCE: 54

Arg Gly Val Phe Arg Arg
1               5

<210> SEQ ID NO 55
<211> LENGTH: 112
<212> TYPE: PRT
<213> ORGANISM: Artificial sequence
<220> FEATURE:
<223> OTHER INFORMATION: synthetic polypeptide

<400> SEQUENCE: 55

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Gln Pro Asp Thr Val Pro Ala Pro Cys Cys Val Pro
65                  70                  75                  80

Ala Ser Tyr Asn Pro Met Val Leu Ile Gln Arg Thr Asp Thr Gly Val
                85                  90                  95

Ser Leu Gln Thr Tyr Asp Asp Leu Leu Ala Arg Asp Cys His Cys Ile
            100                 105                 110

<210> SEQ ID NO 56
<211> LENGTH: 112
<212> TYPE: PRT
<213> ORGANISM: Artificial sequence
<220> FEATURE:
<223> OTHER INFORMATION: synthetic polypeptide

<400> SEQUENCE: 56

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Gln Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Arg Thr Asp Thr Gly Val
                85                  90                  95

Ser Leu Gln Thr Tyr Asp Asp Leu Leu Ala Arg Asp Cys His Cys Ile
            100                 105                 110

<210> SEQ ID NO 57
<211> LENGTH: 112
<212> TYPE: PRT
<213> ORGANISM: Artificial sequence
<220> FEATURE:
<223> OTHER INFORMATION: synthetic polypeptide

<400> SEQUENCE: 57

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Gln Thr Ser
    50                  55                  60

Leu His Arg Leu Gln Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Arg Asp Cys His Cys Ile
            100                 105                 110

<210> SEQ ID NO 58
<211> LENGTH: 112
<212> TYPE: PRT
<213> ORGANISM: Artificial sequence
<220> FEATURE:
<223> OTHER INFORMATION: synthetic polypeptide

<400> SEQUENCE: 58

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Gln Thr Ser
    50                  55                  60

Leu His Arg Leu Gln Pro Asp Thr Val Pro Ala Pro Cys Cys Val Pro
65                  70                  75                  80

Ala Ser Tyr Asn Pro Met Val Leu Ile Gln Arg Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 59
<211> LENGTH: 112
<212> TYPE: PRT
<213> ORGANISM: Artificial sequence
<220> FEATURE:
<223> OTHER INFORMATION: synthetic polypeptide

<400> SEQUENCE: 59

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

```
Ala Ser Tyr Asn Pro Met Val Leu Ile Gln Arg Thr Asp Thr Gly Val
                85                  90                  95

Ser Leu Gln Thr Tyr Asp Asp Leu Leu Ala Arg Asp Cys His Cys Ile
            100                 105                 110
```

<210> SEQ ID NO 60
<211> LENGTH: 112
<212> TYPE: PRT
<213> ORGANISM: Artificial sequence
<220> FEATURE:
<223> OTHER INFORMATION: synthetic polypeptide

<400> SEQUENCE: 60

```
Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
    50                  55                  60

Leu His Arg Leu Gln Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Arg Asp Cys His Cys Ile
            100                 105                 110
```

<210> SEQ ID NO 61
<211> LENGTH: 112
<212> TYPE: PRT
<213> ORGANISM: Artificial sequence
<220> FEATURE:
<223> OTHER INFORMATION: synthetic polypeptide

<400> SEQUENCE: 61

```
Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
    50                  55                  60

Leu His Arg Leu Gln Pro Asp Thr Val Pro Ala Pro Cys Cys Val Pro
65                  70                  75                  80

Ala Ser Tyr Asn Pro Met Val Leu Ile Gln Arg Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 62
<211> LENGTH: 112
<212> TYPE: PRT
<213> ORGANISM: Artificial sequence
<220> FEATURE:
<223> OTHER INFORMATION: synthetic polypeptide -continued

```
<400> SEQUENCE: 62

Ala Arg Asn Gly Asp His Cys Pro Leu Gly Pro Gly Arg Cys Cys Arg
1               5                   10                  15

Leu Gln Ser Leu Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Gln Thr Ser
    50                  55                  60

Leu His Arg Leu Gln Pro Asp Thr Val Pro Ala Pro Cys Cys Val Pro
65                  70                  75                  80

Ala Ser Tyr Asn Pro Met Val Leu Ile Gln Arg Thr Asp Thr Gly Val
                85                  90                  95

Ser Leu Gln Thr Tyr Asp Asp Leu Leu Ala Arg Asp Cys His Cys Ile
            100                 105                 110

<210> SEQ ID NO 63
<211> LENGTH: 112
<212> TYPE: PRT
<213> ORGANISM: Artificial sequence
<220> FEATURE:
<223> OTHER INFORMATION: synthetic polypeptide

<400> SEQUENCE: 63

Ala Arg Asn Gly Asp His Cys Pro Leu Gly Pro Gly Arg Cys Cys Arg
1               5                   10                  15

Leu Gln Ser Leu Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Gln Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Arg Thr Asp Thr Gly Val
                85                  90                  95

Ser Leu Gln Thr Tyr Asp Asp Leu Leu Ala Arg Asp Cys His Cys Ile
            100                 105                 110

<210> SEQ ID NO 64
<211> LENGTH: 112
<212> TYPE: PRT
<213> ORGANISM: Artificial sequence
<220> FEATURE:
<223> OTHER INFORMATION: synthetic polypeptide

<400> SEQUENCE: 64

Ala Arg Asn Gly Asp His Cys Pro Leu Gly Pro Gly Arg Cys Cys Arg
1               5                   10                  15

Leu Gln Ser Leu Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Gln Thr Ser
    50                  55                  60

Leu His Arg Leu Gln Pro Asp Thr Val Pro Ala Pro Cys Cys Val Pro
65                  70                  75                  80
```

```
Ala Ser Tyr Asn Pro Met Val Leu Ile Gln Lys Thr Asp Thr Gly Val
                 85                  90                  95

Ser Leu Gln Thr Tyr Asp Asp Leu Leu Ala Arg Asp Cys His Cys Ile
            100                 105                 110
```

<210> SEQ ID NO 65
<211> LENGTH: 112
<212> TYPE: PRT
<213> ORGANISM: Artificial sequence
<220> FEATURE:
<223> OTHER INFORMATION: synthetic polypeptide

<400> SEQUENCE: 65

```
Ala Arg Asn Gly Asp His Cys Pro Leu Gly Pro Gly Arg Cys Cys Arg
1               5                   10                  15

Leu Gln Ser Leu Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Gln Thr Ser
    50                  55                  60

Leu His Arg Leu Gln Pro Asp Thr Val Pro Ala Pro Cys Cys Val Pro
65                  70                  75                  80

Ala Ser Tyr Asn Pro Met Val Leu Ile Gln Arg Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 66
<211> LENGTH: 11
<212> TYPE: PRT
<213> ORGANISM: Artificial sequence
<220> FEATURE:
<223> OTHER INFORMATION: synthetic polypeptide

<400> SEQUENCE: 66

```
Tyr Gly Arg Lys Lys Arg Arg Gln Arg Arg Arg
1               5                   10
```

<210> SEQ ID NO 67
<211> LENGTH: 12
<212> TYPE: PRT
<213> ORGANISM: Artificial sequence
<220> FEATURE:
<223> OTHER INFORMATION: synthetic polypeptide

<400> SEQUENCE: 67

```
Arg Arg Gln Arg Arg Thr Ser Lys Leu Met Lys Arg
1               5                   10
```

<210> SEQ ID NO 68
<211> LENGTH: 27
<212> TYPE: PRT
<213> ORGANISM: Artificial sequence
<220> FEATURE:
<223> OTHER INFORMATION: synthetic polypeptide

<400> SEQUENCE: 68

```
Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25
```

<210> SEQ ID NO 69
<211> LENGTH: 33
<212> TYPE: PRT
<213> ORGANISM: Artificial sequence
<220> FEATURE:
<223> OTHER INFORMATION: synthetic polypeptide

<400> SEQUENCE: 69

```
Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala
```

<210> SEQ ID NO 70
<211> LENGTH: 16
<212> TYPE: PRT
<213> ORGANISM: Artificial sequence
<220> FEATURE:
<223> OTHER INFORMATION: synthetic polypeptide

<400> SEQUENCE: 70

```
Arg Gln Ile Lys Ile Trp Phe Gln Asn Arg Arg Met Lys Trp Lys Lys
1               5                   10                  15
```

<210> SEQ ID NO 71
<211> LENGTH: 9
<212> TYPE: PRT
<213> ORGANISM: Artificial sequence
<220> FEATURE:
<223> OTHER INFORMATION: synthetic polypeptide

<400> SEQUENCE: 71

```
Arg Lys Lys Arg Arg Gln Arg Arg Arg
1               5
```

<210> SEQ ID NO 72
<211> LENGTH: 8
<212> TYPE: PRT
<213> ORGANISM: Artificial sequence
<220> FEATURE:
<223> OTHER INFORMATION: synthetic polypeptide

<400> SEQUENCE: 72

```
Arg Lys Lys Arg Arg Gln Arg Arg
1               5
```

<210> SEQ ID NO 73
<211> LENGTH: 11
<212> TYPE: PRT
<213> ORGANISM: Artificial sequence
<220> FEATURE:
<223> OTHER INFORMATION: synthetic polypeptide

<400> SEQUENCE: 73

```
Tyr Ala Arg Ala Ala Ala Arg Gln Ala Arg Ala
1               5                   10
```

<210> SEQ ID NO 74
<211> LENGTH: 11
<212> TYPE: PRT
<213> ORGANISM: Artificial sequence
<220> FEATURE:
<223> OTHER INFORMATION: synthetic polypeptide

<400> SEQUENCE: 74

Thr His Arg Leu Pro Arg Arg Arg Arg Arg
1               5                   10

<210> SEQ ID NO 75
<211> LENGTH: 11
<212> TYPE: PRT
<213> ORGANISM: Artificial sequence
<220> FEATURE:
<223> OTHER INFORMATION: synthetic polypeptide

<400> SEQUENCE: 75

Gly Gly Arg Arg Ala Arg Arg Arg Arg Arg
1               5                   10

<210> SEQ ID NO 76
<211> LENGTH: 51
<212> TYPE: DNA
<213> ORGANISM: Artificial sequence
<220> FEATURE:
<223> OTHER INFORMATION: synthetic polynucleotide

<400> SEQUENCE: 76
tggctccgag gtgccagatg tgatgcacac aagagtgagg ttgctcatcg g        51

<210> SEQ ID NO 77
<211> LENGTH: 39
<212> TYPE: DNA
<213> ORGANISM: Artificial sequence
<220> FEATURE:
<223> OTHER INFORMATION: synthetic polynucleotide

<400> SEQUENCE: 77
gctaccgcct ccacctaagc ctaaggcagc ttgacttgc                       39

<210> SEQ ID NO 78
<211> LENGTH: 90
<212> TYPE: DNA
<213> ORGANISM: Artificial sequence
<220> FEATURE:
<223> OTHER INFORMATION: synthetic polynucleotide

<400> SEQUENCE: 78
gctgccttag gcttaggtgg aggcggtagc ggtggaggtg ggagtggagg tggaggcagt    60
gcgcgcaacg gggaccactg tccgctcggg                                    90

<210> SEQ ID NO 79
<211> LENGTH: 53
<212> TYPE: DNA
<213> ORGANISM: Artificial sequence
<220> FEATURE:
<223> OTHER INFORMATION: synthetic polynucleotide

<400> SEQUENCE: 79
cagaggtcga ggtcggggga tcctcatatg cagtggcagt ctttggctaa caa        53

<210> SEQ ID NO 80
<211> LENGTH: 4
<212> TYPE: PRT
<213> ORGANISM: Artificial sequence
<220> FEATURE:
<223> OTHER INFORMATION: synthetic polypeptide

```
<400> SEQUENCE: 80

Arg Gly Arg Arg
1

<210> SEQ ID NO 81
<211> LENGTH: 6
<212> TYPE: PRT
<213> ORGANISM: Artificial sequence
<220> FEATURE:
<223> OTHER INFORMATION: synthetic polypeptide

<400> SEQUENCE: 81

Arg Lys Arg Lys Lys Arg
1               5

<210> SEQ ID NO 82
<211> LENGTH: 4
<212> TYPE: PRT
<213> ORGANISM: Artificial sequence
<220> FEATURE:
<223> OTHER INFORMATION: synthetic polypeptide

<400> SEQUENCE: 82

Arg Lys Lys Arg
1

<210> SEQ ID NO 83
<211> LENGTH: 6
<212> TYPE: PRT
<213> ORGANISM: Artificial sequence
<220> FEATURE:
<223> OTHER INFORMATION: synthetic polypeptide

<400> SEQUENCE: 83

Arg Arg Arg Lys Lys Arg
1               5

<210> SEQ ID NO 84
<211> LENGTH: 4
<212> TYPE: PRT
<213> ORGANISM: Artificial sequence
<220> FEATURE:
<223> OTHER INFORMATION: synthetic polypeptide

<400> SEQUENCE: 84

Gly Gly Ser Gly
1

<210> SEQ ID NO 85
<211> LENGTH: 5
<212> TYPE: PRT
<213> ORGANISM: Artificial sequence
<220> FEATURE:
<223> OTHER INFORMATION: synthetic polypeptide

<400> SEQUENCE: 85

Gly Gly Ser Gly Gly
1               5

<210> SEQ ID NO 86
<211> LENGTH: 5
<212> TYPE: PRT
<213> ORGANISM: Artificial sequence
<220> FEATURE:
<223> OTHER INFORMATION: synthetic polypeptide
```

```
<400> SEQUENCE: 86

Gly Ser Gly Ser Gly
1               5

<210> SEQ ID NO 87
<211> LENGTH: 5
<212> TYPE: PRT
<213> ORGANISM: Artificial sequence
<220> FEATURE:
<223> OTHER INFORMATION: synthetic polypeptide

<400> SEQUENCE: 87

Gly Ser Gly Gly Gly
1               5

<210> SEQ ID NO 88
<211> LENGTH: 5
<212> TYPE: PRT
<213> ORGANISM: Artificial sequence
<220> FEATURE:
<223> OTHER INFORMATION: synthetic polypeptide

<400> SEQUENCE: 88

Gly Gly Gly Ser Gly
1               5

<210> SEQ ID NO 89
<211> LENGTH: 5
<212> TYPE: PRT
<213> ORGANISM: Artificial sequence
<220> FEATURE:
<223> OTHER INFORMATION: synthetic polypeptide

<400> SEQUENCE: 89

Gly Ser Ser Ser Gly
1               5
```

GDF15 MUTEIN POLYPEPTIDES

CROSS-REFERENCE TO RELATED APPLICATIONS

This application claims priority benefit of U.S. provisional application Ser. No. 61/758,456, filed Jan. 30, 2013, which application is incorporated herein by reference in its entirety.

FIELD OF THE INVENTION

The present invention relates to, among other things, growth differentiation factor muteins and modifications thereof which are useful in treating obesity, diabetes and other metabolic-related disorders.

BACKGROUND

Obesity is most commonly caused by excessive food intake coupled with limited energy expenditure and/or lack of physical exercise. Obesity increases the likelihood of development of various diseases, such as diabetes mellitus, hypertension, atherosclerosis, coronary artery disease, sleep apnea, gout, rheumatism and arthritis. Moreover, mortality risk directly correlates with obesity, such that, for example, a body-mass index in excess of 40 results in an average decreased life expectancy of more than 10 years.

Current pharmacological treatment modalities include appetite suppressors targeting receptor classes (e.g., CB1, $5\text{-HT}_{2C}$, and NPY); regulators of the appetite circuits in the hypothalamus and the molecular actions of ghrelin; and nutrient-absorption inhibitors targeting lipases. Unfortunately, none of the current modalities has been shown to effectively treat obesity without causing adverse effects, some of which can be very severe.

High blood glucose levels stimulate the secretion of insulin by pancreatic beta-cells. Insulin in turn stimulates the entry of glucose into muscles and adipose cells, leading to the storage of glycogen and triglycerides and to the synthesis of proteins. Activation of insulin receptors on various cell types diminishes circulating glucose levels by increasing glucose uptake and utilization, and by reducing hepatic glucose output. Disruptions within this regulatory network can result in diabetes and associated pathologic syndromes that affect a large and growing percentage of the human population.

Patients who have a glucose metabolism disorder can suffer from hyperglycemia, hyperinsulinemia, and/or glucose intolerance. An example of a disorder that is often associated with the aberrant levels of glucose and/or insulin is insulin resistance, in which liver, fat, and muscle cells lose their ability to respond to normal blood insulin levels.

In view of the prevalence and severity of obesity, diabetes and associated metabolic and non-metabolic disorders, along with the shortcomings of current treatment options, alternative treatment modalities that modulate, for example, appetite, glucose and/or insulin levels and enhance the biological response to fluctuating glucose levels in a patient remain of interest.

In addition, in the pharmaceutical sciences it is frequently beneficial, and sometimes imperative, to improve one of more physical properties of the treatment modality (e.g., a protein, peptide, or hydrophobic molecule) of interest and/or the manner in which it is administered. Improvements of physical properties include, for example, methods of increasing water solubility, bioavailability, serum half-life, and/or therapeutic half-life; modulating immunogenicity and/or biological activity; and/or extending the circulation time. Such improvements must be imparted without adversely impacting the bioactivity of the treatment modality. Thus, it may be advantageous for alternatives to current treatment options for obesity, diabetes and associated metabolic and non-metabolic disorders, to possess one or more improved physical properties.

SUMMARY

The present disclosure contemplates the use of the agents described herein, and compositions thereof, to treat and/or prevent various diseases, disorders and conditions, and/or the symptoms thereof. In some embodiments, the diseases, disorders and conditions, and/or the symptoms thereof, relate to glucose metabolism disorders and other metabolic-related disorders, whereas in other embodiments they relate to body weight disorders. By way of example, but not limitation, the agents, and compositions thereof, can be used for the treatment and/or prevention of diabetes mellitus (e.g., Type 2 diabetes), insulin resistance and diseases, disorders and conditions characterized by insulin resistance, decreased insulin production, hyperglycemia, hypoinsulinemia, and metabolic syndrome. The agents, and compositions thereof, can also be used for the treatment and/or prevention of obesity and other body weight disorders by, for example, effecting appetite suppression.

In certain embodiments, the agents are human Growth Differentiation Factor 15 (GDF15)—related polypeptides, and homologues, variants (e.g., muteins), fragments and other modified forms thereof. In particular embodiments, the agents contemplated by the present disclosure are modified human GDF15 molecules, whereas in other embodiments the agents are modified GDF15 muteins. The present disclosure also contemplates nucleic acid molecules encoding the foregoing. For the sake of convenience, the modified human GDF15 molecules and the modified GDF15 variants (e.g., muteins) described henceforward are collectively referred to hereafter as the "Polypeptide(s)". It should be noted that any reference to "human" in connection with the polypeptides and nucleic acid molecules of the present disclosure is not meant to be limiting with respect to the manner in which the polypeptide or nucleic acid is obtained or the source, but rather is only with reference to the sequence as it may correspond to a sequence of a naturally occurring human polypeptide or nucleic acid molecule. In addition to the human polypeptides and the nucleic acid molecules which encode them, the present disclosure contemplates GDF15—related polypeptides and corresponding nucleic acid molecules from other species.

The present disclosure also contemplates other GDF15—related agents capable of eliciting a biological response comparable to (or greater than) that of the Polypeptides, and/or agents capable of enhancing the activity of the Polypeptides.

In some embodiments of the present disclosure, a subject having, or at risk of having, a disease or disorder treatable by one or more Polypeptides is administered in an amount effective for treating the disease or disorder. In some embodiments, the disease or disorder is a hyperglycemic condition, insulin resistance, hyperinsulinemia, glucose intolerance or metabolic syndrome. In other embodiments the disease or disorder is a body weight disorder (e.g., obesity), while in still other embodiments the Polypeptides cause, to at least some extent, appetite suppression.

Other aspects of the present disclosure include cell-based expression systems, vectors, engineered cell lines, and methods and uses related to the foregoing.

As described in detail hereafter, one embodiment of the present disclosure relates to a polypeptide comprising a) a polypeptide comprising at least one modification to the sequence depicted in FIG. 1B (SEQ ID NO:3); wherein the modification does not alter the amino acid sequence of the polypeptide, or b) a mutein polypeptide of the sequence depicted in FIG. 1B (SEQ ID NO:3), wherein the mutein polypeptide comprises at least one modification that does not alter the amino acid sequence of the mutein polypeptide; and wherein the modification set forth in a) and b) improves at least one physical property of the polypeptide or the mutein polypeptide.

In certain embodiments of the present disclosure, a polypeptide comprises a mutein polypeptide of any one of the sequences depicted in FIG. 3, FIG. 5 or FIG. 6.

In some embodiments, the polypeptide has a length of from about 10 amino acids to about 113 amino acids. In other embodiments, a polypeptide of the present disclosure may have fewer than 100 amino acid residues, fewer than 75 amino acid residues, fewer than 50 amino acid residues, fewer than 25 amino acid residues, or fewer than 20 amino acid residues.

In still further embodiments, a polypeptide of the present disclosure comprises an amino acid sequence having at least 85% amino acid identity, at least 90% amino acid identity, at least 93% amino acid identity, at least 95% amino acid identity, at least 97% amino acid identity, at least 98% amino acid identity, or at least 99% amino acid identity to the amino acid sequence depicted in FIG. 1B (SEQ ID NO:3)

According to the present disclosure, the polypeptide may be produced recombinantly.

In some embodiments of the present disclosure, the modification to a polypeptide comprises pegylation, glycosylation, polysialylation, hesylation, albumin fusion, albumin binding through a conjugated fatty acid chain, Fc-fusion, or fusion with a PEG mimetic.

In particular embodiments, the modification to a polypeptide comprises glycosylation, and in some of those embodiments the glycosylation is N-glycosylation. The N-glycosylation may occur at more than one amino acid residue of the polypeptide.

In other embodiments, the modification to a polypeptide comprises an albumin fusion wherein an albumin, an albumin variant, or an albumin fragment is conjugated to the polypeptide. In some embodiments, the albumin, albumin variant, or albumin fragment is human serum albumin (HSA), a human serum albumin variant, or a human serum albumin fragment, whereas in other embodiments the albumin, albumin variant, or albumin fragment is bovine serum albumin, a bovine serum albumin variant, or a bovine serum albumin fragment.

The full-length HSA has a signal peptide of 18 amino acids (MKWVTFISLLFLFSSAYS; SEQ ID NO:53) followed by a pro-domain of 6 amino acids (RGVFRR; SEQ ID NO:54); this 24 amino acid residue peptide may be referred to as the pre-pro domain. The mature HSA polypeptide spans residues D25-L609 of the sequence depicted in FIG. 1C (SEQ ID NO:5). In a construct used to generate the experimental data presented herein, the endogenous signal peptide was replaced with human IgK signal peptide, and the endogenous pro-domain was left out entirely.

In still further embodiments, the albumin, albumin variant, or albumin fragment is conjugated to the polypeptide at the carboxyl terminus, the amino terminus, both the carboxyl and amino termini, or internally. Particular embodiments entail conjugation of the albumin, albumin variant, or albumin fragment to the polypeptide at the amino terminus.

In particular embodiments, the albumin, albumin variant, or albumin fragment is conjugated to a polypeptide comprising the 167 amino acid pro-domain and the 112 amino acid mature domain of the 308 amino acid GDF15 precursor polypeptide; thus, the present disclosure contemplates a GDF15 polypeptide that has a length of from about amino acid residue 30 to about amino acid residue 308 of the sequence depicted in FIG. 1A (SEQ ID NO:1).

The present disclosure contemplates albumin fusion molecules wherein the albumin, albumin variant, or albumin fragment is conjugated to the polypeptide via a linker. Examples of suitable linkers are described herein. By way of example, the linker may be a peptide linker of, for example, four-to-six amino acids. In some embodiments, the linker is a non-cleavable linker (e.g., a 3x(4Gly-Ser) linker). In other embodiments, the linker is a cleavable linker, and in further embodiments the cleavable linker can be cleaved by a protease (e.g., a 2x(4Gly-Ser) Factor Xa-cleavable linker.

In particular embodiments, the albumin, albumin variant, or albumin fragment of an albumin fusion molecule is excised prior to the albumin fusion molecule being secreted from a cell, whereas in other embodiments the albumin fusion molecule is excised subsequent to the albumin fusion molecule being secreted from a cell.

The present disclosure encompasses embodiments wherein the physical property of the recited polypeptide is selected from the group consisting of solubility, bioavailability, serum half-life, therapeutic half-life, circulation time, and immunogenicity. In particular embodiments, the physical property is solubility.

Furthermore, the present disclosure contemplates nucleic acid molecules encoding the aforementioned polypeptides. In some embodiments, a nucleic acid molecule is operably linked to an expression control element that confers expression of the nucleic acid molecule encoding the polypeptide in vitro, in a cell or in vivo.

In some embodiments, a vector (e.g., a viral vector) contains one or more of the nucleic acid molecules.

Some embodiments include transformed or host cells that express one or more of the aforementioned polypeptides.

In particular embodiments of the present disclosure, one or more of the aforementioned polypeptides is formulated to yield a pharmaceutical composition, wherein the composition also includes one or more pharmaceutically acceptable diluents, carriers or excipients. In certain embodiments, a pharmaceutical composition also includes at least one additional prophylactic or therapeutic agent.

Still further embodiments of the present disclosure comprise an antibody that binds specifically to one of the aforementioned mutein polypeptides. In some embodiments, the antibody comprises a light chain variable region and a heavy chain variable region present in separate polypeptides or in a single polypeptide. An antibody of the present disclosure binds the polypeptide with an affinity of from about $10^7$ M$^{-1}$ to about $10^{12}$ M$^{-1}$ in certain embodiments. In still other embodiments, the antibody comprises a heavy chain constant region of the isotype IgG1, IgG2, IgG3, or IgG4. In additional embodiments, the antibody is detectably labeled, while it is a Fv, scFv, Fab, F(ab')$_2$, or Fab' in other embodiments.

The present disclosure also contemplates antibodies that comprise a covalently linked non-polypeptide polymer (e.g., a poly(ethylene glycol) polymer). In other embodiments, the antibody comprises a covalently linked moiety selected from a lipid moiety, a fatty acid moiety, a polysaccharide moiety, and a carbohydrate moiety.

The antibody is a single chain Fv (scFv) antibody in some embodiments, and the scFv is multimerized in others.

The antibodies of the present disclosure may be, but are not limited to, monoclonal antibodies, polyclonal antibodies, or humanized antibodies.

Furthermore, the present disclosure contemplates pharmaceutical compositions comprising an antibody as described above formulated with at least one pharmaceutically acceptable excipient, carrier or diluent. Such pharmaceutical compositions may also contain at least one additional prophylactic or therapeutic agent.

Certain embodiments of the present disclosure contemplate a sterile container that contains one of the above-mentioned pharmaceutical compositions and optionally one or more additional components. By way of example, but not limitation, the sterile container may be a syringe. In still further embodiments, the sterile container is one component of a kit; the kit may also contain, for example, a second sterile container that contains at least one prophylactic or therapeutic agent.

The present disclosure also contemplates a method of treating or preventing a glucose metabolism disorder in a subject (e.g., a human) by administering to the subject a therapeutically effective amount of a polypeptide. In some methods, the treating or preventing results in a reduction in plasma glucose in the subject, a reduction in plasma insulin in the subject, a reduction in body weight and/or food intake, or an increase in glucose tolerance in the subject. In particular embodiments, the glucose metabolism disorder is diabetes mellitus. In some embodiments, the subject is obese and/or has a body weight disorder.

Though not limited to any particular route of administration or dosing regimen, in some embodiments the administering is by parenteral (e.g., subcutaneous) injection.

BRIEF DESCRIPTION OF THE DRAWINGS

FIG. 1A depicts the human GDF15 precursor amino acid sequence and the corresponding nucleic acid encoding the human GDF15 precursor amino acid sequence.

FIG. 1B depicts the mature human GDF15 amino acid sequence and the corresponding nucleic acid sequence encoding mature human GDF15.

FIG. 1C depicts a human serum albumin precursor sequence comprising endogenous signal peptide and pro-domain, and mature human serum albumin (D25-L609), and the corresponding nucleic acid sequence; and a human serum albumin precursor sequence comprising IgK signal peptide and mature human serum albumin (D25-L609), and the corresponding nucleic acid sequence.

FIG. 1D depicts the mature human serum albumin amino acid sequence (subsequence of the amino acid sequence of FIG. 1C lacking the IgK Signal Peptide, and the corresponding nucleic acid sequence.

FIG. 1E depicts a fusion molecule wherein the human serum albumin amino acid sequence having an IgK signal sequence is fused to the N-terminus of the mature human GDF15 amino acid sequence through a protease-sensitive 2x(4Gly-Ser) Factor Xa-cleavable linker, and the corresponding nucleic acid encoding the fusion molecule.

FIG. 1F depicts a fusion molecule wherein the mature human serum albumin amino acid sequence is fused to the N-terminus of the mature human GDF15 amino acid sequence through a protease-sensitive 2x(4Gly-Ser) Factor Xa-cleavable linker, and the corresponding nucleic acid encoding the fusion molecule.

FIG. 1G depicts a fusion molecule wherein the human serum albumin amino acid sequence having an IgK signal sequence is fused to the N-terminus of the mature human GDF15 amino acid sequence through a non-cleavable 3x(4Gly-Ser) linker, and the corresponding nucleic acid encoding the fusion molecule.

FIG. 1H depicts a fusion molecule wherein the mature human serum albumin amino acid sequence is fused to the N-terminus of the mature human GDF15 amino acid sequence through a non-cleavable 3x(4Gly-Ser) linker, and the corresponding nucleic acid encoding the fusion molecule.

FIGS. 2A-2C depict the effect on body weight (FIG. 2A), food take (FIG. 2B), and blood glucose (FIG. 2C) in ob/ob mice following administration of the fusion molecule described in FIG. 1H as a single subcutaneous dose at the indicated concentrations (PBS (vehicle), 0.04 mg/kg, 0.12 mg/kg, 0.4 mg/kg, and 1.2 mg/kg). As noted in the figure, the indicated parameters were determined on various days over a 22-day period. In each group of mice, n=7 and p-values (*, p<0.05; , p<0.01; *, p<0.001) were determined by student's unpaired T-test comparing the body weight, food intake and blood glucose groups at the various concentrations to vehicle control group at each specified time point.

FIG. 3 depicts the amino acid sequences of the GDF15 muteins generated via mutagenesis of predicted solvent-accessible hydrophobic residues within mature human GDF15. Fusion molecules were generated wherein each GDF15 mutein sequence was fused to HSA through the linker depicted in FIG. 1H (a non-cleavable 3x(4Gly-Ser linker) linker); the sequences set forth in FIG. 3 neither depict the HSA component nor the linker component of the fusion molecules.

FIG. 4 is a table summarizing whether each GDF15 mutein set forth in FIG. 3 is secreted as a disulfide-linked homodimer.

FIG. 5 depicts the amino acid sequences of GDF15 muteins having alanine substitutions for evaluation of their improvement in physical properties relative to GDF15.

FIG. 6 depicts the amino acid sequences of single-point glycosylation muteins and additional di-glycosylation muteins for introduction of N-linked glycosylation consensus sites (Asn-Xxx-Ser/Thr) for evaluation of improved physical properties relative to GDF15. Fusion molecules were generated wherein each GDF15 mutein sequence was fused to HSA through the linker depicted in FIG. 1E (a Factor Xa-cleavable linker); the sequences set forth in FIG. 6 neither depict the HSA component nor the linker component of the fusion molecules.

FIG. 7 provides a summary of secretion and dimer formation data, along with N-glycan site occupancy, for each engineered N-glycosylated human GDF15 mutein set forth in FIG. 6.

FIG. 8 sets forth engineered human GDF15 muteins, post-Factor Xa cleavage and purification, having improved physical properties compared to mature human GDF15.

FIG. 9 depicts the effect on overnight food intake reduction in ob/ob mice following a single, subcutaneous acute dose of 0.3 mg/kg of mature human GDF15, N-glycosylated human GDF15 muteins, and vehicle (PBS) control. In each group of mice, n=7 and p-values (*, p<0.05; , p<0.01; *, p<0.001) were determined by student's unpaired T-test comparing food intake of GDF15 mutein-treated mice relative to vehicle control group.

FIG. 10 indicates that the hydrodynamic radii of GDF15 N-Glycan muteins are increased relative to mature human GDF15, as determined by analytical gel filtration chromatography measuring elution time.

DETAILED DESCRIPTION

Before the present disclosure is further described, it is to be understood that the disclosure is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

It must be noted that as used herein and in the appended claims, the singular forms "a," "an," and "the" include plural referents unless the context clearly dictates otherwise. Thus, for example, reference to "the Human Polypeptide" includes reference to one or more Human Polypeptides, and so forth. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Overview

The present disclosure contemplates the use of the agents described herein, and compositions thereof, to treat and/or prevent various diseases, disorders and conditions, and/or the symptoms thereof. In some embodiments, the diseases, disorders and conditions, and/or the symptoms thereof, pertain to glucose metabolism disorders, while in other embodiments they pertain to body weight disorders. By way of example, but not limitation, the agents, and compositions thereof, can be used for the treatment and/or prevention of Type 2 diabetes, insulin resistance and diseases, disorders and conditions characterized by insulin resistance, decreased insulin production, hyperglycemia, metabolic syndrome, or obesity.

In particular embodiments, the agents contemplated by the present disclosure are modified human Growth Differentiation Factor 15 (GDF15), whereas in other embodiments the agents are modified GDF15 variants (e.g., muteins). The modified human GDF15 and modified GDF15 variants (e.g., muteins) have sufficient homology to human GDF15 such that they have the ability to bind the GDF15 receptor(s) and initiate a signal transduction pathway resulting in, for example, reduced body weight and/or the other physiological effects described herein. The present disclosure also contemplates nucleic acid molecules encoding the foregoing. As indicated above, the modified human GDF15 molecules and the modified GDF15 variants described henceforward are collectively referred to as the "Polypeptide(s)".

Examples of various GDF15 muteins that may be modified are described hereafter. In some embodiments, one or more GDF15 amino acid residues are substituted with another amino acid. In other embodiments, one or more GDF15 native lysine residues are substituted with another amino acid (however, changes involving K62Q are inactive). In some embodiments of the present disclosure, alanine scanning may be used to generate GDF15 muteins, and modifications to those muteins can then be assessed for their ability to enhance one or more desirable properties of the muteins themselves. Examples of modified GDF15 molecules and modified GDF15 muteins are described hereafter.

The present disclosure contemplates modifications to GDF15 and GDF15 muteins, including, for example, pegylation, glycosylation, and albumin conjugates. In particular embodiments, strategies are employed such that pegylation is effected only at specific lysine residues (i.e., site-specific pegylation). In other embodiments, albumin fusions may be generated whereby mature albumin, or an altered form thereof (e.g., a fragment), is conjugated directly or indirectly (e.g., via a linker) to GDF15 or a GDF15 mutein. As alluded to above, the modifications may, for example, improve the serum half-life and/or the solubility of the Polypeptides. Examples of particular modified GDF15 molecules and modified GDF15 muteins are described hereafter.

Definitions

The terms "patient" or "subject" are used interchangeably to refer to a human or a non-human animal (e.g., a mammal).

The terms "treat", "treating", treatment" and the like refer to a course of action (such as administering a Polypeptide or a pharmaceutical composition comprising a Polypeptide) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (i.e., arresting the development or further development of the disease, disorder or condition or clinical symptoms association therewith) an active disease (e.g., so as to decrease the level of insulin and/or glucose in the bloodstream, to increase glucose tolerance so as to minimize fluctuation of glucose levels, and/or so as to protect against diseases caused by disruption of glucose homeostasis).

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering a Polypeptide or a pharmaceutical composition comprising a Polypeptide) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as a part of a pharmaceutical composition and either in a single dose or as part of a series of doses, in an amount that is capable of having any detectable, positive effect on any symptom, aspect, or characteristics of a disease, disorder or condition when administered to a patient. The therapeutically effective amount can be ascertained by measuring relevant physiological effects. For example, in the case of a hyperglycemic condition, a lowering or reduction of blood glucose or an improvement in glucose tolerance test can be used to determine whether the amount of an agent is effective to treat the hyperglycemic condition. For example, a therapeutically effective amount is an amount sufficient to reduce or decrease any level (e.g., a baseline level) of fasting plasma glucose (FPG), wherein, for example, the amount is sufficient to reduce a FPG level greater than 200 mg/dl to less than 200 mg/dl, wherein the amount is sufficient to reduce a FPG level between 175 mg/dl and 200 mg/dl to less than the starting level, wherein the amount is sufficient to reduce a FPG level between 150 mg/dl and 175 mg/dl to less than the starting level, wherein the amount is sufficient to reduce a FPG level between 125 mg/dl and 150 mg/dl to less than the starting level, and so on (e.g., reducing FPG levels to less than 125 mg/dl, to less than 120 mg/dl, to less than 115 mg/dl, to less than 110 mg/dl, etc.). In the case of HbAlc levels, the effective amount is an amount sufficient to reduce or decrease levels by more than about 10% to 9%, by more than about 9% to 8%, by more than about 8% to 7%, by more than about 7% to 6%, by more than about 6% to 5%, and so on. More particularly, a reduction or decrease of HbAlc levels by about 0.1%, 0.25%, 0.4%, 0.5%, 0.6%, 0.7%, 0.8%, 0.9%, 1%, 1.5%, 2%, 3%, 4%, 5%, 10%, 20%, 30%, 33%, 35%, 40%, 45%, 50%, or more is contemplated by the present disclosure. The therapeutically effective amount can be adjusted in connection with the dosing regimen and diagnostic analysis of the subject's condition and the like.

The phrase "in a sufficient amount to effect a change" means that there is a detectable difference between a level of an indicator measured before (e.g., a baseline level) and after administration of a particular therapy. Indicators include any objective parameter (e.g., level of glucose or insulin) or subjective parameter (e.g., a subject's feeling of well-being).

The phrase "glucose tolerance", as used herein, refers to the ability of a subject to control the level of plasma glucose and/or plasma insulin when glucose intake fluctuates. For example, glucose tolerance encompasses the subject's ability to reduce, within about 120 minutes, the level of plasma glucose back to a level determined before the intake of glucose.

Broadly speaking, the terms "diabetes" and "diabetic" refer to a progressive disease of carbohydrate metabolism involving inadequate production or utilization of insulin, frequently characterized by hyperglycemia and glycosuria. The terms "pre-diabetes" and "pre-diabetic" refer to a state wherein a subject does not have the characteristics, symptoms and the like typically observed in diabetes, but does have characteristics, symptoms and the like that, if left untreated, may progress to diabetes. The presence of these conditions may be determined using, for example, either the fasting plasma glucose (FPG) test or the oral glucose tolerance test (OGTT). Both usually require a subject to fast for at least 8 hours prior to initiating the test. In the FPG test, a subject's blood glucose is measured after the conclusion of the fasting; generally, the subject fasts overnight and the blood glucose is measured in the morning before the subject eats. A healthy subject would generally have a FPG concentration between about 90 and about 100 mg/dl, a subject with "pre-diabetes" would generally have a FPG concentration between about 100 and about 125 mg/dl, and a subject with "diabetes" would generally have a FPG level above about 126 mg/dl. In the OGTT, a subject's blood glucose is measured after fasting and again two hours after drinking a glucose-rich beverage. Two hours after consumption of the glucose-rich beverage, a healthy subject generally has a blood glucose concentration below about 140 mg/dl, a pre-diabetic subject generally has a blood glucose concentration about 140 to about 199 mg/dl, and a diabetic subject generally has a blood glucose concentration about 200 mg/dl or above. While the aforementioned glycemic values pertain to human subjects, normoglycemia, moderate hyperglycemia and overt hyperglycemia are scaled differently in murine subjects. A healthy murine subject after a four-hour fast would generally have a FPG concentration between about 100 and about 150 mg/dl, a murine subject with "pre-diabetes" would generally have a FPG concentration between about 175 and about 250 mg/dl and a murine subject with "diabetes" would generally have a FPG concentration above about 250 mg/dl.

The term "insulin resistance" as used herein refers to a condition where a normal amount of insulin is unable to produce a normal physiological or molecular response. In some cases, a hyper-physiological amount of insulin, either endogenously produced or exogenously administered, is able to overcome the insulin resistance, in whole or in part, and produce a biologic response.

The term "metabolic syndrome" refers to an associated cluster of traits that includes, but is not limited to, hyperinsulinemia, abnormal glucose tolerance, obesity, redistribution of fat to the abdominal or upper body compartment, hypertension, dysfibrinolysis, and dyslipidemia characterized by high triglycerides, low high density lipoprotein (HDL)-cholesterol, and high small dense low density lipoprotein (LDL) particles. Subjects having metabolic syndrome are at risk for development of Type 2 diabetes and/or other disorders (e.g., atherosclerosis).

The phrase "glucose metabolism disorder" encompasses any disorder characterized by a clinical symptom or a combination of clinical symptoms that is associated with an elevated level of glucose and/or an elevated level of insulin in a subject relative to a healthy individual. Elevated levels of glucose and/or insulin may be manifested in the following diseases, disorders and conditions: hyperglycemia, type II diabetes, gestational diabetes, type I diabetes, insulin resistance, impaired glucose tolerance, hyperinsulinemia, impaired glucose metabolism, pre-diabetes, other metabolic disorders (such as metabolic syndrome, which is also referred to as syndrome X), and obesity, among others. The Polypeptides of the present disclosure, and compositions thereof, can be used, for example, to achieve and/or maintain glucose homeostasis, e.g., to reduce glucose level in the bloodstream and/or to reduce insulin level to a range found in a healthy subject.

The term "hyperglycemia", as used herein, refers to a condition in which an elevated amount of glucose circulates in the blood plasma of a subject relative to a healthy individual. Hyperglycemia can be diagnosed using methods known in the art, including measurement of fasting blood glucose levels as described herein.

The term "hyperinsulinemia", as used herein, refers to a condition in which there are elevated levels of circulating insulin when, concomitantly, blood glucose levels are either elevated or normal. Hyperinsulinemia can be caused by insulin resistance which is associated with dyslipidemia, such as high triglycerides, high cholesterol, high low-density lipoprotein (LDL) and low high-density lipoprotein (HDL); high uric acids levels; polycystic ovary syndrome; type II diabetes and obesity. Hyperinsulinemia can be diagnosed as having a plasma insulin level higher than about 2 µU/mL.

As used herein, the phrase "body weight disorder" refers to conditions associated with excessive body weight and/or enhanced appetite. Various parameters are used to determine whether a subject is overweight compared to a reference healthy individual, including the subject's age, height, sex and health status. For example, a subject may be considered overweight or obese by assessment of the subject's Body Mass Index (BMI), which is calculated by dividing a subject's weight in kilograms by the subject's height in meters squared. An adult having a BMI in the range of ~18.5 to ~24.9 kg/m$^2$ is considered to have a normal weight; an adult having a BMI between ~25 and ~29.9 kg/m$^2$ may be considered overweight (pre-obese); and an adult having a BMI of ~30 kg/m$^2$ or higher may be considered obese. Enhanced appetite frequently contributes to excessive body weight. There are several conditions associated with enhanced appetite, including, for example, night eating syndrome, which is characterized by morning anorexia and evening polyphagia often associated with insomnia, but which may be related to injury to the hypothalamus.

The term "Activators" refers to agents that, for example, stimulate, increase, activate, facilitate, enhance activation, sensitize or up-regulate the function or activity of one or more Polypeptides. In addition, Activators include agents that operate through the same mechanism of action as the Polypeptides (i.e., agents that modulate the same signaling pathway as the Polypeptides in a manner analogous to that of the Polypeptides) and are capable of eliciting a biological response comparable to (or greater than) that of the Polypeptides. Examples of Activators include agonists such as small molecule compounds.

The term "Modulators" collectively refers to the Polypeptides and the Activators.

The terms "modulate", "modulation" and the like refer to the ability of an agent (e.g., an Activator) to increase the function or activity of one or more Polypeptides (or the nucleic acid molecules encoding them), either directly or indirectly; or to the ability of an agent to produce an effect comparable to that of one or more Polypeptides.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence, fusion proteins with heterologous and homologous leader sequences, with or without N-terminus methionine residues; immunologically tagged proteins; and the like.

It will be appreciated that throughout this disclosure reference is made to amino acids according to the single letter or three letter codes. For the reader's convenience, the single and three letter amino acid codes are provided below:

| G | Glycine | Gly | P | Proline | Pro |
|---|---|---|---|---|---|
| A | Alanine | Ala | V | Valine | Val |
| L | Leucine | Leu | I | Isoleucine | Ile |
| M | Methionine | Met | C | Cysteine | Cys |
| F | Phenylalanine | Phe | Y | Tyrosine | Tyr |
| W | Tryptophan | Trp | H | Histidine | His |
| K | Lysine | Lys | R | Arginine | Arg |
| Q | Glutamine | Gln | N | Asparagine | Asn |
| E | Glutamic Acid | Glu | D | Aspartic Acid | Asp |
| S | Serine | Ser | T | Threonine | Thr |

As used herein, the term "variant" encompasses naturally-occurring variants (e.g., homologs and allelic variants) and non-naturally-occurring variants (e.g., muteins). Naturally-occurring variants include homologs, i.e., nucleic acids and polypeptides that differ in nucleotide or amino acid sequence, respectively, from one species to another. Naturally-occurring variants include allelic variants, i.e., nucleic acids and polypeptides that differ in nucleotide or amino acid sequence, respectively, from one individual to another within a species. Non-naturally-occurring variants include nucleic acids and polypeptides that comprise a change in nucleotide or amino acid sequence, respectively, where the change in sequence is artificially introduced, e.g., the change is generated in the laboratory or other facility by human intervention ("hand of man").

The term "native", in reference to GDF15, refers to biologically active, naturally-occurring GDF15, including biologically active, naturally-occurring GDF15 variants. The term includes the 112 amino acid human GDF15 mature sequence.

The term "muteins" as used herein refers broadly to mutated recombinant proteins, i.e., a polypeptide comprising an artificially introduced change in amino acid sequence, e.g., a change in amino acid sequence generated in the laboratory or other facility by human intervention ("hand of man"). These proteins usually carry single or multiple amino acid substitutions and are frequently derived from cloned genes that have been subjected to site-directed or random mutagenesis, or from completely synthetic genes.

As used herein in reference to native human GDF15 or a GDF15 mutein, the terms "modified", "modification" and the like refer to one or more changes that enhance a desired property of human GDF15, a naturally-occurring GDF15 variant, or a GDF15 mutein, where the change does not alter the primary amino acid sequence of the GDF15. "Modification" includes a covalent chemical modification that does not alter the primary amino acid sequence of the GDF15 polypeptide itself. Such desired properties include, for example, enhancing solubility, prolonging the circulation half-life, increasing the stability, reducing the clearance, altering the immunogenicity or allergenicity, improving aspects of manufacturability (e.g., cost and efficiency), and enabling the raising of particular antibodies (e.g., by introduction of unique epitopes) for use in detection assays. Changes to human GDF15, a naturally-occurring GDF15 variant, or a GDF15 mutein that may be carried out include, but are not limited to, pegylation (covalent attachment of one or more molecules of polyethylene glycol (PEG), or derivatives thereof); glycosylation (e.g., N-glycosylation), polysialylation and hesylation; albumin fusion; albumin binding through, for example, a conjugated fatty acid chain (acylation); Fc-fusion; and fusion with a PEG mimetic. Some particular embodiments entail modifications involving polyethylene glycol, other particular embodiments entail modifications involving albumin, and still other particular modifications entail modifications involving glycosylation.

The terms "DNA", "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

The term "probe" refers to a fragment of DNA or RNA corresponding to a gene or sequence of interest, wherein the fragment has been labeled radioactively (e.g., by incorporating 32P or 35S) or with some other detectable molecule, such as biotin, digoxygenin or fluorescein. As stretches of DNA or RNA with complementary sequences will hybridize, a probe can be used, for example, to label viral plaques, bacterial colonies or bands on a gel that contain the gene of interest. A probe can be cloned DNA or it can be a synthetic DNA strand; the latter can be used to obtain a cDNA or genomic clone from an isolated protein by, for example, microsequencing a portion of the protein, deducing the nucleic acid sequence encoding the protein, synthesizing an oligonucleotide carrying that sequence, radiolabeling the sequence and using it as a probe to screen a cDNA library or a genomic library.

The term "heterologous" refers to two components that are defined by structures derived from different sources. For example, in the context of a polypeptide, a "heterologous" polypeptide may include operably linked amino acid sequences that are derived from different polypeptides (e.g., a first component comprising a recombinant polypeptide and a second component derived from a native GDF15 polypeptide). Similarly, in the context of a polynucleotide encoding a chimeric polypeptide, a "heterologous" polynucleotide may include operably linked nucleic acid sequences that can be derived from different genes (e.g., a first component from a nucleic acid encoding a polypeptide according to an embodiment disclosed herein and a second component from a nucleic acid encoding a carrier polypeptide). Other exemplary "heterologous" nucleic acids include expression constructs in which a nucleic acid comprising a coding sequence is operably linked to a regulatory element (e.g., a promoter) that is from a genetic origin different from that of the coding sequence (e.g., to provide for expression in a host cell of interest, which may be of different genetic origin than the promoter, the coding sequence or both). For example, a T7 promoter operably linked to a polynucleotide encoding a GDF15 polypeptide or domain thereof is said to be a heterologous nucleic acid. In the context of recombinant cells, "heterologous" can refer to the presence of a nucleic acid (or gene product, such as a polypeptide) that is of a different genetic origin than the host cell in which it is present.

The term "operably linked" refers to linkage between molecules to provide a desired function. For example, "operably linked" in the context of nucleic acids refers to a functional linkage between nucleic acid sequences. By way of example, a nucleic acid expression control sequence (such as a promoter, signal sequence, or array of transcription factor binding sites) may be operably linked to a second polynucleotide, wherein the expression control sequence affects transcription and/or translation of the second polynucleotide. In the context of a polypeptide, "operably linked" refers to a functional linkage between amino acid sequences (e.g., different domains) to provide for a described activity of the polypeptide.

As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal" or "immediately C-terminal" refers to a position of a first amino acid residue relative to a second amino acid residue where the first and second amino acid residues are covalently bound to provide a contiguous amino acid sequence.

"Derived from", in the context of an amino acid sequence or polynucleotide sequence (e.g., an amino acid sequence "derived from" a GDF15 polypeptide), is meant to indicate that the polypeptide or nucleic acid has a sequence that is based on that of a reference polypeptide or nucleic acid (e.g., a naturally occurring GDF15 polypeptide or a GDF15-encoding nucleic acid), and is not meant to be limiting as to the source or method in which the protein or nucleic acid is made. By way of example, the term "derived from" includes homologues or variants of reference amino acid or DNA sequences.

In the context of a polypeptide, the term "isolated" refers to a polypeptide of interest that, if naturally occurring, is in an environment different from that in which it may naturally occur. "Isolated" is meant to include polypeptides that are within samples that are substantially enriched for the polypeptide of interest and/or in which the polypeptide of interest is partially or substantially purified. Where the polypeptide is not naturally occurring, "isolated" indicates the polypeptide has been separated from an environment in which it was made by either synthetic or recombinant means.

"Enriched" means that a sample is non-naturally manipulated (e.g., by a scientist or a clinician) so that a polypeptide of interest is present in a) a greater concentration (e.g., at least 3-fold greater, at least 4-fold greater, at least 8-fold greater, at least 64-fold greater, or more) than the concentration of the polypeptide in the starting sample, such as a biological sample (e.g., a sample in which the polypeptide naturally occurs or in which it is present after administration), or b) a concentration greater than the environment in which the polypeptide was made (e.g., as in a bacterial cell).

"Substantially pure" indicates that a component (e.g., a polypeptide) makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition.

The terms "antibodies" (Abs) and "immunoglobulins" (Igs) refer to glycoproteins having the same structural characteristics. While antibodies exhibit binding specificity to a specific antigen, immunoglobulins include both antibodies and other antibody-like molecules which lack antigen specificity. Antibodies are described in detail hereafter.

The term "monoclonal antibody" refers to an antibody obtained from a population of substantially homogeneous antibodies, that is, the individual antibodies comprising the population are identical except for possible naturally occurring mutations that may be present in minor amounts. Monoclonal antibodies are highly specific, being directed against a single antigenic site. In contrast to polyclonal antibody preparations, which can include different antibodies directed against different determinants (epitopes), each monoclonal antibody is directed against a single determinant on the antigen.

In the context of an antibody, the term "isolated" refers to an antibody that has been separated and/or recovered from contaminant components of its natural environment; such contaminant components include materials which might interfere with diagnostic or therapeutic uses for the antibody, and may include enzymes, hormones, and other proteinaceous or nonproteinaceous solutes.

Growth Differentiation Factor 15 (GDF15)

GDF15, also known as MIC-1 (macrophage inhibitory cytokine-1), PDF, PLAB, NAG-1, TGF-PL, and PTGFB, is a member of the transforming growth factor $\beta$ (TGF-$\beta$) superfamily. GDF15, which is synthesized as a 62 kDa intracellular precursor protein that is subsequently cleaved by a furin-like protease, is secreted as a 25 kDa disulfide-linked protein. [See, e.g., Fairlie et al., J. Leukoc. Biol 65:2-5 (1999)].

GDF15 mRNA is seen in several tissues, including liver, kidney, pancreas, colon and placenta, and GDF15 expression in liver can be significantly up-regulated during injury of organs such as the liver, kidneys, heart and lungs.

The GDF15 precursor is a 308 amino acid polypeptide (NCBI Ref. Seq. NP_004855.2) containing a 29 amino acid signal peptide, a 167 amino acid pro-domain, and a mature domain of 112 amino acids which is excised from the pro-domain by furin-like proteases. A 308-amino acid GDF15 polypeptide is referred to as a "full-length" GDF15 polypeptide; a 112-amino acid GDF15 polypeptide (e.g., amino acids 197-308 of the amino acid sequence depicted in FIG. 1A) is a "mature" GDF15 polypeptide. Unless otherwise indicated, the term "GDF15" refers to the 112 amino acid mature sequence. In addition, numerical references to particular GDF15 residues refer to the 112 amino acid mature sequence (i.e., residue 1 is Ala (A), and residue 112 is Ile (I); see FIG. 1B). Of note, while the GDF15 precursor amino acid sequence predicts three excision sites, resulting in three putative forms of "mature" human GDF15 (i.e., 110, 112 and 115 amino acids), the 112 amino acid mature sequence is accepted as being correct.

The scope of the present disclosure includes GDF15 orthologs, and modified forms thereof, from other mammalian species, and their use, including mouse (NP_035949), chimpanzee (XP_524157), orangutan (XP_002828972), Rhesus monkey (EHH29815), giant panda (XP_002912774), gibbon (XP_003275874), guinea pig (XP_003465238), ferret (AER98997), cow (NP_001193227), pig (NP_001167527), dog (XP_541938) and platypus (*Ornithorhynchus anatinus*; AFV61279. The mature form of human GDF15 has approximately 67% amino acid identity to the mouse ortholog.

A. Identification of Modified GDF15 Muteins Having Desired Physical Properties

The present disclosure contemplates, in part, modified GDF15 muteins, wherein one or more amino acid residues of the mature GDF15 polypeptide are substituted with one or more other residues. For example, the GDF15 mutein component of a modified GDF15 mutein may include one or more substitutions of native lysine residues (i.e., residues 62, 69, 91 and 107) with any other amino acid, with the exception that GDF15 muteins containing K62Q are inactive. GDF15 muteins retaining K62 but incorporating any combination of K69Q, K91R and/or K107R are active in lowering body weight to a level comparable to that of mature human GDF15 control. In other GDF15 muteins, one or more GDF15 residue is substituted with another amino acid, including, for example, the following substitutions: H18Q, T19S or V20L. Such GDF15 muteins are candidates for modification to improve one or more inherent physical properties (e.g., stability, serum half-life, and generation of particular antibodies for use in detection assays and protein purification).

Examples of other candidate GDF15 muteins include, but are not limited to, the following:
  mutein v1) K69Q, K91R, K107R (SEQ ID NO:55);
  mutein v2) K62Q, K91R, K107R (SEQ ID NO:56);
  mutein v3) K62Q, K69Q, K107R (SEQ ID NO:57);
  mutein v4) K62Q, K69Q, K91R (SEQ ID NO:58);
  mutein v5) K91R, K107R (SEQ ID NO:59);
  mutein v6) K69Q, K107R (SEQ ID NO:60);
  mutein v7) K69Q, K91R (SEQ ID NO:61);
  mutein v8) H18Q, T19S, V20L, K62Q, K69Q, K91R, K107R (SEQ ID NO:62);
  mutein v9) H18Q, T19S, V20L, K62Q, K91R, K107R (SEQ ID NO:63);
  mutein v10) H18Q, T19S, V20L, K62Q, K69Q, K107R (SEQ ID NO:64); and
  mutein v11) H18Q, T19S, V20L, K62Q, K69Q, K91R (SEQ ID NO:65).

As indicated above and as described in more detail below, native GDF15 and GDF15 muteins may be modified through, for example, pegylation (covalent attachment of one or more molecules of polyethylene glycol (PEG), or derivatives thereof); glycosylation (e.g., N-glycosylation); polysialylation; albumin fusion molecules comprising serum albumin (e.g., human serum albumin (HSA), cyno serum albumin, or bovine serum albumin (BSA)); albumin binding through, for example, a conjugated fatty acid chain (acylation); Fc-fusion; and fusion with a PEG mimetic. In certain embodiments, the modifications are introduced in a site-specific manner. In other embodiments, the modifications include a linker.

In particular embodiments, the present disclosure contemplates modification of mature human GDF15 and GDF15 muteins by conjugation with albumin. In other embodiments, the present disclosure contemplates modification of mature human GDF15 and GDF15 muteins via N-glycosylation. The characteristics of albumins and GDF15/GDF15 mutein conjugates thereof (e.g., fusion proteins), and N-glycosylated GDF15/GDF15 muteins are described further hereafter.

Example 1 indicates the effects on body weight, food intake, and fasted blood glucose of a fusion molecule comprising mature HSA fused to the N-terminus of mature human GDF15 through a non-cleavable 3x(4Gly-Ser linker) linker. Administration of the fusion molecule (which exhibited improved half-life, expression, secretion and solubility relative to unconjugated recombinant human GDF15) resulted in significant improvement in body weight (FIG. 2A), food intake (FIG. 2B), and non-fasted blood glucose (FIG. 2C) compared to vehicle control. These data demonstrate that an HSA fusion with GDF15 is active, and that such fusion molecules represent a viable approach for enhancing certain beneficial properties of GDF15 muteins. The data also indicate that measurement of the indicated parameters may be useful as a platform for high-throughput screening of muteins.

Example 2 describes the methodology used to identify means for improving the physical properties (e.g., solubility and stability) of mature human GDF15. A set of six hydrophobic residues predicted to be surface-accessible were mutated to alanine as a means of increasing surface hydrophobicity. Fusion molecules were generated wherein each of the six GDF15 mutein sequences was fused to HSA through the linker depicted in FIG. 1H (a non-cleavable 3x(4Gly-Ser linker) linker); the sequences set forth in FIG. 3 neither depict the HSA component nor the linker component of the fusion molecules.

Thereafter, the fusion molecules were monitored for expression as secreted disulfide-linked homodimers (see FIG. 4). Data generated as described in the examples were used to evaluate solubility resulting from introduction of N-linked Glycosylation consensus site(s) along the sequence of mature human GDF15, and to address solubility limitations associated with surface hydrophobicities and hydrophilicities inherent to mature human GDF15. The evaluation entailed construction of GDF15/GDF15 muteins—N-terminal HSA fusion molecules containing a Factor Xa proteolytic-sensitive, cleavable linker. Reduction of surface hydrophobicity of five GDF15 muteins (w29, w32, w52, w68 and w89; see FIG. 3) was assessed via selective mutagenesis of hydrophobic residues to alanine Comparison of the solubility of these five muteins relative to mature human GDF15 indicated that w52 and w89 were the only muteins exhibiting improved solubility.

In addition, the surface hydrophilicity of the following five GDF15 mutein sequences (see FIG. 5) was assessed via selective mutagenesis of acidic residues to alanine: w113, w114, w115, w116 and w117. Comparison of the relative solubility of these five muteins to mature human GDF15 indicated that w116 was the only mutein that exhibited improved solubility.

The mature human GDF15 sequence was then assessed for its ability to accommodate introduction of N-linked Glycosylation consensus site(s). In this context, a single amino acid substitution would impart the required consensus site within the mature human GDF15 sequence, the consensus site for N-linked glycosylation being defined as "Asn-Xxx-Ser/Thr", where "Xxx" cannot be a proline residue. Based on a scan of the mature human GDF15 sequence, 14 possible single-point muteins were identified that would accommodate introduction of the N-Glycan consensus site. FIG. 6 depicts the sequences of the 14 mono-glycosylation muteins, as well as additional combinatorial di-Glycosylation muteins. Each of these engineered N-Glycan muteins was evaluated for both N-glycan site occupancy and for secretion as a folded GDF15 homodimer into mammalian tissue culture media. As set forth in FIG. 7, 10 of the 14 mono-glycosylated muteins were secreted as folded GDF15 homodimers, whereas 4 (w123, w125, w127 and w129) did not result in dimer formation. Of the 10 mono-glycosylation muteins that secreted as homodimers, two (w121 and w124) exhibited low occupancy and their solubility was not subsequently evaluated (see FIG. 7).

Engineered human mono-glycosylated GDF15 muteins which were both secreted as homodimers and possessed high glycan occupancy within the consensus site exhibited improved solubility compared to mature human GDF15 (see Example 3; FIG. 8). These GDF15 muteins were assessed for their ability to effect a reduction in food intake, and the data are set forth in FIG. 9.

Finally, hydrodynamic radii of engineered GDF15 N-Glycan muteins relative to mature human GDF15 were assessed utilizing analytical gel filtration chromatography (see Example 4). As indicated in FIG. 10, each of the N-linked glycan muteins increased the hydrodynamic radii of the human GDF15 disulfide-linked dimer. Thus, each mutein may potentially serve as a starting point for generating molecules having, for example, a favorable in vivo half-life.

Relative to mature human GDF15, many of the N-Glycosylation muteins exhibiting the most substantial improvements in physical properties (e.g., enhancement of solubility and increase in hydrodynamic radii) while maintaining an efficacious food intake reduction, appear to be localized to a specific epitope/region of human GDF15. Specifically, mutagenesis resulting in the introduction of N-Glycoyslation consensus sites appeared to be tolerated (based on correctly folded, biologically active human GDF15 homodimers) in the epitope/region spanning Gln90 to Leu98. Thus, though an understanding of preferred regions for mutagenesis is not required in order to practice the present disclosure, this epitope/region is believed to be advantageous for introduction of N-Glycosylation consensus sites.

Nucleic acid molecules encoding the Polypeptides are contemplated by the present disclosure, including their naturally-occurring and non-naturally occurring isoforms, allelic variants and splice variants. As previously noted, a Polypeptide also refers to polypeptides that have one or more alterations in the amino acid residues (e.g., at locations that are not conserved across variants or species) while retaining the conserved domains and having the same biological activity as the naturally-occurring Polypeptides. The present disclosure also encompasses nucleic acid sequences that vary in one or more bases from a naturally-occurring DNA sequence but still translate into an amino acid sequence that corresponds to a Polypeptide due to degeneracy of the genetic code. For example, GDF15 may refer to amino acid sequences that differ from the naturally-occurring sequence by one or more conservative substitutions, tags, or conjugates (e.g., a Polypeptide).

Thus, in addition to any naturally-occurring GDF15 polypeptide, the present disclosure contemplates having 1, 2, 3, 4, 5, 6, 7, 8, 9, or 10 usually no more than 20, 10, or 5 amino acid substitutions, where the substitution is usually a conservative amino acid substitution (e.g., a Polypeptide).

By "conservative amino acid substitution" generally refers to substitution of amino acid residues within the following groups: 1) L, I, M, V, F; 2) R, K; 3) F, Y, H, W, R; 4) G, A, T, S; 5) Q, N; and 6) D, E. Conservative amino acid substitutions preserve the activity of the protein by replacing an amino acid(s) in the protein with an amino acid with a side chain of similar acidity, basicity, charge, polarity, or size of the side chain. Guidance for substitutions, insertions, or deletions may be based on alignments of amino acid sequences of different variant proteins or proteins from different species.

The present disclosure also contemplates active fragments (e.g., subsequences) of the Polypeptides containing contiguous amino acid residues derived from the mature GDF15 polypeptide or a GDF15 mutein. The length of contiguous amino acid residues of a peptide or a polypeptide subsequence varies depending on the specific naturally-occurring amino acid sequence from which the subsequence is derived. In general, peptides and polypeptides may be from about 5 amino acids to about 10 amino acids, from about 10 amino acids to about 15 amino acids, from about 15 amino acids to about 20 amino acids, from about 20 amino acids to about 25 amino acids, from about 25 amino acids to about 30 amino acids, from about 30 amino acids to about 40 amino acids, from about 40 amino acids to about 50 amino acids, from about 50 amino acids to about 75 amino acids, from about 75 amino acids to about 100 amino acids, or from about 100 amino acids up to the full-length peptide or polypeptide.

Additionally, the Polypeptides can have a defined sequence identity compared to a reference sequence over a defined length of contiguous amino acids (e.g., a "comparison window"). Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Madison, Wis.), or by manual alignment and visual inspection (see, e.g., Current Protocols in Molecular Biology (Ausubel et al., eds. 1995 supplement)).

As an example, a suitable Polypeptide can comprise an amino acid sequence having at least about 75%, at least about 80%, at least about 85%, at least about 90%, at least about 95%, at least about 98%, or at least about 99%, amino acid sequence identity to a contiguous stretch of from about 5 amino acids to about 10 amino acids, from about 10 amino acids to about 12 amino acids, from about 12 amino acids to about 15 amino acids, from about 15 amino acids to about 20 amino acids, from about 20 amino acids to about 25 amino acids, from about 25 amino acids to about 30 amino acids, from about 30 amino acids to about 35 amino acids, from about 35 amino acids to about 40 amino acids, from about 40 amino acids to about 45 amino acids, from about 45 amino acids to about 50 amino acids, from about 50 amino acids to about 60 amino acids, from about 60 amino acids to about 70 amino acids, from about 70 amino acids to about 80 amino acids, from about 80 amino acids to about 90 amino acids, from about 90 amino acids to about 100 amino acids, or from about 100 amino acids to 112 amino acids or 113 amino acids, of one of the amino acid sequence depicted in FIGS. 1, 3, 5, and 6.

The Polypeptides may be isolated from a natural source (e.g., an environment other than its naturally-occurring environment) and also may be recombinantly made (e.g., in a genetically modified host cell such as bacteria; yeast; *Pichia*; insect cells; and the like), where the genetically modified host cell is modified with a nucleic acid comprising a nucleotide sequence encoding the polypeptide. The Polypeptides may also be synthetically produced (e.g., by cell-free chemical synthesis). Methods of productions are described in more detail below.

A Polypeptide may be generated using recombinant techniques to manipulate different GDF15-related nucleic acids known in the art to provide constructs capable of encoding the Polypeptide. It will be appreciated that, when provided a particular amino acid sequence, the ordinary skilled artisan will recognize a variety of different nucleic acid molecules encoding such amino acid sequence in view of her background and experience in, for example, molecular biology.

B. Modulators

The term "Modulators" refers to both Polypeptides and Activators. As indicated above, Activators are agents that, for example, stimulate, increase, activate, facilitate, enhance activation, sensitize or up-regulate the function or activity of one or more Polypeptides. In addition, Activators include agents that operate through the same mechanism of action as the Polypeptides (i.e., agents that modulate the same signaling pathway as the Polypeptides in a manner analogous to that of the Polypeptides) and are capable of eliciting a biological response comparable to (or greater than) that of the Polypeptides. An Activator may be, for example, a small molecule agonist compound, or other bioorganic molecule.

In some embodiments, the Activator is a small molecule agonist compound. Numerous libraries of small molecule compounds (e.g., combinatorial libraries) are commercially available and can serve as a starting point for identifying such an Activator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an Activator.

In still further embodiments, the Activator is an agonistic polypeptide structurally distinguishable from the Polypeptides but having comparable activity. The skilled artisan is able to identify such polypeptides having desired properties.

Amide Bond Substitutions

In some cases, a Polypeptide includes one or more linkages other than peptide bonds, e.g., at least two adjacent amino acids are joined via a linkage other than an amide bond. For example, in order to reduce or eliminate undesired proteolysis or other means of degradation, and/or to increase serum stability, and/or to restrict or increase conformational flexibility, one or more amide bonds within the backbone of a Polypeptide can be substituted.

In another example, one or more amide linkages (—CO—NH—) in a Polypeptide can be replaced with a linkage which is an isostere of an amide linkage, such as —$CH_2NH$—, $CH_2S$—, —$CH_2CH_2$—, —CH=CH-(cis and trans), —$COCH_2$—, —CH(OH)$CH_2$— or —$CH_2SO$—. One or more amide linkages in a Polypeptide can also be replaced by, for example, a reduced isostere pseudopeptide bond. See Couder et al. (1993) Int. J. Peptide Protein Res. 41:181-184. Such replacements and how to effect are known to those of ordinary skill in the art.

Amino Acid Substitutions

One or more amino acid substitutions can be made in a Polypeptide. The following are non-limiting examples:

a) substitution of alkyl-substituted hydrophobic amino acids, including alanine, leucine, isoleucine, valine, norleucine, (S)-2-aminobutyric acid, (S)-cyclohexylalanine or other simple alpha-amino acids substituted by an aliphatic side chain from C1-C10 carbons including branched, cyclic and straight chain alkyl, alkenyl or alkynyl substitutions;

b) substitution of aromatic-substituted hydrophobic amino acids, including phenylalanine, tryptophan, tyrosine, sulfotyrosine, biphenylalanine, 1-naphthylalanine, 2-naphthylalanine, 2-benzothienylalanine, 3-benzothienylalanine, histidine, including amino, alkylamino, dialkylamino, aza, halogenated (fluoro, chloro, bromo, or iodo) or alkoxy (from $C_1$-$C_4$)-substituted forms of the above-listed aromatic amino acids, illustrative examples of which are: 2-, 3- or 4-aminophenylalanine, 2-, 3- or 4-chlorophenylalanine, 2-, 3- or 4-methylphenylalanine, 2-, 3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2, 3, or 4-biphenylalanine, 2'-, 3'-, or 4'-methyl-, 2-, 3- or 4-biphenylalanine, and 2- or 3-pyridylalanine;

c) substitution of amino acids containing basic side chains, including arginine, lysine, histidine, ornithine, 2,3-diaminopropionic acid, homoarginine, including alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha-methyl-arginine, alpha-methyl-2,3-diaminopropionic acid, alpha-methyl-histidine, alpha-methyl-ornithine where the alkyl group occupies the pro-R position of the alpha-carbon. Also included are the amides formed from alkyl, aromatic, heteroaromatic (where the heteroaromatic group has one or more nitrogens, oxygens or sulfur atoms singly or in combination) carboxylic acids or any of the many well-known activated derivatives such as acid chlorides, active esters, active azolides and related derivatives) and lysine, ornithine, or 2,3-diaminopropionic acid;

d) substitution of acidic amino acids, including aspartic acid, glutamic acid, homoglutamic acid, tyrosine, alkyl, aryl, arylalkyl, and heteroaryl sulfonamides of 2,4-diaminopriopionic acid, ornithine or lysine and tetrazole-substituted alkyl amino acids;

e) substitution of side chain amide residue, including asparagine, glutamine, and alkyl or aromatic substituted derivatives of asparagine or glutamine; and f) substitution of hydroxyl containing amino acids, including serine, threonine, homoserine, 2,3-diaminopropionic acid, and alkyl or aromatic substituted derivatives of serine or threonine.

In some cases, a Polypeptide comprises one or more naturally occurring non-genetically encoded L-amino acids, synthetic L-amino acids or D-enantiomers of an amino acid. For example, a Polypeptide can comprise only D-amino acids. For example, a Polypeptide can comprise one or more of the following residues: hydroxyproline, β-alanine, o-aminobenzoic acid, m-aminobenzoic acid, p-aminobenzoic acid, m-aminomethylbenzoic acid, 2,3-diaminopropionic acid, α-aminoisobutyric acid, N-methylglycine (sarcosine), ornithine, citrulline, t-butylalanine, t-butylglycine, N-methylisoleucine, phenylglycine, cyclohexylalanine, norleucine, naphthylalanine, pyridylalanine 3-benzothienyl alanine, 4-chlorophenylalanine, 2-fluorophenylalanine, 3-fluorophenylalanine, 4-fluorophenylalanine, penicillamine, 1,2,3,4-tetrahydroisoquinoline-3-carboxylic acid, β-2-thienylalanine, methionine sulfoxide, homoarginine, N-acetyl lysine, 2,4-diamino butyric acid, rho-aminophenylalanine, N-methylvaline, homocysteine, homoserine, ε-amino hexanoic acid, ω-aminohexanoic acid, ω-aminoheptanoic acid, ω-aminooctanoic acid, ω-aminodecanoic acid, ω-aminotetradecanoic acid, cyclohexylalanine, α,γ-diaminobutyric acid, α,β-diaminopropionic acid, δ-amino valeric acid, and 2,3-diaminobutyric acid.

Additional Modifications

A cysteine residue or a cysteine analog can be introduced into a Polypeptide to provide for linkage to another peptide via a disulfide linkage or to provide for cyclization of the Polypeptide. Methods of introducing a cysteine or cysteine analog are known in the art; see, e.g., U.S. Pat. No. 8,067,532.

A Polypeptide can be cyclized. One or more cysteine or cysteine analogs can be introduced into a Polypeptide, where the introduced cysteine or cysteine analog can form a disulfide bond with a second introduced cysteine or cysteine analog. Other means of cyclization include introduction of an oxime linker or a lanthionine linker; see, e.g., U.S. Pat. No. 8,044,175. Any combination of amino acids (or non-amino acid moiety) that can form a cyclizing bond can be used and/or introduced. A cyclizing bond can be generated with any combination of amino acids (or with amino acid and —(CH2)n-CO— or —(CH2)n-C6H4-CO—) with functional groups which allow for the introduction of a bridge. Some examples are disulfides, disulfide mimetics such as the —(CH2)n- carba bridge, thioacetal, thioether bridges (cystathionine or lanthionine) and bridges containing esters and ethers. In these examples, n can be any integer, but is frequently less than ten.

Other modifications include, for example, an N-alkyl (or aryl) substitution (ψ[CONR]), or backbone crosslinking to construct lactams and other cyclic structures. Other derivatives of the modulator compounds of the present disclosure include C-terminal hydroxymethyl derivatives, O-modified derivatives (e.g., C-terminal hydroxymethyl benzyl ether), N-terminally modified derivatives including substituted amides such as alkylamides and hydrazides.

In some cases, one or more L-amino acids in a Polypeptide is replaced with a D-amino acid.

In some cases, a Polypeptide is a retroinverso analog. Sela and Zisman (1997) FASEB J. 11:449. Retro-inverso peptide analogs are isomers of linear polypeptides in which the direction of the amino acid sequence is reversed (retro) and the chirality, D- or L-, of one or more amino acids therein is inverted (inverso) e.g., using D-amino acids rather than L-amino acids. See, e.g., Jameson et al. (1994) Nature 368:744; and Brady et al. (1994) Nature 368:692.

A Polypeptide can include a "Protein Transduction Domain" (PTD), which refers to a polypeptide, polynucleotide, carbohydrate, or organic or inorganic compound that facilitates traversing a lipid bilayer, micelle, cell membrane, organelle membrane, or vesicle membrane. A PTD attached to another molecule facilitates the molecule traversing a membrane, for example going from extracellular space to intracellular space, or cytosol to within an organelle. In some embodiments, a PTD is covalently linked to the amino terminus of a Polypeptide, while in other embodiments, a PTD is covalently linked to the carboxyl terminus of a Polypeptide. Exemplary protein transduction domains include, but are not limited to, a minimal undecapeptide protein transduction domain (corresponding to residues 47-57 of HIV-1 TAT comprising YGRKKRRQRRR; SEQ ID NO:66); a polyarginine sequence comprising a number of arginines sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); an *Drosophila* Antennapedia protein transduction domain (Noguchi et al. (2003) Diabetes 52(7):1732-1737); a truncated human calcitonin peptide (Trehin et al. (2004) Pharm. Research 21:1248-1256); polylysine (Wender et al. (2000) Proc. Natl. Acad. Sci. USA 97:13003-13008); RRQRRTSKLMKR (SEQ ID NO:67); Transportan GWTLNSAGYLLGKINLKALAALAKKIL (SEQ ID NO:68); KALAWEAKLAKALAKALA-KHLAKALAKALKCEA (SEQ ID NO:69); and RQIKIW-FQNRRMKWKK (SEQ ID NO:70). Exemplary PTDs include, but are not limited to, YGRKKRRQRRR (SEQ ID NO:66), RKKRRQRRR (SEQ ID NO:71); an arginine homopolymer of from 3 arginine residues to 50 arginine residues; Exemplary PTD domain amino acid sequences include, but are not limited to, any of the following: YGRKKRRQRRR (SEQ ID NO:66); RKKRRQRR (SEQ ID NO:72); YARAAARQARA (SEQ ID NO:73); THRL-PRRRRRR (SEQ ID NO:74); and GGRRARRRRRR (SEQ ID NO:75).

The carboxyl group $COR_3$ of the amino acid at the C-terminal end of a Polypeptide can be present in a free form ($R_3$=OH) or in the form of a physiologically-tolerated alkaline or alkaline earth salt such as, e.g., a sodium, potassium or calcium salt. The carboxyl group can also be esterified with primary, secondary or tertiary alcohols such as, e.g., methanol, branched or unbranched $C_1$-$C_6$-alkyl alcohols, e.g., ethyl alcohol or tert-butanol. The carboxyl group can also be amidated with primary or secondary amines such as ammonia, branched or unbranched C1-C6-alkylamines or C1-C6 di-alkylamines, e.g., methylamine or dimethylamine.

The amino group of the amino acid $NR_1R_2$ at the N-terminus of a Polypeptide can be present in a free form ($R_1$=H and $R_2$=H) or in the form of a physiologically-tolerated salt such as, e.g., a chloride or acetate. The amino group can also be acetylated with acids such that $R_1$=H and $R_2$=acetyl, trifluoroacetyl, or adamantyl. The amino group can be present in a form protected by amino-protecting groups conventionally used in peptide chemistry such as, e.g., Fmoc, Benzyloxycarbonyl (Z), Boc, or Alloc. The amino group can be N-alkylated in which $R_1$ and/or $R_2$=$C_1$-$C_6$ alkyl or $C_2$-$C_8$ alkenyl or $C_7$-$C_9$ aralkyl. Alkyl residues can be straight-chained, branched or cyclic (e.g., ethyl, isopropyl and cyclohexyl, respectively).

Particular Modifications to Enhance and/or Mimic GDF15 Function

A Polypeptide can include one or more modifications that enhance a property desirable in a protein formulated for therapy (e.g., serum half-life), that enable the raising of antibodies for use in detection assays (e.g., epitope tags), that provide for ease of protein purification, etc. Such modifications include, but are not limited to, including pegylation (covalent attachment of one or more molecules of polyethylene glycol (PEG), or derivatives thereof); glycosylation (N- and O-linked); polysialylation; albumin fusion; albumin binding through a conjugated fatty acid chain (acylation); Fc-fusion proteins; and fusion with a PEG mimetic.

As set forth herein, the present disclosure contemplates fusion molecules comprising mature GDF15 polypeptide (e.g., mature human GDF15) or a GDF15 mutein polypeptide (e.g., a mutein of mature human GDF15), wherein the mature GDF15 polypeptide or GDF15 mutein polypeptide comprises at least one modification that does not alter its amino acid sequence, and wherein the modification improves at least one physical property of the polypeptide or the mutein polypeptide. In one embodiment, the GDF15 polypeptide or GDF15 mutein polypeptide modification comprises conjugation with serum albumin (e.g., human serum albumin (HSA), cyno serum albumin, or bovine serum albumin (BSA)). In some embodiments, the physical property is solubility.

In embodiments wherein the fusion molecule comprises a modified GDF15 polypeptide or a GDF15 mutein polypeptide, either of which is conjugated to albumin, the solubility of the fusion molecule is improved relative to unconjugated recombinant human GDF15. In certain embodiments, the fusion molecule has a solubility of at least 1 mg/mL in phosphate buffered saline (PBS) at pH 7.0. In other embodiments, the fusion molecule has a solubility of at least 2 mg/mL, at least 3 mg/mL, at least 4 mg/mL or at least 5 mg/mL. In other embodiments, the fusion molecule has a solubility of at least 6 mg/mL in phosphate buffered saline (PBS) at pH 7.0, at least 7 mg/mL, at least 8 mg/mL, at least 9 mg/mL, or at least 10 mg/mL. In particular embodiments, the fusion molecule has a solubility of greater than 10 mg/mL.

Pegylation: The clinical effectiveness of protein therapeutics is often limited by short plasma half-life and susceptibility to protease degradation. Studies of various therapeutic proteins (e.g., filgrastim) have shown that such difficulties may be overcome by various modifications, including conjugating or linking the polypeptide sequence to any of a variety of nonproteinaceous polymers, e.g., polyethylene glycol (PEG), polypropylene glycol, or polyoxyalkylenes (see, for example, typically via a linking moiety covalently bound to both the protein and the nonproteinaceous polymer, e.g., a PEG). Such PEG-conjugated biomolecules have been shown to possess clinically useful properties, including better physical and thermal stability, protection against susceptibility to enzymatic degradation, increased solubility, longer in vivo circulating half-life and decreased clearance, reduced immunogenicity and antigenicity, and reduced toxicity.

PEGs suitable for conjugation to a polypeptide sequence are generally soluble in water at room temperature, and have the general formula $R(O-CH_2-CH_2)_nO-R$, where R is hydrogen or a protective group such as an alkyl or an alkanol group, and where n is an integer from 1 to 1000. When R is a protective group, it generally has from 1 to 8 carbons. The PEG conjugated to the polypeptide sequence can be linear or branched. Branched PEG derivatives, "star-PEGs" and multi-armed PEGs are contemplated by the present disclosure. A molecular weight of the PEG used in the present disclosure is not restricted to any particular range, but certain embodiments have a molecular weight between 500 and 20,000 while other embodiments have a molecular weight between 4,000 and 10,000.

The present disclosure also contemplates compositions of conjugates wherein the PEGs have different n values and thus the various different PEGs are present in specific ratios. For example, some compositions comprise a mixture of conjugates where n=1, 2, 3 and 4. In some compositions, the percentage of conjugates where n=1 is 18-25%, the percentage of conjugates where n=2 is 50-66%, the percentage of conjugates where n=3 is 12-16%, and the percentage of conjugates where n=4 is up to 5%. Such compositions can be produced by reaction conditions and purification methods know in the art. For example, cation exchange chromatography may be used to separate conjugates, and a fraction is then identified which contains the conjugate having, for example, the desired number of PEGs attached, purified free from unmodified protein sequences and from conjugates having other numbers of PEGs attached.

PEG may be bound to a polypeptide of the present disclosure via a terminal reactive group (a "spacer"). The spacer is, for example, a terminal reactive group which mediates a bond between the free amino or carboxyl groups of one or more of the polypeptide sequences and polyethylene glycol. The PEG having the spacer which may be bound to the free amino group includes N-hydroxysuccinylimide polyethylene glycol which may be prepared by activating succinic acid ester of polyethylene glycol with N-hydroxysuccinylimide. Another activated polyethylene glycol which may be bound to a free amino group is 2,4-bis(O-methoxypolyethyleneglycol)-6-chloro-s-triazine which may be prepared by reacting polyethylene glycol monomethyl ether with cyanuric chloride. The activated polyethylene glycol which is bound to the free carboxyl group includes polyoxyethylenediamine.

Conjugation of one or more of the polypeptide sequences of the present disclosure to PEG having a spacer may be carried out by various conventional methods. For example, the conjugation reaction can be carried out in solution at a pH of from 5 to 10, at temperature from 4° C. to room temperature, for 30 minutes to 20 hours, utilizing a molar ratio of reagent to protein of from 4:1 to 30:1. Reaction conditions may be selected to direct the reaction towards producing predominantly a desired degree of substitution. In general, low temperature, low pH (e.g., pH=5), and short reaction time tend to decrease the number of PEGs attached, whereas high temperature, neutral to high pH (e.g., pH≥7), and longer reaction time tend to increase the number of PEGs attached. Various means known in the art may be used to terminate the reaction. In some embodiments the reaction is terminated by acidifying the reaction mixture and freezing at, e.g., −20° C.

The present disclosure also contemplates the use of PEG Mimetics. Recombinant PEG mimetics have been developed that retain the attributes of PEG (e.g., enhanced serum half-life) while conferring several additional advantageous properties. By way of example, simple polypeptide chains (comprising, for example, Ala, Glu, Gly, Pro, Ser and Thr) capable of forming an extended conformation similar to PEG can be produced recombinantly already fused to the peptide or protein drug of interest (e.g., Amunix' XTEN technology; Mountain View, Calif.). This obviates the need for an additional conjugation step during the manufacturing process. Moreover, established molecular biology techniques enable control of the side chain composition of the polypeptide chains, allowing optimization of immunogenicity and manufacturing properties.

Glycosylation: For purposes of the present disclosure, "glycosylation" is meant to broadly refer to the enzymatic process that attaches glycans to proteins, lipids or other organic molecules. The use of the term "glycosylation" in conjunction with the present disclosure is generally intended to mean adding or deleting one or more carbohydrate moieties (either by removing the underlying glycosylation site or by deleting the glycosylation by chemical and/or enzymatic means), and/or adding one or more glycosylation sites that may or may not be present in the native sequence. In addition, the phrase includes qualitative changes in the glycosylation of the native proteins involving a change in the nature and proportions of the various carbohydrate moieties present.

Glycosylation can dramatically affect the physical properties of proteins and can also be important in protein stability, secretion, and subcellular localization. Indeed, glycosylation of the GDF15- and GDF15 mutein-related polypeptides described herein imparts beneficial improvements to their physical properties. By way of example, but not limitation, solubility of GDF15/GDF15 muteins can be improved by glycosylation, and such improvement may be substantial (see Examples). The solubility improvement exhibited by such modified GDF15/GDF15 muteins can, for example, enable the generation of formulations more suitable for pharmaceutical administration than non-glycosylated GDF15/GDF15 muteins. The glycosylated GDF15/GDF15 mutein polypeptides may also exhibit enhanced stability. Moreover, the polypeptides may improve one or more pharmacokinetic properties, such as half-life.

Proper glycosylation can be essential for biological activity. In fact, some genes from eucaryotic organisms, when expressed in bacteria (e.g., *E. coli*) which lack cellular processes for glycosylating proteins, yield proteins that are recovered with little or no activity by virtue of their lack of glycosylation.

Addition of glycosylation sites can be accomplished by altering the amino acid sequence. The alteration to the polypeptide may be made, for example, by the addition of, or substitution by, one or more serine or threonine residues (for O-linked glycosylation sites) or asparagine residues (for N-linked glycosylation sites). The structures of N-linked and O-linked oligosaccharides and the sugar residues found in each type may be different. One type of sugar that is commonly found on both is N-acetylneuraminic acid (hereafter referred to as sialic acid). Sialic acid is usually the terminal residue of both N-linked and O-linked oligosaccharides and, by virtue of its negative charge, may confer acidic properties to the glycoprotein. A particular embodiment of the present disclosure comprises the generation and use of N-glycosylation variants.

The polypeptide sequences of the present disclosure may optionally be altered through changes at the DNA level, particularly by mutating the DNA encoding the polypeptide at preselected bases such that codons are generated that will translate into the desired amino acids. Another means of increasing the number of carbohydrate moieties on the polypeptide is by chemical or enzymatic coupling of glycosides to the polypeptide. Removal of carbohydrates may be accomplished chemically or enzymatically, or by substitution of codons encoding amino acid residues that are glycosylated. Chemical deglycosylation techniques are known, and enzymatic cleavage of carbohydrate moieties on polypeptides can be achieved by the use of a variety of endo- and exo-glycosidases.

Dihydrofolate reductase (DHFR)-deficient Chinese Hamster Ovary (CHO) cells are a commonly used host cell for the production of recombinant glycoproteins. These cells do not express the enzyme beta-galactoside alpha-2,6-sialyltransferase and therefore do not add sialic acid in the alpha-2,6 linkage to N-linked oligosaccharides of glycoproteins produced in these cells.

Polysialylation: The present disclosure also contemplates the use of polysialylation, the conjugation of peptides and proteins to the naturally occurring, biodegradable α-(2→8) linked polysialic acid ("PSA") in order to improve their stability and in vivo pharmacokinetics. PSA is a biodegradable, non-toxic natural polymer that is highly hydrophilic, giving it a high apparent molecular weight in the blood which increases its serum half-life. In addition, polysialylation of a range of peptide and protein therapeutics has led to markedly reduced proteolysis, retention of activity in vivo activity, and reduction in immunogenicity and antigenicity (see, e.g., G. Gregoriadis et al., Int. J. Pharmaceutics 300(1-2):125-30). As with modifications with other conjugates (e.g., PEG), various techniques for site-specific polysialylation are available (see, e.g., T. Lindhout et al., PNAS 108(18)7397-7402 (2011)).

Albumin Fusion: Additional suitable components and molecules for conjugation include albumins such as human serum albumin (HSA), cyno serum albumin, and bovine serum albumin (BSA).

Mature HSA (see FIG. 1D), a 585 amino acid polypeptide (~67 kDa) having a serum half-life of ~20 days, is primarily responsible for the maintenance of colloidal osmotic blood pressure, blood pH, and transport and distribution of numerous endogenous and exogenous ligands. The protein has three structurally homologous domains (domains I, II and III), is almost entirely in the alpha-helical conformation, and is highly stabilized by 17 disulphide bridges. The three primary drug binding regions of albumin are located on each of the three domains within sub-domains IB, IIA and IIIA.

Albumin synthesis takes place in the liver, which produces the short-lived, primary product preproalbumin. Thus, the full-length HSA has a signal peptide of 18 amino acids (MK-WVTFISLLFLFSSAYS; SEQ ID NO:53) followed by a pro-domain of 6 amino acids (RGVFRR; SEQ ID NO:54); this 24 amino acid residue peptide may be referred to as the pre-pro domain. HSA can be expressed and secreted using its endogenous signal peptide as a pre-pro-domain (see FIG. 1C). Alternatively, HSA can be expressed and secreted using a IgK signal peptide (SEQ ID NO:53) fused to a mature construct (D25-L609 of SEQ ID NO:5); in a construct used to generate the experimental data presented herein, the endogenous signal peptide was replaced with human IgK signal peptide, and the endogenous pro-domain was left out entirely. In turn, preproalbumin is rapidly co-translationally cleaved in the endoplasmic reticulum lumen at its amino terminus to produce the stable, 609-amino acid precursor polypeptide, proalbumin (see FIG. 1C). Proalbumin then passes to the Golgi apparatus, where it is converted to the 585 amino acid mature albumin by a furin-dependent amino-terminal cleavage. Unless otherwise indicated, reference herein to "albumin" or to "mature albumin" is meant to refer to HSA.

The primary amino acid sequences, structure, and function of albumins are highly conserved across species, as are the processes of albumin synthesis and secretion. Albumin serum proteins comparable to HSA are found in, for example, cynomolgus monkeys, cows, dogs, rabbits and rats. Of the non-human species, bovine serum albumin (BSA) is the most structurally similar to HSA. [See, e.g., Kosa et al., J Pharm Sci. 96(11):3117-24 (November 2007)]. The present disclosure contemplates the use of albumin from non-human species, including, but not limited to, those set forth above, in, for example, the drug development process. In certain embodiments, the non-human species is a cow. In other embodiments, the non-human species is a cynomolgus monkey.

According to the present disclosure, albumin may be conjugated to a drug molecule (e.g., a polypeptide described herein) at the carboxyl terminus, the amino terminus, both the carboxyl and amino termini, and internally (see, e.g., U.S. Pat. Nos. 5,876,969 and 7,056,701). Furthermore, the present disclosure contemplates albumin fusion proteins comprising more than one homologous (e.g., multiple GDF15 mutein molecules) or heterologous (e.g., a GDF15 mutein molecule and a distinct anti-diabetic agent) drug molecules.

In the HSA—drug molecule conjugates contemplated by the present disclosure, various forms of albumin may be used, such as albumin secretion pre-sequences and variants thereof, fragments and variants thereof, and HSA variants. Such forms generally possess one or more desired albumin activities. In additional embodiments, the present disclosure involves fusion proteins comprising a polypeptide drug molecule fused directly or indirectly to albumin, an albumin fragment, and albumin variant, etc., wherein the fusion protein has a higher plasma stability than the unfused drug molecule and/or the fusion protein retains the therapeutic activity of the unfused drug molecule. In some embodiments, the indirect fusion is effected by a linker, such as a peptide linker or modified version thereof.

In particular embodiments, the albumin, albumin variant, or albumin fragment is conjugated to a polypeptide comprising the 167 amino acid pro-domain and the 112 amino acid mature domain of the 308 amino acid GDF15 precursor polypeptide; thus, the present disclosure contemplates a GDF15 polypeptide that has a length of from about amino acid residue 30 to about amino acid residue 308 of the sequence depicted in FIG. 1A (SEQ ID NO:1).

In still other embodiments, albumin serves as an intracellular chaperon for the expression of a drug molecule. For example, a nucleic acid molecule (e.g., a vector) encoding a has—GDF15/GDF15 mutein fusion protein may be introduced into a cell. Cellular introduction can be by any means (e.g., transfection or electroporation) known in the art. The expressed has—GDF15/GDF15 mutein fusion protein may optionally be conjugated through a linker(s). Examples of suitable linkers are described herein. Some embodiments contemplate a peptide linker of, for example, four-to-six amino acids.

In embodiments wherein the fusion protein comprises a linker, the linker may be a non-cleavable linker. For example, in one embodiment the present disclosure contemplates a fusion molecule wherein the HSA precursor amino acid sequence is fused to the N-terminus of the mature human GDF15 or a GDF15 mutein amino acid sequence through a non-cleavable 3x(4Gly-Ser linker) linker (see, e.g., FIG. 1G), and in another embodiment the present disclosure contemplates a fusion molecule wherein the mature HSA amino acid sequence is fused to the N-terminus of the mature human GDF15 or a GDF15 mutein amino acid sequence through a non-cleavable 3x(4Gly-Ser linker) linker (see, e.g., FIG. 1H).

In other embodiments wherein the fusion protein comprises a linker, the linker is a cleavable linker. For example, the disclosure contemplates a fusion molecule wherein the HSA precursor amino acid sequence is fused to the N-terminus of the mature human GDF15 or a GDF15 mutein amino acid sequence through a protease-sensitive 2x(4Gly-Ser) Factor Xa-cleavable linker (see, e.g., FIG. 1E). In other embodiments, the disclosure contemplates a fusion molecule wherein the mature HSA amino acid sequence is fused to the N-terminus of the mature human GDF15 or a GDF15 mutein amino acid sequence through a protease-sensitive 2x(4Gly-Ser) Factor Xa-cleavable linker (see, e.g., FIG. 1F).

Construction of mature recombinant GDF15/GDF15 mutein-cleavable linker-HSA fusion molecules may be used to facilitate the assessment of, for example, solubility and the determination of in vivo efficacy of the GDF15/GDF15 mutein. In such embodiments, the GDF15/GDF15 mutein may be excised from the HSA chaperone through intracellular cleavage or through in vitro enzymatic cleavage. In some embodiments, excision is effected by proteolytic digestion of the cleavable linker using any viable protease.

Intracellular cleavage may be carried out enzymatically by, for example, furin or caspase. The cells express a low level of these endogenous enzymes, which are capable of cleaving a portion of the fusion molecules intracellularly; thus, some of the polypeptides are secreted from the cell without being conjugated to HSA, while some of the polypeptides are secreted in the form of fusion molecules that comprise HSA. Embodiments of the present disclosure contemplate the use of various furin fusion constructs. For example, constructs may be designed that comprise the sequence RGRR (SEQ ID NO:80), RKRKKR (SEQ ID NO:81), RKKR (SEQ ID NO:82), or RRRKKR (SEQ ID NO:83). Such constructs can have the following general structure: Igk-HSA(D25-L609 of SEQ ID NO:5)-2X(G4S)-furin sequence-hGDF15(A197-I308, of SEQ ID NO:1).

The present disclosure also contemplates extra-cellular cleavage (i.e., ex-vivo cleavage) whereby the fusion molecules are secreted from the cell, subjected to purification, then cleaved (e.g., using, for example, a Factor Xa proteolytic-sensitive linker or an enterokinase). It is understood that the excision may dissociate the entire HSA-linker complex from the mature GDF15 or GDF15 mutein, or less that the entire HSA-linker complex.

As alluded to above, fusion of albumin to one or more polypeptides of the present disclosure can, for example, be achieved by genetic manipulation, such that the DNA coding for HSA, or a fragment thereof, is joined to the DNA coding for the one or more polypeptide sequences. Thereafter, a suitable host can be transformed or transfected with the fused nucleotide sequences in the form of, for example, a suitable plasmid, so as to express a fusion polypeptide. The expression may be effected in vitro from, for example, prokaryotic or eukaryotic cells, or in vivo from, for example, a transgenic organism. In some embodiments of the present disclosure, the expression of the fusion protein is performed in mammalian cell lines, for example, CHO cell lines. Transformation is used broadly herein to refer to the genetic alteration of a cell resulting from the direct uptake, incorporation and expression of exogenous genetic material (exogenous DNA) from its surroundings and taken up through the cell membrane(s). Transformation occurs naturally in some species of bacteria, but it can also be effected by artificial means in other cells.

Furthermore, albumin itself may be modified to extend its circulating half-life. Fusion of the modified albumin to one or more Polypeptides can be attained by the genetic manipulation techniques described above or by chemical conjugation; the resulting fusion molecule has a half-life that exceeds that of fusions with non-modified albumin. [See WO2011/051489].

Alternative Albumin Binding Strategies: Several albumin—binding strategies have been developed as alternatives for direct fusion, including albumin binding through a conjugated fatty acid chain (acylation). Because serum albumin is a transport protein for fatty acids, these natural ligands with albumin—binding activity have been used for half-life extension of small protein therapeutics. For example, insulin determir (LEVEMIR), an approved product for diabetes, comprises a myristyl chain conjugated to a genetically-modified insulin, resulting in a long-acting insulin analog.

The present disclosure also contemplates fusion proteins which comprise an albumin binding domain (ABD) polypeptide sequence and the sequence of one or more of the polypeptides described herein. Any ABD polypeptide sequence described herein or in the literature can be a component of the fusion proteins. The components of the fusion proteins can be optionally covalently bonded through a linker, such as those linkers described herein. In some of the embodiments of the present disclosure, the fusion proteins comprise the ABD polypeptide sequence as an N-terminal moiety and the polypeptides described herein as a C-terminal moiety.

The present disclosure also contemplates fusion proteins comprising a fragment of an albumin binding polypeptide, which fragment substantially retains albumin binding; or a multimer of albumin binding polypeptides or their fragments comprising at least two albumin binding polypeptides or their fragments as monomer units.

Without wishing to be bound by any theory, it is believed that the polypeptides described herein bind to the ABD polypeptide sequence, thereby sequestering the polypeptides in a subject leading to increased duration of action in the subject.

For a general discussion of ABD and related technologies, see WO 2012/050923, WO 2012/050930, WO 2012/004384 and WO 2009/016043.

Conjugation with Other Molecules: Additional suitable components and molecules for conjugation include, for example, thyroglobulin; tetanus toxoid; Diphtheria toxoid; polyamino acids such as poly(D-lysine:D-glutamic acid); VP6 polypeptides of rotaviruses; influenza virus hemaglutinin, influenza virus nucleoprotein; Keyhole Limpet Hemocyanin (KLH); and hepatitis B virus core protein and surface antigen; or any combination of the foregoing.

Thus, the present disclosure contemplates conjugation of one or more additional components or molecules at the N- and/or C-terminus of a polypeptide sequence, such as another protein (e.g., a protein having an amino acid sequence heterologous to the subject protein), or a carrier molecule. Thus, an exemplary polypeptide sequence can be provided as a conjugate with another component or molecule.

A conjugate modification may result in a polypeptide sequence that retains activity with an additional or complementary function or activity of the second molecule. For example, a polypeptide sequence may be conjugated to a molecule, e.g., to facilitate solubility, storage, in vivo or shelf half-life or stability, reduction in immunogenicity, delayed or controlled release in vivo, etc. Other functions or activities include a conjugate that reduces toxicity relative to an unconjugated polypeptide sequence, a conjugate that targets a type of cell or organ more efficiently than an unconjugated polypeptide sequence, or a drug to further counter the causes or effects associated with a disorder or disease as set forth herein (e.g., diabetes).

A Polypeptide may also be conjugated to large, slowly metabolized macromolecules such as proteins; polysaccharides, such as sepharose, agarose, cellulose, cellulose beads; polymeric amino acids such as polyglutamic acid, polylysine; amino acid copolymers; inactivated virus particles; inactivated bacterial toxins such as toxoid from diphtheria, tetanus, cholera, leukotoxin molecules; inactivated bacteria; and dendritic cells. Such conjugated forms, if desired, can be used to produce antibodies against a polypeptide of the present disclosure.

Additional candidate components and molecules for conjugation include those suitable for isolation or purification. Particular non-limiting examples include binding molecules, such as biotin (biotin-avidin specific binding pair), an antibody, a receptor, a ligand, a lectin, or molecules that comprise a solid support, including, for example, plastic or polystyrene beads, plates or beads, magnetic beads, test strips, and membranes.

Purification methods such as cation exchange chromatography may be used to separate conjugates by charge difference, which effectively separates conjugates into their various molecular weights. For example, the cation exchange column can be loaded and then washed with ~20 mM sodium acetate, pH ~4, and then eluted with a linear (0 M to 0.5 M) NaCl gradient buffered at a pH from about 3 to 5.5, e.g., at pH ~4.5. The content of the fractions obtained by cation exchange chromatography may be identified by molecular weight using conventional methods, for example, mass spectroscopy, SDS-PAGE, or other known methods for separating molecular entities by molecular weight.

Fc-fusion Molecules: In certain embodiments, the amino- or carboxyl-terminus of a polypeptide sequence of the present disclosure can be fused with an immunoglobulin Fc region (e.g., human Fc) to form a fusion conjugate (or fusion molecule). Fc fusion conjugates have been shown to increase the systemic half-life of biopharmaceuticals, and thus the biopharmaceutical product may require less frequent administration.

Fc binds to the neonatal Fc receptor (FcRn) in endothelial cells that line the blood vessels, and, upon binding, the Fc fusion molecule is protected from degradation and re-released into the circulation, keeping the molecule in circulation longer. This Fc binding is believed to be the mechanism by which endogenous IgG retains its long plasma half-life. More recent Fc-fusion technology links a single copy of a biopharmaceutical to the Fc region of an antibody to optimize the pharmacokinetic and pharmacodynamic properties of the biopharmaceutical as compared to traditional Fc-fusion conjugates.

Other Modifications: The present disclosure contemplates the use of other modifications, currently known or developed in the future, of the Polypeptides to improve one or more properties. One such method for prolonging the circulation half-life, increasing the stability, reducing the clearance, or altering the immunogenicity or allergenicity of a polypeptide of the present disclosure involves modification of the polypeptide sequences by hesylation, which utilizes hydroxyethyl starch derivatives linked to other molecules in order to modify the molecule's characteristics. Various aspects of hesylation are described in, for example, U.S. Patent Appln. Nos. 2007/0134197 and 2006/0258607.

The present disclosure also contemplates fusion molecules comprising SUMO as a fusion tag (LifeSensors, Inc.; Malvern, Pa.). Fusion of a polypeptide described herein to SUMO may convey several beneficial effects on the polypeptide, including enhancement of expression, improvement in solubility, and/or assistance in the development of purification methods. SUMO proteases recognize the tertiary structure of SUMO and cleave the fusion protein at the C-terminus of SUMO, thus releasing a polypeptide described herein with the desired N-terminal amino acid.

Linkers: Linkers and their use have been described above. Any of the foregoing components and molecules used to modify the polypeptide sequences of the present disclosure may optionally be conjugated via a linker. Suitable linkers include "flexible linkers" which are generally of sufficient length to permit some movement between the modified polypeptide sequences and the linked components and molecules. The linker molecules are generally about 6-50 atoms long. The linker molecules may also be, for example, aryl acetylene, ethylene glycol oligomers containing 2-10 monomer units, diamines, diacids, amino acids, or combinations thereof. Suitable linkers can be readily selected and can be of any suitable length, such as 1 (e.g., Gly), 2, 3, 4, 5, 6, 7, 8, 9, 10, 10-20, 20-30, 30-50 amino acids (e.g., Gly).

Exemplary flexible linkers include glycine polymers $(G)_n$, glycine-serine polymers (for example, $(GS)_n$, $GSGGS_n$ and $GGGS_n$, where n is an integer of at least one), glycine-alanine polymers, alanine-serine polymers, and other flexible linkers.

Glycine and glycine-serine polymers are relatively unstructured, and therefore may serve as a neutral tether between components. Exemplary flexible linkers include, but are not limited to GGSG (SEQ ID NO:84), GGSGG (SEQ ID NO:85), GSGSG (SEQ ID NO:86), GSGGG (SEQ ID NO:87), GGGSG (SEQ ID NO:88), and GSSSG (SEQ ID NO:89).

Methods of Production of Polypeptides

A polypeptide of the present disclosure can be produced by any suitable method, including recombinant and non-recombinant methods (e.g., chemical synthesis).

A. Chemical Synthesis

Where a polypeptide is chemically synthesized, the synthesis may proceed via liquid-phase or solid-phase. Solid-phase peptide synthesis (SPPS) allows the incorporation of unnatural amino acids and/or peptide/protein backbone modification. Various forms of SPPS, such as Fmoc and Boc, are available for synthesizing polypeptides of the present disclosure. Details of the chemical synthesis are known in the art (e.g., Ganesan A. 2006 Mini Rev. Med. Chem. 6:3-10; and Camarero J. A. et al., 2005 Protein Pept Lett. 12:723-8).

Solid phase peptide synthesis may be performed as described hereafter. The α functions (Nα) and any reactive side chains are protected with acid-labile or base-labile groups. The protective groups are stable under the conditions for linking amide bonds but can be readily cleaved without impairing the peptide chain that has formed. Suitable protective groups for the α-amino function include, but are not limited to, the following: t-butyloxycarbonyl (Boc), benzyloxycarbonyl (Z), o-chlorbenzyloxycarbonyl, bi-phenylisopropyloxycarbonyl, tert-amyloxycarbonyl (Amoc), α,α-dimethyl-3,5-dimethoxy-benzyloxycarbonyl, o-nitrosulfenyl, 2-cyano-t-butoxy-carbonyl, 9-fluorenylmethoxycarbonyl (Fmoc), 1-(4,4-dimethyl-2,6-dioxocylohex-1-ylidene)ethyl (Dde) and the like.

Suitable side chain protective groups include, but are not limited to: acetyl, allyl (All), allyloxycarbonyl (Alloc), benzyl (Bzl), benzyloxycarbonyl (Z), t-butyloxycarbonyl (Boc), benzyloxymethyl (Bom), o-bromobenzyloxycarbonyl, t-butyl (tBu), t-butyldimethylsilyl, 2-chlorobenzyl, 2-chlorobenzyloxycarbonyl (2-CIZ), 2,6-dichlorobenzyl, cyclohexyl, cyclopentyl, 1-(4,4-dimethyl-2,6-dioxocyclohex-1-ylidene) ethyl (Dde), isopropyl, 4-methoxy-2,3-6-trimethylbenzylsulfonyl (Mtr), 2,3,5,7,8-pentamethylchroman-6-sulfonyl (Pmc), pivalyl, tetrahydropyran-2-yl, tosyl (Tos), 2,4,6-trimethoxybenzyl, trimethylsilyl and trityl (Trt).

In the solid phase synthesis, the C-terminal amino acid is coupled to a suitable support material. Suitable support materials are those which are inert towards the reagents and reaction conditions for the step-wise condensation and cleavage reactions of the synthesis process and which do not dissolve in the reaction media being used. Examples of commercially-available support materials include styrene/divinylbenzene copolymers which have been modified with reactive groups and/or polyethylene glycol; chloromethylated styrene/divinylbenzene copolymers; hydroxymethylated or aminomethylated styrene/divinylbenzene copolymers and the like. Polystyrene (1%)-divinylbenzene or TentaGel® derivatized with 4-benzyloxybenzyl-alcohol (Wang-anchor) or 2-chlorotrityl chloride can be used if it is intended to prepare the peptidic acid. In the case of the peptide amide, polystyrene (1%) divinylbenzene or TentaGel® derivatized with 5-(4'-aminomethyl)-3',5'-dimethoxyphenoxy)valeric acid (PAL-anchor) or p-(2,4-dimethoxyphenyl-amino methyl)-phenoxy group (Rink amide anchor) can be used.

The linkage to the polymeric support can be achieved by reacting the C-terminal Fmoc-protected amino acid with the support material with the addition of an activation reagent in ethanol, acetonitrile, N,N-dimethylformamide (DMF), dichloromethane, tetrahydrofuran, N-methylpyrrolidone or similar solvents at room temperature or elevated temperatures (e.g., between 40° C. and 60° C.) and with reaction times of, e.g., 2 to 72 hours.

The coupling of the Nα-protected amino acid (e.g., the Fmoc amino acid) to the PAL, Wang or Rink anchor can, for example, be carried out with the aid of coupling reagents such as N,N'-dicyclohexylcarbodiimide (DCC), N,N'-diisopropylcarbodiimide (DIC) or other carbodiimides, 2-(1H-benzotriazol-1-yl)-1,1,3,3-tetramethyluronium tetrafluoroborate (TBTU) or other uronium salts, o-acyl-ureas, benzotriazol-1-yl-tris-pyrrolidino-phosphonium hexafluorophosphate (PyBOP) or other phosphonium salts, N-hydroxysuccinimides, other N-hydroxyimides or oximes in the presence or also in the absence of 1-hydroxybenzotriazole or 1-hydroxy-7-azabenzotriazole, e.g., with the aid of TBTU with addition of HOBt, with or without the addition of a base such as, for example, diisopropylethylamine (DIEA), triethylamine or N-methylmorpholine, e.g., diisopropylethylamine with reaction times of 2 to 72 hours (e.g., 3 hours in a 1.5 to 3-fold excess of the amino acid and the coupling reagents, e.g., in a 2-fold excess and at temperatures between about 10° C. and 50° C., e.g., 25° C. in a solvent such as dimethylformamide, N-methylpyrrolidone or dichloromethane, e.g., dimethylformamide).

Instead of the coupling reagents, it is also possible to use the active esters (e.g., pentafluorophenyl, p-nitrophenyl or the like), the symmetric anhydride of the Nα-Fmoc-amino acid, its acid chloride or acid fluoride under the conditions described above.

The Nα-protected amino acid (e.g., the Fmoc amino acid) can be coupled to the 2-chlorotrityl resin in dichloromethane with the addition of DIEA with reaction times of 10 to 120 minutes, e.g., 20 minutes, but is not limited to the use of this solvent and this base.

The successive coupling of the protected amino acids can be carried out according to conventional methods in peptide synthesis, typically in an automated peptide synthesizer. After cleavage of the Nα-Fmoc protective group of the coupled amino acid on the solid phase by treatment with, e.g., piperidine (10% to 50%) in dimethylformamide for 5 to 20 minutes, e.g., 2×2 minutes with 50% piperidine in DMF and 1×15 minutes with 20% piperidine in DMF, the next protected amino acid in a 3 to 10-fold excess, e.g., in a 10-fold excess, is coupled to the previous amino acid in an inert, non-aqueous, polar solvent such as dichloromethane, DMF or mixtures of the two and at temperatures between about 10° C. and 50° C., e.g., at 25° C. The previously mentioned reagents for coupling the first Nα-Fmoc amino acid to the PAL, Wang or Rink anchor are suitable as coupling reagents. Active esters of the protected amino acid, or chlorides or fluorides or symmetric anhydrides thereof can also be used as an alternative.

At the end of the solid phase synthesis, the peptide is cleaved from the support material while simultaneously cleaving the side chain protecting groups. Cleavage can be carried out with trifluoroacetic acid or other strongly acidic media with addition of 5%-20% V/V of scavengers such as dimethylsulfide, ethylmethylsulfide, thioanisole, thiocresol, m-cresol, anisole ethanedithiol, phenol or water, e.g., 15% v/v dimethylsulfide/ethanedithiol/m-cresol 1:1:1, within 0.5 to 3 hours, e.g., 2 hours. Peptides with fully protected side chains are obtained by cleaving the 2-chlorotrityl anchor with glacial acetic acid/trifluoroethanol/dichloromethane 2:2:6. The protected peptide can be purified by chromatography on silica gel. If the peptide is linked to the solid phase via the Wang anchor and if it is intended to obtain a peptide with a C-terminal alkylamidation, the cleavage can be carried out by aminolysis with an alkylamine or fluoroalkylamine. The aminolysis is carried out at temperatures between about −10° C. and 50° C. (e.g., about 25° C.), and reaction times between about 12 and 24 hours (e.g., about 18 hours). In addition the peptide can be cleaved from the support by re-esterification, e.g., with methanol.

The acidic solution that is obtained may be admixed with a 3 to 20-fold amount of cold ether or n-hexane, e.g., a 10-fold excess of diethyl ether, in order to precipitate the peptide and hence to separate the scavengers and cleaved protective groups that remain in the ether. A further purification can be carried out by re-precipitating the peptide several times from glacial acetic acid. The precipitate that is obtained can be taken up in water or tert-butanol or mixtures of the two solvents, e.g., a 1:1 mixture of tert-butanol/water, and freeze-dried.

The peptide obtained can be purified by various chromatographic methods, including ion exchange over a weakly basic resin in the acetate form; hydrophobic adsorption chromatography on non-derivatized polystyrene/divinylbenzene copolymers (e.g., Amberlite® XAD); adsorption chromatography on silica gel; ion exchange chromatography, e.g., on carboxymethyl cellulose; distribution chromatography, e.g., on Sephadex® G-25; countercurrent distribution chromatography; or high pressure liquid chromatography (HPLC) e.g., reversed-phase HPLC on octyl or octadecylsilylsilica (ODS) phases.

B. Recombinant Production

Where a polypeptide is produced using recombinant techniques, the polypeptide may be produced as an intracellular protein or as a secreted protein, using any suitable construct and any suitable host cell, which can be a prokaryotic or eukaryotic cell, such as a bacterial (e.g., *E. coli*) or a yeast host cell, respectively. Other examples of eukaryotic cells that may be used as host cells include insect cells, mammalian cells, and/or plant cells. Where mammalian host cells are used, they may include human cells (e.g., HeLa, 293, H9 and Jurkat cells); mouse cells (e.g., NIH3T3, L cells, and C127 cells); primate cells (e.g., Cos 1, Cos 7 and CV1) and hamster cells (e.g., Chinese hamster ovary (CHO) cells).

A variety of host-vector systems suitable for the expression of a polypeptide may be employed according to standard procedures known in the art. See, e.g., Sambrook et al., 1989 Current Protocols in Molecular Biology Cold Spring Harbor Press, New York; and Ausubel et al. 1995 Current Protocols in Molecular Biology, Eds. Wiley and Sons. Methods for introduction of genetic material into host cells include, for example, transformation, electroporation, conjugation, calcium phosphate methods and the like. The method for transfer can be selected so as to provide for stable expression of the introduced polypeptide-encoding nucleic acid. The polypeptide-encoding nucleic acid can be provided as an inheritable episomal element (e.g., a plasmid) or can be genomically integrated. A variety of appropriate vectors for use in production of a polypeptide of interest are commercially available.

Vectors can provide for extrachromosomal maintenance in a host cell or can provide for integration into the host cell genome. The expression vector provides transcriptional and translational regulatory sequences, and may provide for inducible or constitutive expression where the coding region is operably-linked under the transcriptional control of the transcriptional initiation region, and a transcriptional and translational termination region. In general, the transcriptional and translational regulatory sequences may include, but are not limited to, promoter sequences, ribosomal binding sites, transcriptional start and stop sequences, translational start and stop sequences, and enhancer or activator sequences. Promoters can be either constitutive or inducible, and can be a strong constitutive promoter (e.g., T7). Expression constructs generally have convenient restriction sites located near the promoter sequence to provide for the insertion of nucleic acid sequences encoding proteins of interest. A selectable marker operative in the expression host may be present to facilitate selection of cells containing the vector. Moreover, the expression construct may include additional elements. For example, the expression vector may have one or two replication systems, thus allowing it to be maintained in organisms, for example, in mammalian or insect cells for expression and in a prokaryotic host for cloning and amplification. In addition, the expression construct may contain a selectable marker gene to allow the selection of transformed host cells. Selectable genes are well known in the art and will vary with the host cell used.

Isolation and purification of a protein can be accomplished according to methods known in the art. For example, a protein can be isolated from a lysate of cells genetically modified to express the protein constitutively and/or upon induction, or from a synthetic reaction mixture by immunoaffinity purification, which generally involves contacting the sample with an anti-protein antibody, washing to remove non-specifically bound material, and eluting the specifically bound protein. The isolated protein can be further purified by dialysis and other methods normally employed in protein purification methods. In one embodiment, the protein may be isolated using metal chelate chromatography methods. Proteins may contain modifications to facilitate isolation.

The polypeptides may be prepared in substantially pure or isolated form (e.g., free from other polypeptides). The polypeptides can be present in a composition that is enriched for the polypeptide relative to other components that may be present (e.g., other polypeptides or other host cell components). For example, purified polypeptide may be provided such that the polypeptide is present in a composition that is substantially free of other expressed proteins, e.g., less than 90%, less than 60%, less than 50%, less than 40%, less than 30%, less than 20%, less than 10%, less than 5%, or less than 1%, of the composition is made up of other expressed proteins.

Antibodies

The present disclosure provides antibodies, including isolated antibodies, that specifically bind a GDF15 polypeptide, e.g., a GDF15 mutein of the present disclosure. The term "antibody" encompasses intact monoclonal antibodies, polyclonal antibodies, multispecific antibodies (e.g., bispecific antibodies) formed from at least two intact antibodies, and antibody binding fragments including Fab and F(ab)′$_2$, provided that they exhibit the desired biological activity. The basic whole antibody structural unit comprises a tetramer, and each tetramer is composed of two identical pairs of polypeptide chains, each pair having one "light" chain (about 25 kDa) and one "heavy" chain (about 50-70 kDa). The amino-terminal portion of each chain includes a variable region of about 100 to 110 or more amino acids primarily responsible for antigen recognition. In contrast, the carboxy-terminal portion of each chain defines a constant region primarily responsible for effector function. Human light chains are classified as kappa and lambda, whereas human heavy chains are classified as mu, delta, gamma, alpha, or epsilon, and define the antibody's isotype as IgM, IgD, IgG, IgA, and IgE, respectively. Binding fragments are produced by recombinant DNA techniques, or by enzymatic or chemical cleavage of intact antibodies. Binding fragments include Fab, Fab', F(ab')2, Fv, and single-chain antibodies.

Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Within light and heavy chains, the variable and constant regions are joined by a "J" region of about 12 or more amino acids, with the heavy chain also including a "D" region of about 10 more amino acids. The antibody chains all exhibit the same general structure of relatively conserved framework regions (FR) joined by three hyper-variable regions, also called "complementarity-determining regions" or "CDRs". The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4.

An intact antibody has two binding sites and, except in bifunctional or bispecific antibodies, the two binding sites are the same. A bispecific or bifunctional antibody is an artificial hybrid antibody having two different heavy/light chain pairs and two different binding sites. Bispecific antibodies can be produced by a variety of methods including fusion of hybridomas or linking of Fab' fragments.

As set forth above, binding fragments may be produced by enzymatic or chemical cleavage of intact antibodies. Digestion of antibodies with the enzyme papain results in two identical antigen-binding fragments, also known as "Fab" fragments, and an "Fc" fragment which has no antigen-binding activity. Digestion of antibodies with the enzyme pepsin results in a F(ab')2 fragment in which the two arms of the antibody molecule remain linked and comprise two-antigen binding sites. The F(ab')2 fragment has the ability to crosslink antigen.

As used herein, the term "Fab" refers to a fragment of an antibody that comprises the constant domain of the light chain and the CH1 domain of the heavy chain.

When used herein, the term "Fv" refers to the minimum fragment of an antibody that retains both antigen-recognition and antigen-binding sites. In a two-chain Fv species, this region includes a dimer of one heavy-chain and one light-chain variable domain in non-covalent association. In a single-chain Fv species, one heavy-chain and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. While the six CDRs, collectively, confer antigen-binding specificity to the antibody, even a single variable domain (or half of an Fv comprising only three CDRs specific for an antigen) has the ability to recognize and bind antigen.

When used herein, the term "complementarity determining regions" or "CDRs" refers to parts of immunological receptors that make contact with a specific ligand and determine its specificity.

The term "hypervariable region" refers to the amino acid residues of an antibody which are responsible for antigen-binding. The hypervariable region generally comprises amino acid residues from a CDR and/or those residues from a "hypervariable loop".

As used herein, the term "epitope" refers to binding sites for antibodies on protein antigens. Epitopic determinants usually comprise chemically active surface groupings of molecules such as amino acids or sugar side chains, as well as specific three-dimensional structural and charge characteristics. An antibody is said to bind an antigen when the dissociation constant is ≤1 µM, ≤100 nM, or ≤10 nM. An increased equilibrium constant ("KD") means that there is less affinity between the epitope and the antibody, whereas a decreased equilibrium constant means that there is more affinity between the epitope and the antibody. An antibody with a KD of "no more than" a certain amount means that the antibody will bind to the epitope with the given KD or more strongly. Whereas KD describes the binding characteristics of an epitope and an antibody, "potency" describes the effectiveness of the antibody itself for a function of the antibody. There is not necessarily a correlation between an equilibrium constant and potency; thus, for example, a relatively low $K_D$ does not automatically mean a high potency.

The term "selectively binds" in reference to an antibody does not mean that the antibody only binds to a single substance, but rather that the $K_D$ of the antibody to a first substance is less than the $K_D$ of the antibody to a second substance. An antibody that exclusively binds to an epitope only binds to that single epitope.

When administered to humans, antibodies that contain rodent (i.e., murine or rat) variable and/or constant regions are sometimes associated with, for example, rapid clearance from the body or the generation of an immune response by the body against the antibody. In order to avoid the utilization of rodent-derived antibodies, fully human antibodies can be generated through the introduction of human antibody function into a rodent so that the rodent produces fully human antibodies. Unless specifically identified herein, "human" and "fully human" antibodies can be used interchangeably. The term "fully human" can be useful when distinguishing antibodies that are only partially human from those that are completely, or fully, human. The skilled artisan is aware of various methods of generating fully human antibodies.

In order to address possible human anti-mouse antibody responses, chimeric or otherwise humanized antibodies can be utilized. Chimeric antibodies have a human constant region and a murine variable region, and, as such, human anti-chimeric antibody responses may be observed in some patients. Therefore, it is advantageous to provide fully human antibodies against multimeric enzymes in order to avoid possible human anti-mouse antibody or human anti-chimeric antibody responses.

Fully human monoclonal antibodies can be prepared, for example, by the generation of hybridoma cell lines by techniques known to the skilled artisan. Other preparation methods involve the use of sequences encoding particular antibodies for transformation of a suitable mammalian host cell, such as a CHO cell. Transformation can be by any known method for introducing polynucleotides into a host cell, including, for example, packaging the polynucleotide in a virus (or into a viral vector) and transducing a host cell with the virus (or vector) or by transfection procedures known in the art. Methods for introducing heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. Mammalian cell lines available as hosts for expression are well known in the art and include, but are not limited to, CHO cells, HeLa cells, and human hepatocellular carcinoma cells.

The antibodies can be used to detect a Polypeptide of the present disclosure. For example, the antibodies can be used as a diagnostic by detecting the level of one or more Polypeptides of the present disclosure in a subject, and either comparing the detected level to a standard control level or to a baseline level in a subject determined previously (e.g., prior to any illness).

Another embodiment of the present disclosure entails the use of one or more human domain antibodies (dAb). dAbs are the smallest functional binding units of human antibodies (IgGs) and have favorable stability and solubility characteristics. The technology entails a dAb(s) conjugated to HSA (thereby forming a "AlbudAb"; see, e.g., EP1517921B, WO2005/118642 and WO2006/051288) and a molecule of interest (e.g., a polypeptide sequence of the present disclosure). AlbudAbs are often smaller and easier to manufacture in microbial expression systems, such as bacteria or yeast, than current technologies used for extending the serum half-life of polypeptides. As HSA has a half-life of about three weeks, the resulting conjugated molecule improves the half-life of the molecule of interest. Use of the dAb technology may also enhance the efficacy of the molecule of interest.

Therapeutic and Prophylactic Uses

The present disclosure provides methods for treating or preventing hyperglycemia, hyperinsulinemia, glucose intolerance, glucose metabolism disorders, obesity and other body weight disorders, as well as other metabolic and metabolic-associated diseases, disorders and conditions by the administration of the Polypeptides, or compositions thereof, as described herein. Such methods may also have an advantageous effect on one or more symptoms associated with a disease, disorder or condition by, for example, decreasing the severity or the frequency of a symptom.

In order to determine whether a subject may be a candidate for the treatment or prevention of hyperglycemia, hyperinsulinemia, glucose intolerance, and/or glucose disorders by the methods provided herein, various diagnostic methods known in the art may be utilized. Such methods include those described elsewhere herein (e.g., fasting plasma glucose (FPG) evaluation and the oral glucose tolerance test (oGTT)).

In order to determine whether a subject may be a candidate for the treatment or prevention of a body weight disorder (e.g., obesity) by the methods provided herein, parameters such as, but not limited to, the etiology and the extent of the subject's condition (e.g., how overweight the subject is compared to reference healthy individual) should be evaluated. For example, an adult having a BMI between ~25 and ~29.9 kg/m$^2$ may be considered overweight (pre-obese), while an adult having a BMI of ~30 kg/m$^2$ or higher may be considered obese. For subjects who are overweight and/or who have poor diets (e.g., diets high in fat and calories), it is common to initially implement and assess the effect of modified dietary habits and/or exercise regimens before initiating a course of therapy comprising one or more of the Polypeptides of the present disclosure. As discussed herein, the Polypeptides can effect appetite suppression.

Pharmaceutical Compositions

The Modulators (e.g., Polypeptides) of the present disclosure may be in the form of compositions suitable for administration to a subject. In general, such compositions are "pharmaceutical compositions" comprising one or more Modulators and one or more pharmaceutically acceptable or physiologically acceptable diluents, carriers or excipients. In certain embodiments, the Modulators are present in a therapeutically acceptable amount. The pharmaceutical compositions may be used in the methods of the present disclosure; thus, for example, the pharmaceutical compositions can be administered ex vivo or in vivo to a subject in order to practice the therapeutic and prophylactic methods and uses described herein.

The pharmaceutical compositions of the present disclosure can be formulated to be compatible with the intended method or route of administration; exemplary routes of administration are set forth herein. Furthermore, the pharmaceutical compositions may be used in combination with other therapeutically active agents or compounds (e.g., glucose lowering agents) as described herein in order to treat or prevent the diseases, disorders and conditions as contemplated by the present disclosure.

The pharmaceutical compositions typically comprise a therapeutically effective amount of at least one of the Modulators (e.g., Polypeptides) contemplated by the present disclosure and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that could be used in the pharmaceutical compositions and dosage forms. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments. Any drug delivery apparatus may be used to deliver the Polypeptides, including implants (e.g., implantable pumps) and catheter systems, both of which are well known to the skilled artisan. Depot injections, which are generally administered subcutaneously or intramuscularly, may also be utilized to release the polypeptides disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed including synthetic mono- or diglycerides. Moreover, fatty acids such as oleic acid find use in the preparation of injectables. Prolonged absorption of particular injectable formulations can be achieved by including an agent that delays absorption (e.g., aluminum monostearate or gelatin).

The pharmaceutical compositions containing the active ingredient may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly(methylmethacrolate) microcapsules, respectively, or in a colloid drug delivery system. Colloidal dispersion systems include macromolecule complexes, nanocapsules, microspheres, microbeads, and lipid-based systems, including oil-in-water emulsions, micelles, mixed micelles, and liposomes. Methods of preparing liposomes are described in, for example, U.S. Pat. Nos. 4,235,871, 4,501, 728, and 4,837,028. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present disclosure may also be in the form of oil-in-water emulsions. The oily phase may be a vegetable oil, for example olive oil or arachis oil, or a mineral oil, for example, liquid paraffin, or mixtures of these. Suitable emulsifying agents may be naturally-occurring gums, for example, gum acacia or gum tragacanth; naturally-occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

Formulations can also include carriers to protect the composition against rapid degradation or elimination from the body, such as a controlled release formulation, including implants, liposomes, hydrogels, prodrugs and microencapsulated delivery systems. For example, a time delay material such as glyceryl monostearate or glyceryl stearate alone, or in combination with a wax, may be employed.

The present disclosure contemplates the administration of the Modulators in the form of suppositories for rectal administration of the drug. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The Modulators contemplated by the present disclosure may be in the form of any other suitable pharmaceutical composition (e.g., sprays for nasal or inhalation use) currently known or developed in the future.

The concentration of a polypeptide or fragment thereof in a formulation can vary widely (e.g., from less than about 0.1%, usually at or at least about 2% to as much as 20% to 50% or more by weight) and will usually be selected primarily based on fluid volumes, viscosities, and subject-based factors in accordance with, for example, the particular mode of administration selected.

Routes of Administration

The present disclosure contemplates the administration of the disclosed Modulators (e.g., Polypeptides), and compositions thereof, in any appropriate manner. Suitable routes of administration include parenteral (e.g., intramuscular, intravenous, subcutaneous (e.g., injection or implant), intraperitoneal, intracisternal, intraarticular, intraperitoneal, intracerebral (intraparenchymal) and intracerebroventricular), oral, nasal, vaginal, sublingual, intraocular, rectal, topical (e.g., transdermal), sublingual and inhalation.

Depot injections, which are generally administered subcutaneously or intramuscularly, may also be utilized to release the Modulators disclosed herein over a defined period of time. Depot injections are usually either solid- or oil-based and generally comprise at least one of the formulation components set forth herein. One of ordinary skill in the art is familiar with possible formulations and uses of depot injections.

Regarding antibodies, in an exemplary embodiment an antibody or antibody fragment of the present disclosure is stored at 10 mg/ml in sterile isotonic aqueous saline solution for injection at 4° C. and is diluted in either 100 ml or 200 ml 0.9% sodium chloride for injection prior to administration to the subject. The antibody is administered by intravenous infusion over the course of 1 hour at a dose of between 0.2 and 10 mg/kg. In other embodiments, the antibody is administered by intravenous infusion over a period of between 15 minutes and 2 hours. In still other embodiments, the administration procedure is via subcutaneous bolus injection.

Combination Therapy

The present disclosure contemplates the use of the Modulators (e.g., Polypeptides) in combination with one or more active therapeutic agents or other prophylactic or therapeutic modalities. In such combination therapy, the various active agents frequently have different mechanisms of action. Such combination therapy may be especially advantageous by allowing a dose reduction of one or more of the agents, thereby reducing or eliminating the adverse effects associated with one or more of the agents; furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, the Modulators are administered or applied sequentially, e.g., where one agent is administered prior to one or more other agents. In other embodiments, the Modulators are administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present disclosure.

The Modulators of the present disclosure can be used in combination with other agents useful in the treatment, prevention, suppression or amelioration of the diseases, disorders or conditions set forth herein, including those that are normally administered to subjects suffering from hyperglycemia, hyperinsulinemia, glucose intolerance, and other glucose metabolism disorders.

The present disclosure contemplates combination therapy with numerous agents (and classes thereof), including 1) insulin, insulin mimetics and agents that entail stimulation of insulin secretion, including sulfonylureas (e.g., chlorpropamide, tolazamide, acetohexamide, tolbutamide, glyburide, glimepiride, glipizide) and meglitinides (e.g., repaglinide (PRANDIN) and nateglinide (STARLIX)); 2) biguanides (e.g., metformin (GLUCOPHAGE)) and other agents that act by promoting glucose utilization, reducing hepatic glucose production and/or diminishing intestinal glucose output; 3) alpha-glucosidase inhibitors (e.g., acarbose and miglitol) and other agents that slow down carbohydrate digestion and consequently absorption from the gut and reduce postprandial hyperglycemia; 4) thiazolidinediones (e.g., rosiglitazone (AVANDIA), troglitazone (REZULIN), pioglitazone (ACTOS), glipizide, balaglitazone, rivoglitazone, netoglitazone, troglitazone, englitazone, ciglitazone, adaglitazone, darglitazone that enhance insulin action (e.g., by insulin sensitization), thus promoting glucose utilization in peripheral tissues; 5) glucagon-like-peptides including DPP-IV inhibitors (e.g., vildagliptin (GALVUS) and sitagliptin (JANUVIA)) and Glucagon-Like Peptide-1 (GLP-1) and GLP-1 agonists and analogs (e.g., exenatide (BYETTA)); 6) and DPP-IV-resistant analogues (incretin mimetics), PPAR gamma agonists, dual-acting PPAR agonists, pan-acting PPAR agonists, PTP1B inhibitors, SGLT inhibitors, insulin secretagogues, RXR agonists, glycogen synthase kinase-3 inhibitors, immune modulators, beta-3 adrenergic receptor agonists, 11beta-HSD1 inhibitors, and amylin analogues.

Furthermore, the present disclosure contemplates combination therapy with agents and methods for promoting weight loss, such as agents that stimulate metabolism or decrease appetite, and modified diets and/or exercise regimens to promote weight loss.

The Modulators of the present disclosure may be used in combination with one or more other agent in any manner appropriate under the circumstances. In one embodiment, treatment with the at least one active agent and at least one Modulator of the present disclosure is maintained over a period of time. In another embodiment, treatment with the at least one active agent is reduced or discontinued (e.g., when the subject is stable), while treatment with the Modulator of the present disclosure is maintained at a constant dosing regimen. In a further embodiment, treatment with the at least one active agent is reduced or discontinued (e.g., when the subject is stable), while treatment with the Modulator of the present disclosure is reduced (e.g., lower dose, less frequent dosing or shorter treatment regimen). In yet another embodiment, treatment with the at least one active agent is reduced or discontinued (e.g., when the subject is stable), and treatment with the Modulator of the present disclosure is increased (e.g., higher dose, more frequent dosing or longer treatment regimen). In yet another embodiment, treatment with the at least one active agent is maintained and treatment with the Modulator of the present disclosure is reduced or discontinued (e.g., lower dose, less frequent dosing or shorter treatment regimen). In yet another embodiment, treatment with the at least one active agent and treatment with the Modulator of the present disclosure are reduced or discontinued (e.g., lower dose, less frequent dosing or shorter treatment regimen).

Dosing

The Modulators (e.g., Polypeptides) of the present disclosure may be administered to a subject in an amount that is dependent upon, for example, the goal of the administration (e.g., the degree of resolution desired); the age, weight, sex, and health and physical condition of the subject to be treated; the nature of the Modulator, and/or formulation being administered; the route of administration; and the nature of the disease, disorder, condition or symptom thereof (e.g., the severity of the dysregulation of glucose/insulin and the stage of the disorder). The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (i.e., the maximum tolerated dose, "MTD") and not less than an amount required to produce a measurable effect on the subject. Such amounts are determined by, for example, the pharmacokinetic and pharmacodynamic parameters associated with absorption, distribution, metabolism, and excretion ("ADME"), taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated ED50, in other situations the effective amount is less than the calculated ED50, and in still other situations the effective amount is the same as the calculated ED50.

In addition, an effective dose of the Modulators of the present disclosure may be an amount that, when administered in one or more doses to a subject, produces a desired result relative to a healthy subject. For example, an effective dose may be one that, when administered to a subject having elevated plasma glucose and/or plasma insulin, achieves a desired reduction relative to that of a healthy subject by at least about 10%, at least about 20%, at least about 25%, at least about 30%, at least about 40%, at least about 50%, at least about 60%, at least about 70%, at least about 80%, or more than 80%.

An appropriate dosage level will generally be about 0.001 to 100 mg/kg of patient body weight per day, which can be administered in single or multiple doses. In some embodiments, the dosage level will be about 0.01 to about 25 mg/kg per day, and in other embodiments about 0.05 to about 10 mg/kg per day. A suitable dosage level may be about 0.01 to 25 mg/kg per day, about 0.05 to 10 mg/kg per day, or about 0.1 to 5 mg/kg per day. Within this range, the dosage may be 0.005 to 0.05, 0.05 to 0.5 or 0.5 to 5.0 mg/kg per day.

For administration of an oral agent, the compositions can be provided in the form of tablets, capsules and the like containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient. The Modulators may be administered on a regimen of, for example, 1 to 4 times per day, and often once or twice per day.

The dosage of the Modulators of the present disclosure may be repeated at an appropriate frequency, which may be in the range of once per day to once every three months, depending on the pharmacokinetics of the Modulators (e.g. half-life) and the pharmacodynamic response (e.g. the duration of the therapeutic effect of the Modulator). In some embodiments where the Modulator is an antibody or a fragment thereof, or a polypeptide or variants thereof, dosing is frequently repeated between once per week and once every 3 months. In other embodiments, such Modulators are administered approximately once per month.

In certain embodiments, the dosage of the disclosed Modulators is contained in a "unit dosage form". The phrase "unit dosage form" refers to physically discrete units, each unit containing a predetermined amount of a Modulator of the present disclosure, either alone or in combination with one or more additional agents, sufficient to produce the desired effect. It will be appreciated that the parameters of a unit dosage form will depend on the particular agent and the effect to be achieved.

Kits

The present disclosure also contemplates kits comprising the disclosed Modulators (e.g., Polypeptides), and pharmaceutical compositions thereof. The kits are generally in the form of a physical structure housing various components, as described below, and may be utilized, for example, in practicing the methods described above (e.g., administration of a Modulator to a subject in need of restoring glucose homeostasis).

A kit can include one or more of the Modulators disclosed herein (provided in, e.g., a sterile container), which may be in the form of a pharmaceutical composition suitable for administration to a subject. The Modulators can be provided in a form that is ready for use or in a form requiring, for example, reconstitution or dilution prior to administration. When the Modulators are in a form that needs to be reconstituted by a user, the kit may also include buffers, pharmaceutically acceptable excipients, and the like, packaged with or separately from the Modulators. When combination therapy is contemplated, the kit may contain the several agents separately or they may already be combined in the kit. Each component of the kit can be enclosed within an individual container and all of the various containers can be within a single package. A kit of the present disclosure can be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampoule, tube or vial). Exemplary instructions include those for reducing or lowering blood glucose, treatment of hyperglycemia, treatment of diabetes, etc. with the disclosed Modulators, and pharmaceutical compositions thereof.

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: bp=base pair(s); kb=kilobase(s); pl=picoliter(s); s or sec=second(s); min=minute(s); h or hr=hour(s); aa=amino acid(s); kb=kilobase(s); nt=nucleotide(s); ng=nanogram; μg=microgram; mg=milligram; g=gram; kg=kilogram; dl or dL=deciliter; μl or μL=microliter; ml or mL=milliliter; l or L=liter; μM=micromolar; mM=millimolar; M=molar; kDa=kilodalton; i.m.=intramuscular(ly); i.p.=intraperitoneal(ly); s.c.=subcutaneous(ly); bid=twice daily; HPLC=high performance liquid chromatography; BW=body weight; U=unit; ns=not statistically significant; PG=fasting plasma glucose; FPI=fasting plasma insulin; ITT=insulin tolerance test; PTT=pyruvate tolerance test; oGTT=oral glucose tolerance test; GSIS=glucose-stimulated insulin secretion; PBS=phosphate-buffered saline; PCR=polymerase chain reaction; NHS=N-Hydroxysuccinimide; DMEM=Dulbeco's Modification of Eagle's Medium; GC=genome copy; EDTA=ethylenediaminetetraacetic acid.

Materials and Methods

The following methods and materials were used in the Examples below:

Animals. Seven-fifteen—week old male B6.V-LEP$^{ob}$/J (leptin-deficient (ob/ob)) mice (The Jackson Laboratory, Bar Harbor, Me.) were used in the experiments described hereafter. Mice had free access to autoclaved distilled water and were fed ad libitum a commercial mouse chow (Irradiated 2018 Teklad Global 18% protein Rodent Diet, Harlan Laboratories, Dublin, Va.). All animal studies were approved by the NGM Institutional Animal Care and Use Committee.

Nucleic Acid and Amino Acid Sequences. GenBank Accession No. BC000529.2 sets forth the cDNA of ORF encoding human GDF15 variants, and GenBank Accession No. NP_004855.2 sets forth the amino acid sequence encoded by the cDNA. *Homo sapiens* serum albumin cDNA was purchased from Origene (SC319937), GeneBank Accession No. NM_000477.3, NP_000468).

Fusion PCR fragments for HSA and human GDF15 were generated by Sapphire (Clontech) enzyme, gel purified (Qiagen Gel Extraction kit) and assembled with Gibson Assembly Master Mix (NEB) into pTT5 vector containing the human IgK signal peptide digested with EcoRI and BamHI. Two PCR fragments were generated for cloning, the first encoding HSA and the second encoding human GDF15. The following primers were used for amplifying HSA: forward primer: 5'-tggctccgaggtgccagatgtgatgcacacaagagtgaggttgctcatcgg-3' (SEQ ID NO:76); reverse primer: 5'-gctaccgcctccacctaagcctaaggcagcttgacttgc-3' (SEQ ID NO:77). The following primers were used for amplifying GDF15: forward primer: 5'-gctgccttaggcttaggtggaggcgg-tagcggtggaggtgggagtggaggtg-gaggcagtgcgcgcaacggggaccactgtccgctc ggg-3'(SEQ ID NO:78); reverse primer: 5'-cagaggtcgaggtcggggggatcct-catatgcagtggcagtctttggctaacaa-3' (SEQ ID NO:79).

Colonies were plated and sequence confirmed. Primers were designed to mutate regions of interest, and mutagenesis was performed with Quikchange Lightning Site Directed Mutagenesis Kit (Agilent). Sequence-confirmed colonies were amplified and plasmid DNA was purified using Qiagen DNA-Maxi prep kit.

HSA-GDF15 Mutein Fusion Molecule Expression. All muteins were transiently transfected in Expi 293F cells (Invitrogen Corporation, Carlsbad, Calif.). Cells were routinely subcultured in Expi expression medium (Invitrogen) and maintained as suspension cultures in shake flasks of varying sizes. Typically, cells were subcultured at a cell density of 5e5 viable cells/ml and grown for 3 days before subculturing. The flasks were maintained in a humidified $CO_2$ incubator (37° C. and 5% $CO_2$) on New Brunswick shaker platforms (New Brunswick Scientific Company, Edison, N.J.) at an agitation rate of 110 RPM.

Transfections were performed when the cell density of the culture reached 2.5e6 viable cells/ml at greater than 95% viability. Typically, for 50 ml transfection, 2.5e6 cells/mL×50 mL cells were inoculated in a 250 mL shaker flask in 42.5 mL culture volume. Fifty micrograms (50 μg) plasmid DNA consisting of the expression vector containing the gene of interest was first diluted in 2.5 mL OPTI-MEM reduced-serum medium (Invitrogen). Simultaneously, Expifectamine transfection reagent (Invitrogen), 2.67 times the volume (of the amount of plasmid DNA) was also diluted in 2.5 mL OPTI-MEM reduced-serum medium. After a 5 min incubation at room temperature, the diluted transfection reagent was slowly added to the diluted plasmid DNA to form transfection competent complexes. After a further 20 min incubation period at room temperature, 5 mL of the transfection complex was added to the 42.5 mL cell culture. The transfected cells were then placed in the humidified $CO_2$ incubator on an orbital shaker maintained at 110 RPM. Twenty-four hours post-transfection, the transfected culture was fed with 250 μL enhancer 1 solution (Invitrogen) and 2.5 ml enhancer 2 solution (Invitrogen). The culture was then replaced in the humidified $CO_2$ incubator on an orbital shaker. Six-to-seven days post-transfection, cultures were harvested by centrifugation at 3000 RPM for 30 min before being filtered through a 0.2 μm filter (Nalgene). Samples were then analyzed on a commassie stain gel for expression.

Cleavage of HSA-GDF15 Fusion Molecules. Human Serum Albumin hGDF15 fusion constructs were purified to greater than 95% homogeneity. Muteins were excised via overnight digestion at Room Temperature using Factor Xa obtained from New England Biolabs (P8010) using a 1:500 (w/w) addition (in 1X phosphate buffered saline). Following cleavage, GDF15 muteins were purified to greater than 95% homogeneity.

Solubility assessment of human GDF15 muteins. Muteins were dialyzed into 1X phosphate buffered saline and concentrated using Amicon Ultra Centrifugal Filters composed of Regenerated Nitrocellulose 10,000 NMWL (UFC901096). Following concentration, solubility assessments were performed on a NanoDrop ND-1000 spectrophotometer blanked in 1X Phosphate Buffered Saline using Absorbance at 280 nm wavelength and Beer's law (Extinction coefficient=14400, Molecular weight=12,287 Da).

Blood Glucose Assay. Blood glucose from mouse tail snip was measured using ACCU-CHEK Active test strips read by ACCU-CHEK Active meter (Roche Diagnostics, Indianapolis, Ind.) following manufacturer's instruction.

Serum GDF15 Muteins Exposure Level Assay. Whole blood (~50 µl/mouse) from mouse tail snips was collected into plain capillary tubes (BD Clay Adams SurePrep, Becton Dickenson, Sparks, Md.). Serum and blood cells were separated by spinning the tubes in an Autocrit Ultra 3 (Becton Dickinson, Sparks, Md.). GDF15 exposure levels in serum were determined using Human GDF-15 Quantikine ELISA Kit (R&D Systems, Minneapolis, Minn.) by following the manufacturer's instructions.

Analytical Gel Filtration. Increases to hydrodynamic radii of engineered human GDF15 muteins was monitored via A280 elution absorbance on an Agilent 1200-series HPLC elution times (min) using a TOSOH Biosciences TSKgelG3000SW$_{XL}$ column (7.8 mm ID×30 cm, 5 µm), pre-equilibrated with 1X phosphate buffered saline with flow rate of 1 mL/min.

Example 1

Effects of a HSA-GDF15 Fusion Molecule on Body Weight, Food Intake and Fasted Blood The effects of a subcutaneously administered fusion molecule having recombinant HSA fused to recombinant human GDF15 on body weight, food intake, and fasted blood glucose were evaluated over a 22 day period post-delivery. Briefly, the fusion molecule depicted in FIG. 1H (mature HSA fused to the N-terminus of mature human GDF15 through a non-cleavable 3x(4Gly-Ser linker) linker) was administered, at various doses, as a single, subcutaneous bolus injection to 7-15 week old male ob/ob mice weighing approximately 44 g and having non-fasted glucose serum levels of approximately 340 mg/dl. Following administration of vehicle control (PBS) or the fusion molecule at doses of 0.04 mg/kg, 0.12 mg/kg, 0.4 mg/kg and 1.2 mg/kg, the indicated parameters were determined over a 22-day period on days 0, 2, 3, 6, 8, 15 and 22. Serum exposure was monitored by Human GDF-15 Quantikine ELISA Kit (R&D Systems, Minneapolis, Minn.) following the manufacturer's instructions.

The fusion molecule demonstrated an improved half-life of 37 hours compared to a half-life of 2 hours for unconjugated, recombinant human GDF15. Additionally, whereas the solubility of human GDF15 is less than 0.2 mg/mL in vehicle control buffer (1×PBS), the fusion molecule improved solubility to more than 50 mg/mL in vehicle control buffer (1×PBS).

As depicted in FIG. 2, administration of the fusion molecule at doses of 0.04 mg/kg, 0.12 mg/kg, 0.4 mg/kg and 1.2 mg/kg resulted in significant improvement in body weight (FIG. 2A), food intake (FIG. 2B), and non-fasted blood glucose (FIG. 2C) compared to vehicle control. In each group of mice, n=7 and p-values (*, p<0.05; , p<0.01; *, p<0.001) were determined by student's unpaired T-test comparing the body weight, food intake and blood glucose groups at the various concentrations to vehicle control group at each specified time point.

Referring to FIG. 2A, 22 days post-administration of the fusion molecule at the indicated doses compared to 22 days post-administration of vehicle control (PBS-injected ob/ob mice (52.5 g)) resulted in the following body weight reductions: a decrease of 1.7 g comprising a percent decrease of 3.2% (ns) for the 0.04 mg/kg dose group; a decrease of 1.8 g comprising a percent decrease of 3.5% (ns) for the 0.12 mg/kg dose group; a decrease of 1.9 g comprising a percent decrease of 3.6% (*, p<0.05) for the 0.40 mg/kg dose group; and a decrease of 3.2 g comprising a percent decrease of 6.1% (**, p<0.01) for the 1.2 mg/kg dose group.

Food intake (grams/animal/day) in ob/ob mice administered vehicle control or the fusion molecule at the indicated doses was assessed at various times during the 22 day post-administration observation period. Referring to the 9-15 day time period in FIG. 2B, average food intake relative to vehicle control (PBS)-injected ob/ob mice (7.88 g/animal/day) was as follows: average food intake decreased 0.24 g/animal/day, which comprised a percent decrease of 3.0% (ns) for 0.04 mg/kg dose group; decreased 0.92 g/animal/day, which comprised a percent decrease of 11.7% (ns) for 0.12 mg/kg dose group; decreased 1.70 g/animal/day, which comprised a percent decrease of 21.5% (, p<0.01) for 0.40 mg/kg dose group; and decreased 2.31 g/animal/day, which comprised a percent decrease of 29.3% (, p<0.01) for 1.2 mg/kg dose group.

Non-fasted blood glucose (mg/dL) in ob/ob mice administered vehicle control or the fusion molecule at the indicated doses was assessed at various time points during the 22 day post-administration observation period. Referring to FIG. 2C, relative to vehicle control (PBS)-injected ob/ob mice (day 8=357.4 mg/dL), non-fasted blood glucose levels on day 8 demonstrated a decrease of 3.9 mg/dl, which comprised a percent decrease of 1.1% (ns) for 0.04 mg/kg dose group; a decrease of 62.7 mg/dL, which comprised a percent decrease of 17.5% (ns) for 0.12 mg/kg dose group; a decrease of 106.1 mg/dL, which comprised a percent decrease of 29.7% (*, p<0.05) for 0.40 mg/kg dose group; and a decrease of 191.1 mg/dL, which comprised a percent decrease of 53.5% (**, p<0.01) for 1.2 mg/kg dose group.

The data in FIG. 2 demonstrate that an HSA fusion with GDF15 is active, and that such fusion molecules represent a viable approach for enhancing certain beneficial properties of GDF15 muteins. The data also indicate that measurement of the indicated parameters may be useful as a platform for high-throughput screening of muteins.

Example 2

Improvement of GDF15 Properties via Reduction of Surface Hydrophobicity

In an effort to identify means for improving the physical properties (e.g., solubility and stability) of mature human GDF15, a set of six hydrophobic residues predicted to be surface-accessible were mutated to alanine as a means of increasing surface hydrophobicity.

Fusion molecules were generated wherein each of the six GDF15 mutein sequences was fused to HSA through the linker depicted in FIG. 1H (a non-cleavable 3x(4Gly-Ser linker) linker); the sequences set forth in FIG. 3 neither depict the HSA component nor the linker component of the fusion molecules.

The fusion molecules were then monitored for expression as secreted disulfide-linked homodimers. FIG. 4 summarizes the data for each fusion molecule. The first two columns identify the residue of the mature human GDF15 that was mutated, the third column identifies those native residues that were substituted by alanine, and the fourth column indicates whether each resultant fusion molecule was expressed as a secreted dimer. Five of the six hydrophobicity-reduction muteins expressed and secreted as disulfide linked homodimers and were further evaluated for improvements in physical properties (w65 was not expressed as a homodimer and was not pursued further).

Example 3

Human GDF15 Muteins with Improved Solubility Characteristics

The data set forth in Example 2 were used to address solubility limitations associated with surface hydrophobicities inherent to mature human GDF15. In addition, the effect on solubility of introducing N-linked Glycosylation consensus site(s) along the sequence of mature human GDF15 was evaluated.

In order to facilitate assessment of solubility and determination of in vivo efficacy, mature, recombinant human GDF15 and GDF15 muteins were constructed as N-terminal HSA fusion molecules containing a Factor Xa proteolytic-sensitive linker (a 2x(4Gly-Ser) Factor Xa cleavable linker; as described in FIG. 1F) to allow for excision of the GDF15 or the GDF15 mutein from the HSA chaperone using Factor Xa digestion. Solubility assessments were performed in 1X PBS, a stringent buffer for which improvements in the solubility of a mutein can be assessed relative to mature human GDF15 (which has a maximum solubility of <0.2 mg/mL).

Assessment of solubility was determined based on Absorbance at 280 nm using Beer's law calculated using Extinction Coefficient (mature human GDF15=14,400/monomer) and molecular weight (mature human GDF15=12,278 Da/monomer). Muteins were categorized into one of five groups depending on their level of solubility: 0.0-0.2 mg/mL=+; 0.2-0.5 mg/mL=++; 0.5-1.0 mg/mL=+++; 1.0-5.0 mg/mL=++++; and >5.0 mg/mL=+++++.

Reduction of surface hydrophobicity of five of the GDF15 muteins (w29, w32, w52, w68 and w89) set forth in FIG. 5 was assessed via selective mutagenesis of hydrophobic residues to alanine Comparison of the relative solubility of these five muteins to mature human GDF15 indicated that w52 and w89 were the only muteins in this class that exhibited improved solubility (++) relative to mature human GDF15 (+). The other three muteins exhibited solubility within the same range as mature human GDF15.

Reduction of the surface hydrophilicity of human GDF15 was assessed via selective mutagenesis of acidic residues to alanine with the five sequences denoted in FIG. 5 and summarized hereafter: w113, w114, w115, w116 and w117. Comparison of the relative solubility of these five muteins to mature human GDF15 indicated w116 was the only mutein in this class that exhibited improved solubility (++) relative to mature human GDF15 (+). Of the other four muteins, w113 and w115 exhibited solubility within the same range as mature human GDF15, while muteins w114 and w117 were insoluble under the conditions employed.

Next, the mature human GDF15 sequence was assessed for its ability to accommodate introduction of N-linked Glycosylation consensus site(s). In this context, a single amino acid substitution would impart the required consensus site within the mature human GDF15 sequence, the consensus site for N-linked glycosylation being defined as "Asn-Xxx-Ser/Thr", where "Xxx" cannot be a proline residue. Based on a scan of the mature human GDF15 sequence, 14 possible single-point muteins were identified that would accommodate introduction of the N-Glycan consensus site. FIG. 6 depicts the sequences of the 14 mono-glycosylation muteins, as well as additional combinatorial di-Glycosylation muteins.

Before being assessed for solubility, each of the engineered N-Glycan muteins set forth in FIG. 6 was evaluated both for secretion as a folded GDF15 homodimer into mammalian tissue culture media and for N-glycan site occupancy. As set forth in FIG. 7, ten of the fourteen mono-glycosylated muteins were secreted as folded GDF15 homodimers, whereas muteins w123, w125, w127 and w129 did not result in dimer formation. The ten mono-glycosylation muteins that secreted as homodimers were then assessed by LC/MS and SDS-PAGE gel shift to determine occupancy of N-Glycan groups on the consensus site; two of these muteins (w121 and w124) exhibited low occupancy and their solubility was not subsequently evaluated.

Engineered N-Glycan GDF15 muteins which were both secreted as homodimers and possessed high glycan occupancy within the consensus site were monitored for improvements to solubility relative to mature human GDF15. Each of the N-Glycan GDF15 muteins that was assessed exhibited improved solubility compared to mature human GDF15: w118: +++; w120: ++++; w122: ++; w126: ++++; w128: ++++; w130: ++++; w131: ++++; w132n: ++++; w133: ++++; w134: ++++; w135: +++++; w136: ++++; w137: ++++; w138: +++++; w139: +++++; and w140: +++++.

Acute in vivo efficacy was confirmed for those human mono-glycosylated GDF15 muteins which displayed improved solubility compared to mature human GDF15. Following subcutaneous administration of a single 0.3 mg/kg dose of mature human GDF15 or a N-glycan mutein to 7-15 week-old male ob/ob mice (n=7), food intake (grams/animal) over a 16-hour overnight period was monitored relative to a vehicle (PBS) control group. Three cohorts of mice were evaluated, and p-values were determined by an unpaired student T-test.

Referring to FIG. 9, in the first cohort of mice, food intake decreased an average of 0.82 g/animal (a percent decrease of 17.3% (*, $p<0.001$)), for the mature human GDF15 dose group; decreased 0.16 g/animal (a percent decrease of 3.4% (ns)) for the w120 dose group; decreased 0.87 g/animal (a percent decrease of 18.3% (*, $p<0.001$)) for the w128 dose group; decreased 0.77 g/animal (a percent decrease of 16.2% (***, $p<0.001$)) for the w130 dose group; and decreased 0.45 g/animal (a percent decrease of 9.4% (*, $p<0.05$)), for the w131 dose group. The average food intake for the vehicle control dose group was 4.76 g/animal.

For the second cohort of mice, food intake decreased an average of 0.77 g/animal (a percent decrease of 17.1% (*, $p<0.05$)) for the wild-type human GDF15 dose group; decreased 0.35 g/animal (a percent decrease of 7.9% (ns)) for the w118 dose group; and decreased 0.59 g/animal (a percent decrease of 13.0% (*, $p<0.05$)) for the w126 dose group. The average food intake for the vehicle control dose group was 4.53 g/animal.

For the third cohort of mice, food intake decreased an average of 1.10 g/animal (a percent decrease of 23.4% (*, $p<0.001$)) for the wild-type human GDF15 dose group; and decreased 1.29 g/animal (a percent decrease of 27.4% (*, $p<0.001$)) for the w122 dose group. The average food intake for the vehicle control dose group was 4.70 g/animal.

Example 4

Analytical Gel Filtration Analysis of Engineered N-Glycan GDF15 Muteins

Hydrodynamic radii of GDF15 N-Glycan muteins were assessed relative to mature human GDF15 utilizing analytical gel filtration chromatography (see FIG. 10). A TOSOH Biosciences TSKgelG3000SW$_{XL}$ (7.8 mm ID×30 cm, 5 μm) analytical sizing column pre-equilibrated in 1X phosphate buffered saline with flow rate of 1 mL/min was used in the evaluation. Two μg of each GDF15 mutein were injected in a 20 μL volume (0.1 mg/mL), and elution times were recorded at maximum absorbance during elution of the bell-shaped curve via measurement at 280 nm.

Analytical gel filtration chromatography of mature human GDF15 indicated a non-aggregated, disulfide-linked homodimer eluting at 10.837 minutes (FIG. 10). Each of the N-linked glycan muteins increased the hydrodynamic radii of the human GDF15 disulfide-linked dimer. Thus, each mutein may potentially serve as a starting point for generating molecules having, for example, a favorable in vivo half-life.

Particular embodiments of this invention are described herein, including the best mode known to the inventors for carrying out the invention. Upon reading the foregoing description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:

1. A polypeptide comprising the amino acid sequence of SEQ ID NO: 42.

2. The polypeptide of claim 1, wherein the polypeptide is produced recombinantly.

3. The polypeptide of claim 1, wherein the polypeptide is glycosylated.

4. The polypeptide of claim 1, wherein the polypeptide comprises an albumin fusion wherein an albumin, an albumin variant, or an albumin fragment is conjugated to the polypeptide.

5. The polypeptide of claim 4, wherein the albumin, albumin variant, or albumin fragment is human serum albumin, a human serum albumin variant, or a human serum albumin fragment.

6. The polypeptide of claim 4, wherein the albumin, albumin variant, or albumin fragment is bovine serum albumin, a bovine serum albumin variant, or a bovine serum albumin fragment.

7. The polypeptide of claim 4, wherein the albumin, albumin variant, or albumin fragment is cyno serum albumin, a cyno serum albumin variant, or a cyno serum albumin fragment.

8. The polypeptide of claim 4, wherein the albumin, albumin variant, or albumin fragment is conjugated to the polypeptide at the carboxyl terminus, the amino terminus, or both the carboxyl and amino termini.

9. The polypeptide of claim 8, wherein the albumin, albumin variant, or albumin fragment is conjugated to the polypeptide at the amino terminus.

10. The polypeptide of claim 4, wherein the albumin, albumin variant, or albumin fragment is conjugated to the polypeptide via a linker.

11. The polypeptide of claim 10, wherein the linker is a cleavable linker.

12. The polypeptide of claim 11, wherein the cleavable linker can be cleaved by a protease.

13. The polypeptide of claim 10, wherein the linker is a non-cleavable linker.

14. The polypeptide of claim 4, wherein the albumin, albumin variant, or albumin fragment is excised from the albumin fusion prior to being secreted from a cell.

15. A transformed or host cell that expresses the polypeptide of claim 1.

16. A pharmaceutical composition, comprising the polypeptide of claim 1, and a pharmaceutically acceptable diluent, carrier or excipient.

17. The pharmaceutical composition of claim 16, further comprising at least one additional prophylactic or therapeutic agent.

18. A sterile container comprising the pharmaceutical composition of claim 16.

19. The sterile container of claim 18, wherein the sterile container is a syringe.

20. A kit comprising the sterile container of claim 19.

21. The kit of claim 20, further comprising a second sterile container comprising at least one additional prophylactic or therapeutic agent.

22. A nucleic acid molecule encoding the polypeptide of claim 1.

23. The nucleic acid molecule of claim 22, wherein the nucleic acid molecule is operably linked to an expression control element that confers expression of the nucleic acid molecule encoding the polypeptide in vitro, in a cell or in vivo.

24. A vector comprising the nucleic acid molecule of claim 22.

25. The vector of claim 24, wherein the vector comprises a viral vector.

* * * * *